US007229757B2

(12) United States Patent
Barrett et al.

(10) Patent No.: US 7,229,757 B2
(45) Date of Patent: Jun. 12, 2007

(54) COMPOUNDS DISPLAYED ON ICOSAHEDRAL PHAGE AND METHODS OF USING SAME

(75) Inventors: Ronald W. Barrett, Saratoga, CA (US); William J. Dower, Menlo Park, CA (US); Mark Gallop, Los Altos, CA (US); Thomas F. Woiwode, San Carlos, CA (US); Steven E. Cwirla, Menlo Park, CA (US)

(73) Assignee: Xenoport, Inc., Santa Clara, CA (US)

( * ) Notice: Subject to any disclaimer, the term of this patent is extended or adjusted under 35 U.S.C. 154(b) by 582 days.

(21) Appl. No.: 10/105,029

(22) Filed: Mar. 21, 2002

(65) Prior Publication Data
US 2007/0082330 A1  Apr. 12, 2007

Related U.S. Application Data

(60) Provisional application No. 60/277,537, filed on Mar. 21, 2001.

(51) Int. Cl.
*C12Q 1/68* (2006.01)
(52) U.S. Cl. ........................................................ 435/6
(58) Field of Classification Search .................... 435/5, 435/6, 69.1, 69.7, 468, 320.1, DIG. 1, DIG. 2, 435/DIG. 4, DIG. 14, DIG. 17, DIG. 24; 536/23.4
See application file for complete search history.

(56) References Cited

U.S. PATENT DOCUMENTS

| 5,403,484 | A  |   | 4/1995  | Ladner et al.          |
|-----------|----|---|---------|------------------------|
| 5,514,548 | A  |   | 5/1996  | Krebber et al.         |
| 5,571,698 | A  |   | 11/1996 | Ladner et al.          |
| 5,639,603 | A  |   | 6/1997  | Dower et al.           |
| 5,723,598 | A  |   | 3/1998  | Lerner et al.          |
| 5,766,905 | A  | * | 6/1998  | Studier et al. ......... 435/235.1 |
| 5,837,500 | A  |   | 11/1998 | Ladner et al.          |
| 6,027,890 | A  |   | 2/2000  | Ness et al.            |
| 6,057,098 | A  |   | 5/2000  | Buechler et al.        |
| 6,117,632 | A  | * | 9/2000  | O'Mahony ................ 435/6 |
| 6,740,524 | B1 | * | 5/2004  | Akuta et al. ............ 435/456 |
| 6,777,239 | B2 |   | 8/2004  | Dower et al.           |

FOREIGN PATENT DOCUMENTS

| WO | WO 93/11236 A1 | 6/1993  |
|----|----------------|---------|
| WO | WO 97/10507 A1 | 3/1997  |
| WO | WO 98/51325 A2 | 11/1998 |
| WO | WO 98/51825 A1 | 11/1998 |
| WO | WO 01/05950 A2 | 1/2001  |
| WO | WO 01/18234 A1 | 3/2001  |
| WO | WO 01/23619 A1 | 4/2001  |
| WO | WO 02/077182 A2 | 10/2002 |

OTHER PUBLICATIONS

Jiang et al., Infection and Immunity 65(11):4770-4777 (1997).*
Armstrong, John, et al. Orientation of the virion during assembly and disassembly, IRL Press Limited, 1983. pp. 1641-1646.
Brenner, Sidney, et al., Encoded combinatorial chemistry; *Proc. Natl Acad. Sci. USA*; Jun. 1992, pp. 5381-5383, vol. 89.
Chang, Thomas K, et al, Subtiligase: A tool for semisynthesis of proteins; *Proc. Natl. Acad. Sci. USA*: Dec. 1994, pp. 12544-12548; vol. 91.
Cwirla, Steven E., et al, Peptides on phage: A vast library of peptides for identifying ligands, *Proc. Natl. Acad. Sci. USA*; Aug. 1990, pp. 6378-6382, vol. 87.
Devlin, James J., et al., Random Peptide Libraries: A Source of Specific Protein Binding Molecules, *Science*, Jul. 27, 1990, pp. 404-406, vol. 249.
Dwyer, Mary A., Biosynthetic phage display: a novel protein engineering tool combining chemical and genetic diversity: *Chemistry & Biology 2000*; Mar. 20, 2000; vol. 7, No. 4.
Ellman, Jonathan A., et al., Combinatorial Chemistry, *Current Opinion in Chemical Biology*: 1998, pp. 317-319, vol. 2.
Nakashima, Yastusugu, Chemical Modification and Molecular Orientation of the B Protein in the Filamentous Bacterial Virus Pf1; *J. Mol. Biol.*, 1980; pp. 493-501, vol. 138.
Sandman, Karen E., et al.; Phage Display of Selenopeptides, *J Am. Chem. Soc.*, 2000, pp. 960-961: vol. 122.
Scott, Jamie K, et al., Searching for Peptide Ligands with an Epitope Library, *Science*, Jul. 27, 1990, pp. 386-390, vol. 249.
U.S. Appl. No. 09/675,525, Barrett et al.
Bukanov et al. "A Modified Two-Step Phage Display Selection for Isolation of Polycytin-1 Ligands" Funct. Integr. Genomics, 2000, pp. 193-199, vol. 1.
Crameri R. et al. "Display of Biologically Active Proteins on the Surface of Filamentous Phages: A cDNA Cloning System for Selection of Functional Gene Products Linked to the Genetic Information Responsible for their Production" Gene, 1993, pp. 69-75, vol. 137, Elsevier Science, NL.
Danner et al. "T7 Phage Display: A Novel Genetic Selection System for Cloning RNA-binding Proteins from cDNA Libraries" PNAS, Nov. 6, 2001, pp. 12954-12959, vol. 98, No. 23.
Dente, Luciana et al. "Modified Phage Peptide Libraries as a Tool to Study Specificity of Phophorylation and Recognition of Tyrosine Containing Peptides" J. Molecular Biology, Jul. 27, 1997, pp. 694-703, vol. 269, No. 5, England.

(Continued)

Primary Examiner—James Schultz
Assistant Examiner—Jeffrey S. Lundgren
(74) Attorney, Agent, or Firm—Townsend and Townsend and Crew LLP

(57) ABSTRACT

Icosahedral phage and collections thereof that display various compounds are provided. In some instances, the icosahedral phage include nucleic acid tags that serve to record a characteristic of the compound or compounds that are attached to the phage. A number of different methods for using the icosahedral phage to screen a library of compounds for a desired biological activity are also provided, especially assays for compounds that are substrates for receptor-mediated transport processes such as endocytosis and transcytosis.

26 Claims, 20 Drawing Sheets

OTHER PUBLICATIONS

MacLean, D. et al. "Encoded combinatorial chemistry; synthesis and screening of a library of highly functionalized pyrrolidines." Proceedings of the National Academy of Sciences of the United States of America, Apr. 1, 1997, pp. 2805-2810, vol. 94, No. 7, USA.

Woiwode, Thomas F. et al. "Synthetic compound libraries displayed on the surface of encoded bacteriophage." Chemistry and Biology, Sep. 2003, pp. 847-858, vol. 10, No. 9, England.

Cwirla et al., "Peptides on phage: A vast library of peptides for identifying ligands," *PNAS*, 87:6378-6382 (1990).

Hogenboom et al., "Multi-subunit proteins on the surface of filamentous phage: methodologies for displaying antibody (Fab) heavy and light chains," *Nuc. Acids Res.*, 19(15):4133-4137 (1991).

Rosenberg et al., "T7 Select® Phage Display System: A powerful new protein display system based on bacteriophage T7," *inNovations*, 6:1-6 (1996).

Scott et al., "Searching for Peptide Ligands with an Epitope Library," *Science*, 249:386.

Woiwode et al., "Synthetic Compound Libraries Displayed on the Surface of Encoded Bacteriophage," *Chemistry & Biology*, 10:847-858 (2003).

Written Opinion for application No. PCT/US00/26849, dated Jan. 11, 2002.

International Search Report for application No. PCT/US00/26849, dated Feb. 28, 2001.

International Search Report for application No. PCT/US02/09095, dated Apr. 30, 2003.

Supplemental European Search Report for application No. EP 00 96 8494, dated Jul. 7, 2004.

* cited by examiner

T7 display (gene 10B)

```
                   N  S  G  G  G  G  G  L  N  D  I  F  E  A  Q  K  I  E  W  H  E  *
gene 10B .. AATTCTGGAGGCGGGGGGGGTCTTAATGATATTTTTGAGGCTCAGAAGATTGAGTGGCATGAGTAAGTAACTAA
            ─────────────────── ────────────────────────────────────
                  spacer             biotinylation substrate sequence
                                                    │
                                                  biotin
```

FIG. 11

Lanes 1-3: T7 phage treated with fluorescein-$CO_2H$ (2X dilutions)
Lanes 4-6: T7 phage treated with fluorescein-NHS ester (2X dilutions)
Lanes 7: MW markers Hybridization of 32P cRNA probe derived from KB cell lysate
to 36-member folate analog library archive array

COMPOUNDS DISPLAYED ON ICOSAHEDRAL PHAGE AND METHODS OF USING SAME

CROSS-REFERENCES TO RELATED APPLICATIONS

This application claims the benefit of U.S. Provisional Application No. 60/277,537, filed Mar. 21, 2001, which is incorporated herein by reference in its entirety for all purposes. This application is also related to U.S. patent application Ser. No. 09/675,525, filed Sep. 29, 2000, which claims the benefit of U.S. Provisional Application No. 60/156,675, filed Sep. 29, 1999, both of which are incorporated herein by reference in their entirety for all purposes.

BACKGROUND

The search for new compounds frequently involves screening large libraries of compounds to identify a small subset of compounds that have a desired activity or characteristic. The use of combinatorial chemistry and high-throughput screening has greatly increased the speed at which lead compounds can be identified. Indeed, such techniques have made available an increasing number of potential therapeutic agents. The challenge once such compounds have been identified is to formulate them for oral delivery. It is preferred that such therapeutic agents are amenable to oral delivery because of the decreased costs associated with this type of delivery and the clear preference of patients for oral administration. However, many agents fail at the preclinical or early clinical stage due to poor pharmacokinetics. Other potential targets for pharmaceutical agents are largely ignored due to anticipated problems of pharmaceutical agent delivery. Formulating compounds for efficient oral bioavailability has proven particularly difficult because of problems associated with uptake and susceptibility to metabolic enzymes in the intestinal tract. Delivery of compounds across the blood brain barrier or targeting compounds to specific tissues has also proven problematic.

There are two major specific transport systems of xenobiotics into and through cells: carrier-mediated systems and receptor-mediated systems. Some xenobiotics can also be taken up by passive diffusion between or through cells. Carrier-mediated systems utilize transport proteins that are anchored to the cell membrane, typically by a plurality of membrane-spanning loops and function by transporting their substrates via an energy-dependent flip-flop mechanism. Carrier-mediated transport systems are involved in the active transport of many important nutrients such as vitamins, sugars, and amino acids, as well as xenobiotic compounds. These molecules are transported by carrier-mediated systems from the lumen of the intestine into the systemic circulation or across the blood brain barrier. Carrier-mediated transporters are also present in organs such as liver and kidney, where the proteins are involved in the excretion or reabsorption of circulating compounds.

Receptor-mediated transport systems differ from the carrier-mediated systems in that rather than ferrying the substrate/ligand across the membrane, substrate binding triggers an invagination and encapsulation process that results in the formation of various transport vesicles to carry the substrate (and sometimes other molecules) into and through the cell. This process of membrane deformations that result in the internalization of certain substrates and their subsequent targeting to certain locations in the cytoplasm is referred to as endocytosis. Endocytosis encompasses several specific variations, including, for example, receptor mediated endocytosis (RME).

RME involves several defined steps beginning with the binding of a substrate to a cell-surface receptor and subsequent invagination of the membrane to form an internal vesicle variously called an early endosome, a receptosome or CURL (compartment of uncoupling receptor and ligand). In some endocytic events, after a substrate binds to its specific receptor, the substrate-receptor complex accumulates in coated pits that contain high concentrations of clathrin subunits that appear to aid in the membrane invagination process. Following internalization, the clathrin coat is lost and the pH in the endosome is lowered, thus resulting in the dissociation of the receptor-substrate complex. The endosome moves randomly or along microtubules to the trans-Golgi reticulum where the endosome is converted into one of a variety of different sorting vesicles (e.g., tubulovesicular complexes and late endosomes or multivesicular bodies). The fate of the receptor and substrate depends upon the type of sorting vesicle formed. Some ligands and receptors are recycled to the cell surface where the substrate is released and the receptor reinternalized into the membrane. In other instances, the substrate is directed to and destroyed in a lysosome, and the receptor is recycled. One type of RME is transcytosis, which refers to the process wherein an endocytotic vesicle is transported to the opposite membrane surface of a polarized cell. RME is capable of transporting a variety of compounds, including immunoglobulins, lectins, vitamins and metal ions.

A number of attempts have been made to assay or identify substrates of various transport proteins or to modify pharmaceutical agents to be improved substrates of transport proteins. Substrates so identified could be utilized to transport other compounds into or through cells. (See, e.g., Kramer et al, *J. Biol. Chem.* (1994), 269:10621; Mills et al, *Biochim. Biophys. Acta* (1992), 1126: 35; Börner et al, *Eur. J. Biochem.* (1998) 255: 698; Dieck et al, *Glia*, (1999) 25: 10; Otto et al, *Am. J. Physiol.* (1996) 271:C210; Abe et al, *Biooconjugate Chem.* (1999) 10: 24); Hussain et al, *Pharm. Res.* 1997, 14, 613 and McClean et al, *Eur. J. Pharm. Sci.* 1998, 6, 153). Some assays have involved measuring the uptake or transcellular flux of labeled compounds. Other assays have measured uptake of unlabelled compound by HPLC. However, many existing assays are tedious, are only capable of low throughput, and the delivery of many pharmaceutical agents and potential pharmaceutical agents remains to be improved. Furthermore, in assays for transcytosis and endocytosis, assays can be complicated because of the size and shape constraints imposed on assay agents by the vesicles that are part of these transport systems.

One potential approach for identifying substrates for transporter proteins is to utilize phage display technology. Phage display methods typically involve the insertion of random oligonucleotides into a phage genome such that they direct a bacterial host to express peptide libraries fused to phage coat proteins (e.g., filamentous phage pIII, pVI or pVIII). Incorporation of the fusion proteins into the mature phage coat results in the peptide encoded by the exogenous sequence being displayed on the exterior surface of the phage, while the exogenous sequence encoding the peptide resides within the phage particle. However, a significant limitation with current phage-display technology, is that it is only applicable to the display of peptides. Many of the most effective drugs, however, are small organic molecules.

SUMMARY

Icosahedral phage, including spherical and pseudo spherical phage, conjugated to a variety of different compounds are provided herein, as are methods for using such phage in diverse types of assays. Phage of this type have unexpectedly been found to provide improved detection in assays for transcytosis and endocytosis as compared to other phage types such as filamentous phage.

In some instances the icosahedral phage display an expressed polypeptide that is part of a fusion protein that includes a capsid protein of the phage. Other icosahedral phage, display compounds other than expressed polypeptides (e.g., compounds from a library, such as a combinatorial library). Such compounds can be separately synthesized and then attached to the phage or synthesized directly on the phage according to methods disclosed herein. The compounds can optionally be linked to the icosahedral phage via one or more linkers. For example, the compound and phage can be joined by a linker attached to the phage and/or to the compound to be attached thereto.

Certain icosahedral phage that are provided include a tag (e.g., a nucleic acid tag) that codes for at least one characteristic of the compound(s) attached to the phage. With some phage, the tag is a heterologous nucleic acid tag that is other than a nucleic acid segment that encodes for a polypeptide (or portion thereof) that is displayed by the phage. The phage can also include an optional label to facilitate detection in the various screening assays described herein.

The icosahedral phage can optionally display multiple compounds. The multiple compounds displayed can be multiple copies of a single compound or one or more copies of multiple different compounds. Utilizing attachment methods disclosed herein, one can selectively attach the compounds to different coat proteins and/or attachment sites on the coat proteins.

Methods of preparing icosahedral phage of the type just described are also provided.

Some of the screening assay methods disclosed herein involve providing a plurality of icosahedral phage displaying different compounds, and then assaying the icosahedral phage to identify at least one icosahedral phage displaying at least one compound with a desired property. A number of different assays can be conducted with the compound-displaying phage described herein including, but not limited to, capacity to bind to a receptor, the capacity to be transported into or through a cell, the capacity to be a substrate or inhibitor for an enzyme, the capacity to kill bacteria, fungi or other microorganisms, and the capacity to agonize or antagonize a receptor. As just noted, however, the icosahedral phage are preferably utilized in endocytosis and transcytosis assays.

Essentially any type of compound can be displayed on the phage. Such compounds include expressed polypeptides which are part of a fusion protein including a coat protein of the icosahedral phage. Other compounds are compounds other than expressed polypeptides. These compounds can be separately synthesized and then attached to the phage or can be directly synthesized on the phage surface. The compound displayed by the icosahedral phage can optionally be encoded using a heterologous nucleic acid tag that is incorporated into the phage. For phage displaying an expressed polypeptide, the heterologous nucleic acid encoding for the displayed polypeptide can function as the tag. For phage displaying compounds other than an expressed polypeptide, the tag often is not expressed, although this is not required.

In addition to their use in screening assays to identify new substrates for transport processes, the compound-displaying icosahedral phage can also be utilized to identify potential new transporter proteins. In some of the screens of this type, assays are conducted with a population of cells that has been transformed with a DNA library encoding a plurality of receptor-type transport proteins and express a plurality of receptor-type transport proteins. After contacting the cells with a plurality of compound-displaying icosahedral phage, these methods involve determining the identity of the cell through which at least one phage is transported. Such cells express a candidate transport protein capable of transporting the compound displayed by the at least one phage into or through the cell.

The screening assays can be conducted in both in vitro and in vivo formats. One in vitro format involves layering polarized cells above a membrane that is permeable to the compound-displaying phage and applying the phage to the apical side of the polarized cells, whereby the at least one icosahedral phage passes through the polarized cell monolayer and is collected on the basolateral side of the polarized cells.

Some in vivo assays involve introducing a plurality of icosahedral phage into a body compartment or tissue of an animal under conditions such that at least one icosahedral phage is transported from the body compartment through cells which express one or more transport proteins and which line the body compartment into a tissue or fluid. The at least one transported phage is then recovered from the tissue or fluid and the identity of the displayed compound determined. A compound with such activity is a candidate substrate for one of the transport proteins expressed in the cells lining the body compartment. In some instances, the phage are introduced into the intestine of the animal, the cells through which transport occurs are intestinal epithelial cells and the at least one phage is retrieved from the blood of the animal. With other assays, phage are introduced into the circulatory system of the animal, the cells through which transport occurs are endothelial cells and the at least one phage is retrieved from the brain.

A number of different techniques can be utilized to detect transport. In some instances, a sample potentially containing transported phage is collected and then plated out onto a population of cells for detection of plaque formation. Because the methods described herein utilize phage that can be readily amplified, the methods are capable of very high sensitivity. While the phage can essentially serve as a label, the phage can optionally be labeled with a detectable label/reporter to aid detection of transport.

Compounds displayed by active phage can be identified in a variety of ways. If the displayed compound is an expressed polypeptide, then determination of the heterologous sequence of a phage having the desired activity identifies the displayed polypeptide. As indicated above, some phage include a tag to code for the displayed compound. Thus, by decoding the heterologous nucleic acid tag of a phage with the desired activity, one can identify the displayed compound or at least one characteristic of the displayed compound having the desired activity.

BRIEF DESCRIPTION OF THE DRAWINGS

FIG. 11 shows a 16-amino acid BirA substrate sequence inserted into the 3' end of gene 10B, the major coat protein of T7 phage.

FIG. 19A is a chart showing the extent of uptake into cells of filamentous phage conjugated to folate under conditions in which endocytosis can occur (incubation at 37° C.) and under conditions in which endocytosis is inhibited (incubation at 4° C.). FIG. 19B shows results from similar experiments conducted with icosahedral phage that are conjugated to folate.

DETAILED DESCRIPTION

I. Definitions

Figure 1:
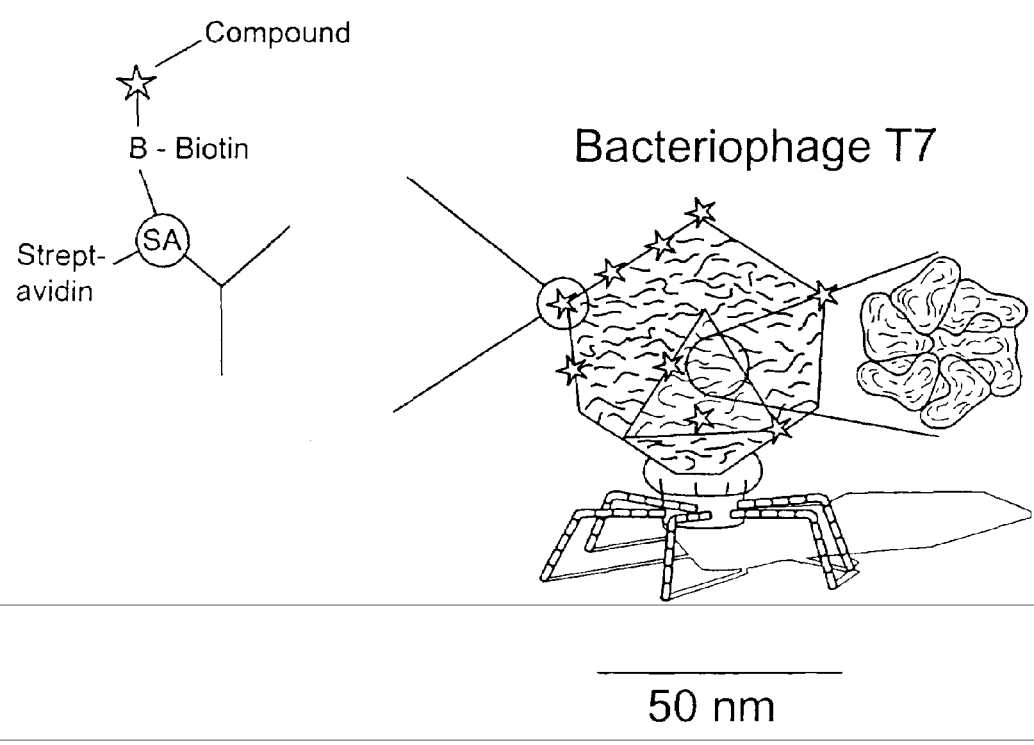
FIG. 1 is a schematic representation of a specific example of a phage as disclosed herein, namely a phage wherein the linker attached to the phage is streptavidin (SA) and the linker attached to the library compound is biotin (B).
Figure 2A:
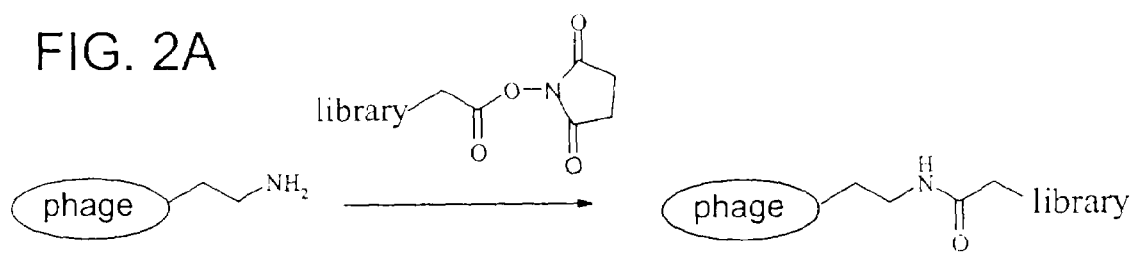
FIGS. 2A-2D depict exemplary strategies to effect the direct chemical conjugation of small molecule libraries to phage coat proteins.
Figure 2B:
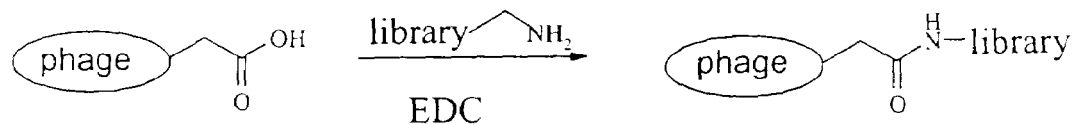
Figure 2C:
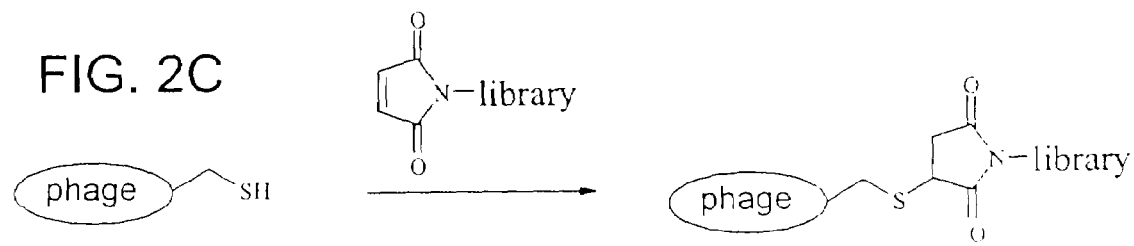
Figure 2D:
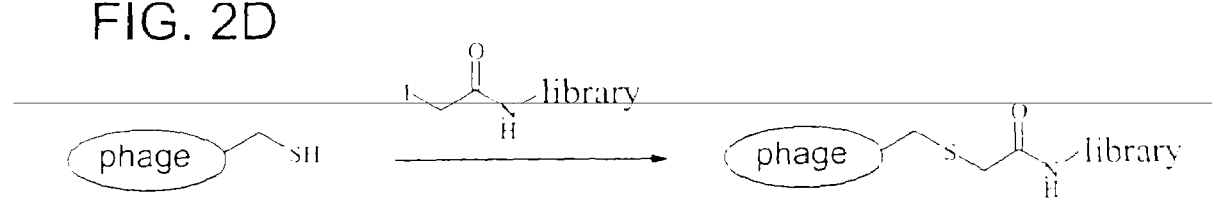

The term "nucleic acid" refers to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides.

A "polynucleotide" refers to a single or double-stranded polymer of deoxyribonucleotide or ribonucleotide bases.

An "oligonucleotide" is a single-stranded nucleic acid typically ranging in length from 2 to about 500 bases. Oligonucleotides are often synthetic but can also be produced from naturally occurring polynucleotides. Oligonucleotides can be prepared by any suitable method, including, for example, cloning and restriction of appropriate sequences and direct chemical synthesis by a method such as the phosphotriester method of Narang et al., Meth. Enzymol. 68:90-99 (1979); the phosphodiester method of Brown et al., Meth. Enzymol. 68:109-151 (1979); the diethylphosphoramidite method of Beaucage et al., Tetrahedron Lett. 22:1859-1862 (1981); and the solid support method of U.S. Pat. No. 4,458,066.

A "probe" is an nucleic acid capable of binding to a target nucleic acid of complementary sequence through one or more types of chemical bonds, usually through complementary base pairing, usually through hydrogen bond formation, thus forming a duplex structure. The probe binds or hybridizes to a "probe binding site."

A "functional group" refers to an atom or group of atoms that defines the structure of a compound or family of compounds, while also determining the properties of the compound. Exemplary functional groups include, carboxyl, amino, sulfhydryl, carbonyl and double and triple bonds, for example.

The terms "polypeptides", "proteins" and "peptides" are used interchangeably and mean a polymer of amino acids. In some instances, the term applies to a polymer of the naturally occurring amino acids. The term can also apply to amino acid polymers in which one or more amino acids are chemically analogues of a corresponding naturally occurring amino acid or in which the polypeptide backbone has been modified.

The term "expressed polypeptide" refers to a polypeptide, protein, or peptide produced by translational expression of the nucleic acid of a phage.

The term "compound" refers generally to an agent that can be displayed on an exterior surface of a phage. The compound can be an expressed polypeptide or a compound other than an expressed polypeptide.

The term "a compound other than an expressed polypeptide" means a compound other than a polypeptide, protein or peptide produced by translational expression of the nucleic acid of a phage.

Reference to a compound being "displayed" on an phage means that the compound is attached to a group (e.g., an amino acid residue) located at the exterior surface of the phage.

A "small molecule" means a molecule having a molecular weight of less than 2000 daltons, in some instances less than 1000 daltons, and in still other instances less than 500 daltons or less. Such molecules include, for example, heterocyclic compounds, carbocyclic compounds, sterols, amino acids, lipids, and nucleic acids.

The term "naturally occurring" as applied to an object refers to the fact that an object can be found in nature.

An "exogenous" species is refers to a species that is not normally present in or displayed on a phage, but can be introduced into a phage by one or more genetic, biochemical or other methods. Normal presence in the phage is determined with respect to the particular developmental stage and environmental conditions of the a phage. An exogenous species can be, among other things, a small molecule, such as is generated by a combinatorial chemistry process, or a macromolecule such as a protein, nucleic acid, carbohydrate, lipid, glycoprotein, lipoprotein, polysaccharide, or any modified derivative of the above molecules, or any complex comprising one or more of the above molecules. When used in reference to a group such as a functional group or attachment site on the surface of a phage, exogenous means the functional group or attachment site that does not naturally occur on the surface of the phage. Such a group can be a functional group appearing at the surface of the phage that has been derivatized or modified, for example.

By contrast, an "endogenous" species is one that is normally present in or on a phage at a particular developmental stage under particular environmental conditions.

The term "operably linked" refers to functional linkage between a nucleic acid expression control sequence (such as a promoter, signal sequence, or array of transcription factor binding sites) and a second polynucleotide, wherein the expression control sequence affects transcription and/or translation of the second polynucleotide.

A "heterologous sequence" or a "heterologous nucleic acid," is one that originates from a source foreign to the particular phage, or, if from the same source, is modified from its original form. Thus, a heterologous gene in a phage includes a gene that, although being endogenous to the particular host phage, has been modified. Modification of the heterologous sequence can occur, e.g., by treating the DNA with a restriction enzyme to generate a DNA fragment that is capable of being operably linked to the promoter. Techniques such as site-directed mutagenesis are also useful for modifying a heterologous nucleic acid.

The term "recombinant" when used with reference to a phage indicates that the phage replicates a heterologous nucleic acid, or expresses a peptide or protein encoded by a heterologous nucleic acid. Recombinant phage can contain genes that are not found within the native (non-recombinant) form of the phage. Recombinant phage can also contain genes found in the native form of the phage wherein the genes are modified and re-introduced into the phage by artificial means. The term also encompasses phage that contain a nucleic acid endogenous to the phage that has been modified without removing the nucleic acid from the phage; such modifications include those obtained by gene replacement, site-specific mutation, and related techniques.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide.

The term "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains, respectively.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments can be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies, more preferably single chain Fv (scFv) antibodies in which a variable heavy and a variable light chain are joined together (directly or through a peptide linker) to form a continuous polypeptide.

A single chain Fv ("scFv") polypeptide is a covalently linked VH::VL heterodimer which can be expressed from a nucleic acid including VH- and VL-encoding sequences either joined directly or joined by a peptide-encoding linker. Huston, et al. Proc. Nat. Acad. Sci. USA, 85:5879-5883 (1988). A number of strategies for converting the naturally aggregated—but chemically separated light and heavy polypeptide chains from an antibody V region into an scFv molecule that will fold into a three dimensional structure substantially similar to the structure of an antigen-binding site, have been reported. See, e.g. U.S. Pat. Nos. 5,091,513 and 5,132,405 and 4,956,778.

An "antigen-binding site" or "binding portion" refers to the part of an immunoglobulin molecule that participates in antigen binding. The antigen-binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. Sequences of proteins of immunological interest, 4th ed. U.S. Dept. Health and Human Services, Public Health Services, Bethesda, Md. (1987).

The term "epitope" refers to the portion of an antigen that interacts with an antibody. More specifically, the term epitope includes any protein determinant capable of specific binding to an immunoglobulin or T-cell receptor.

The phrases "specifically binds" when referring to a protein or "specifically immunoreactive with" when referring to an antibody, refers to a binding reaction which is determinative of the presence of the protein in the presence of a heterogeneous population of proteins and other biologics. Thus, under designated conditions, a specified ligand binds preferentially to a particular protein and does not bind in a significant amount to other proteins present in the sample. A molecule or ligand (e.g., an antibody) that specifically binds to a protein has an association constant of at least $10^3$ M$^{-1}$ or $10^4$ M$^{-1}$, sometimes $10^5$ M$^{-1}$ or $10^6$ M$^{-1}$, in other instances $10^6$ M$^{-1}$ or $10^7$ M$^{-1}$, preferably $10^8$ M$^{-1}$ to $10^9$ M$^{-1}$, and more preferably, about $10^{10}$ M$^{-1}$ to $10^{11}$ M$^{-1}$ or higher. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual*, Cold Spring Harbor Publications, New York, for a description of immunoassay formats and conditions that can be used to determine specific immunoreactivity.

A "binding pair" or "binding partners" refers to a first and second moiety that specifically bind to each other. Exemplary binding pairs include, but are not limited to, biotin and either streptavidin, avidin or neutravidin; a hapten and an antibody thereto; and an enzyme and an inhibitor.

Figure 9:
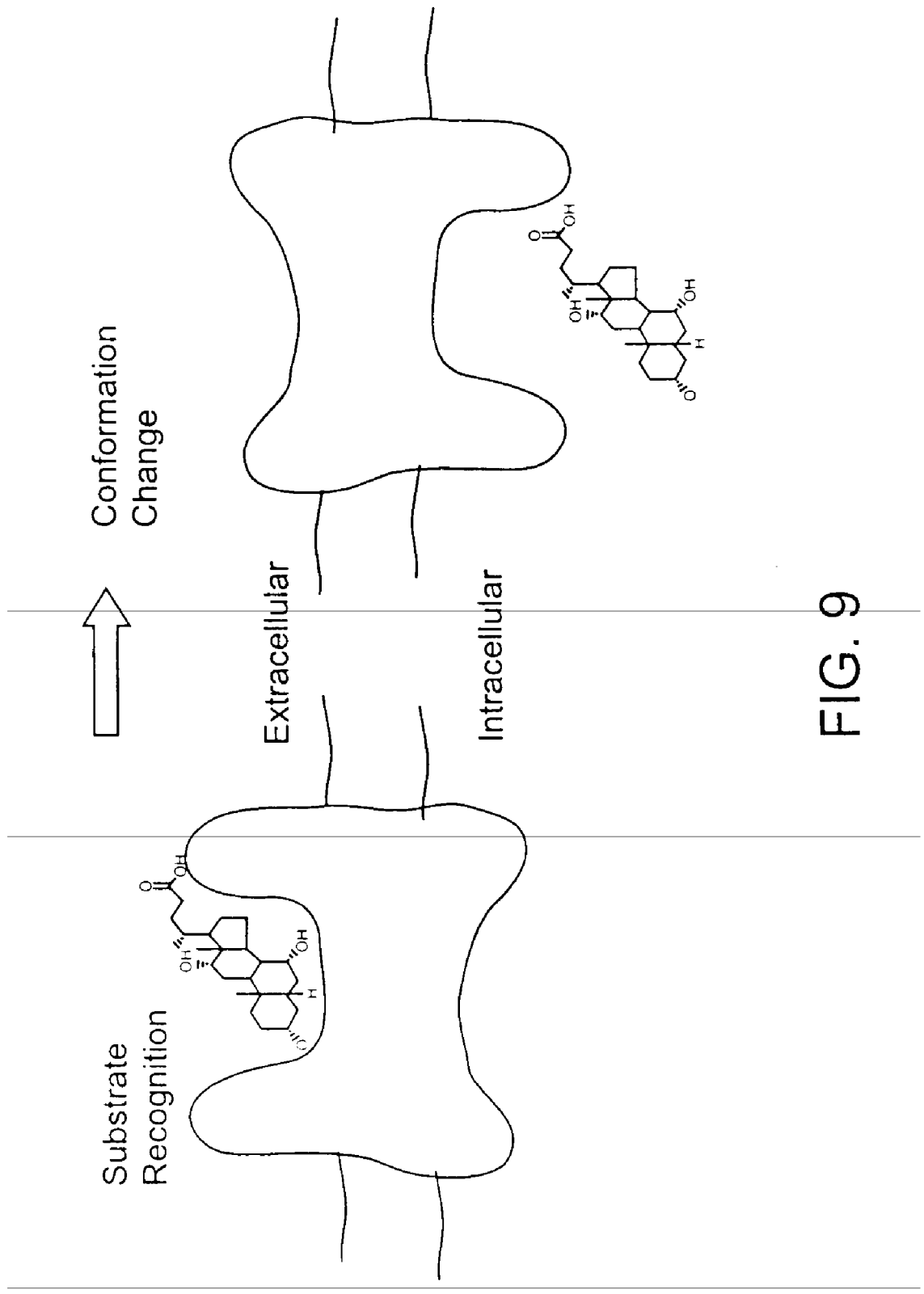
FIG. 9 illustrates transport of a substrate into a cell by a carrier-type transporter.
Figure 10B:
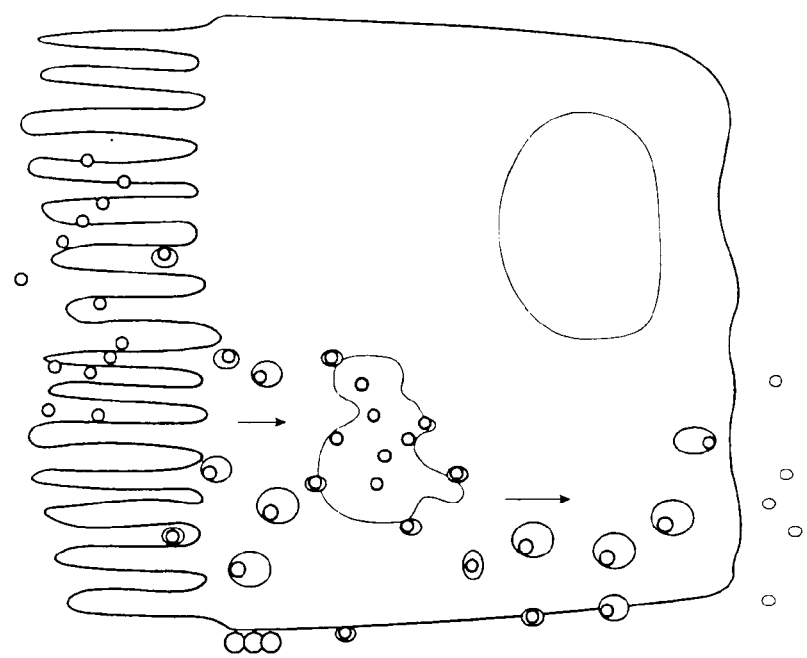
FIGS. 10A and 10B illustrate transport of a substrate into a cell by a receptor-type transporter in which substrates bind to cell-surface receptors and are subsequently encapsulated into vesicles and transported into or through the cell from the intestinal lumen to the blood system.
Figure 10A:
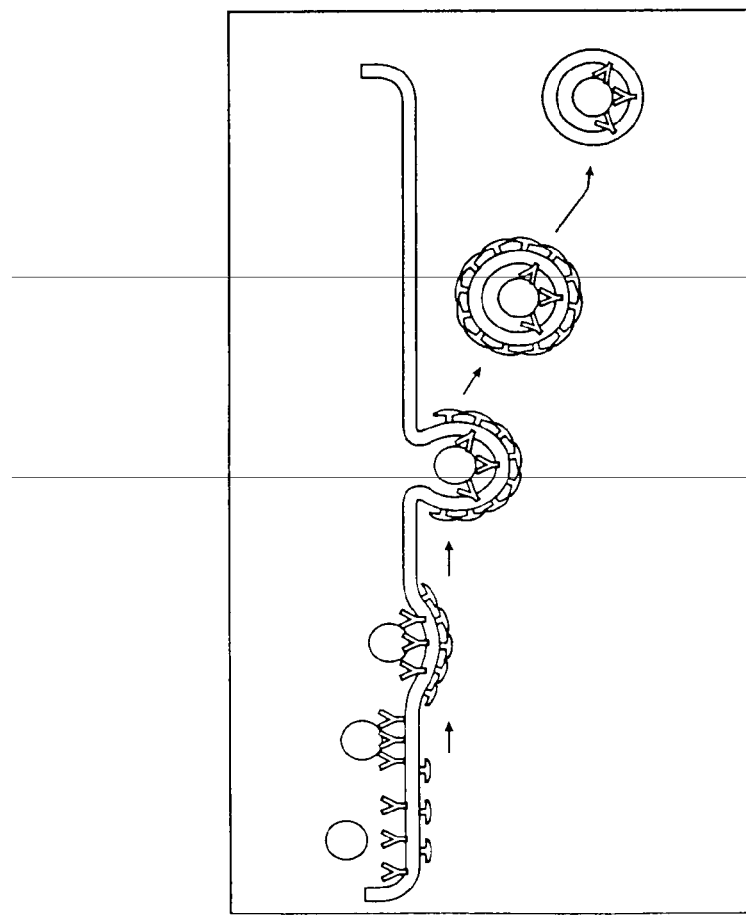

A "transport protein" is a protein that has a direct or indirect role in transporting a molecule into and/or through a cell. The term includes, for example, membrane-bound proteins that recognize a substrate and effects its entry into a cell by a carrier-mediated transporter (see FIG. 9) or by receptor-mediated transport (see FIGS. 10A and 10B). Transport proteins are sometimes referred to as "transporter proteins" or simply "transporters." The term also includes intracellularly expressed proteins that participate in trafficking of substrates through or out of a cell. The term also includes proteins or glycoproteins exposed on the surface of a cell that do not directly transport a substrate but bind to the substrate holding it in proximity to a receptor or transporter protein that effects entry of the substrate into or through the cell. Transport proteins involved in carrier-mediated transport are referred to as carrier-type transport proteins or simply carrier-type transporters. Those transport proteins involved in receptor-mediated transport are referred to as receptor-type transport proteins or simply receptor-type transporters.

Some examples of transporter proteins effecting carrier-mediated transport of nutrients, vitamins and xenobiotics include, but are not limited to: glutamate/neutral amino acid transporter; facilitated glucose transporter; d2/NBAT and 4F2 transporter; sodium/glucose transporter; GABA transporter; amino acid permease transporter; sodium/bile acid transporter; proton/oligopeptide transporter; monoamine transporter; folate transporter; organic anion/prostaglandin transporter; organic cation/organic anion transporter; sodium/ascorbic acid transporter; fatty acid transporter; sodium/nucleoside transporter and facilitated nucleoside transporter. Other examples of carrier proteins include: the ileal bile acid transporter (ASBT or IBAT); the liver bile acid transporters (NTCP); dipeptide transporters; oligopeptide transporters; simple sugar transporters (e.g., SGLT1); phosphate transporters; monocarboxylic acid transporters; ATP-binding cassette (ABC) family (e.g., P-glycoprotein); organic anion transporters (OATP); organic cation transporters; amino acid transporters; nucleoside transporters; vitamin transporters; and electrogenic transporters that carry charged substrates.

Examples of receptor-mediated transport proteins include: viral receptors, immunoglobulin receptors, bacterial toxin receptors, plant lectin receptors, bacterial adhesion receptors, vitamin transporters and cytokine growth factor receptors.

A "substrate" of a transport protein is a compound whose uptake into or passage through a cell is facilitated by the transport protein.

The term "ligand" of a transport protein includes substrates and also includes other compounds that bind to the transport protein without being taken up or transported through a cell. Some ligands by binding to the transport protein inhibit or antagonize uptake of the compound or passage of the compound through a cell by the transport protein. Some ligands by binding to the transport protein promote or agonize uptake or passage of the compound by the transport protein or another transport protein. For example, binding of a ligand to one transport protein can promote uptake of a substrate by a second transport protein in proximity with the first transport protein.

The term "endocytosis" has the meaning known in the art and generally refers to a form of transport utilizing a receptor-mediated transport system in which binding of a ligand to a cell-surface receptor results in the formation of an internal vesicle within the cell that encompasses the substrate, or at least a portion thereof, and then movement of the vesicle into the cell (see also Background section).

The term "transcytosis" also has the meaning known in the art and refers to a process similar to that described for endocytosis, except that the vesicle with the encapsulated material is transported to the opposite membrane of a polarized cell (see also Background section). The term also refers to any other invagination to encompass materials outside of the cell or inclusion into a vesicle.

A "tissue" refers to an aggregation of similar cells united in performance of a particular function. The tissue can be part of a living organism, a section excised from a living organism, or can be artificial. An artificial tissue is one in which the aggregation of cells are grown to function similar to a tissue in a living organism. The aggregated cells, however, are not obtained from a host (i.e., a living organism). Artificial tissues can be grown in vivo or in vitro.

II. General

Disclosed herein are icosahedral phage that display a wide variety of compounds and methods of utilizing the icosahedral phage in diverse assays, particularly screening assays to identify substrates for transport proteins, especially receptor-mediated transport proteins, and assays to identify new transport proteins. The methods disclosed herein are based in part on the unexpected finding that icosahedral phage that display such compounds yield improved assay results as compared to the results obtained in identical assays conducted with other types of phage (e.g., filamentous phage). For instance, certain endocytosis or transcytosis screening assays of compounds displayed by icosahedral phage are less susceptible to background interferences and can in some instances provide improved signal-to-noise ratios as compared to similar assays conducted with filamentous phage. Consequently, in certain endocytosis and transcytosis assays, the icosahedral phage are better supports for compounds being screened for activity as potential substrates for receptor-type transport proteins then other phage types. While not intending to be bound by any particular theory and while the utility of such phage does not depend upon the particular reason for the observed improvement, the results indicate that icosahedral phage may be better accommodated or more efficiently transferred in the vesicles that are formed during transport in receptor-mediated systems.

In some instances, the compounds on the icosahedral phage that are to be screened are expressed polypeptides that are displayed as a fusion protein with a capsid protein of the phage; such phage can be prepared utilizing conventional phage display technology in which a library of nucleic acids are inserted into a phage genome to express polypeptide libraries that are fused to a capsid protein. In other instances, however, the compounds to be screened are synthesized independently of the phage and subsequently attached to preformed phage. Still other compounds are directly synthesized on the phage.

There are several challenges to developing phage that display compounds other than expressed polypeptides. First, with such compounds the host bacterial cell or the phage itself can no longer be relied upon to synthesize the library. This means that methods must be developed in which compounds are either synthesized separately and then attached to phage or synthesized directly on the phage. The conjugation method utilized should not interfere with the infectivity of the phage particle, as this is important to its amplification. Secondly, the attachment process needs to be conducted in such a way such that the particular compound(s) borne by any given phage can be determined.

For icosahedral phage displaying an expressed polypeptide, one can identify a displayed polypeptide that has activity by determining the sequence of the heterologous nucleic acid encoding the expressed polypeptide according to established methods. For phage displaying a compound other than an expressed polypeptide, the compound displayed on an phage showing a desired activity can be addressed in a variety of ways.

One option is to analyze the displayed compound itself utilizing any of a variety of known analytical techniques to determine the identity, or at least a distinguishing characteristic, of the displayed compound. Another option is to conduct the attachment process in such a manner that a clonal isolate of a phage receives a distinct compound or pool of compound, and a correspondence regime is preserved indicating which isolate receives which compound(s). In other methods, each phage has a nucleic acid tag that serves to record at least one characteristic of a compound or pool of compounds attached to a clonal isolate of the phage. Usually such a tag is a nucleic acid segment other than a segment that encodes for a polypeptide (or portion thereof) displayed by the phage. With this approach, after attachment of compounds to a phage, the different clonal isolates can be pooled for screening, and the identity of compounds determined from the tags. In some instances, a 1:1 correlation between individual members of the compound library and unique clonal isolates is established using tags. This allows for the unique DNA sequence of individual phage clones to ultimately identify lead compounds with activity in a given assay. In still other methods, the phage within a library lack tags, and phage are tracked by separate screening of different clonal isolates. However, in certain methods even phage lacking tags are pooled. Pools showing activity are subjected to another round of screening to determine which compound borne by one of the phage in an active pool is responsible for the observed activity.

The utility of the icosahedral compound-displaying phage described herein is not limited to just endocytosis and transcytosis screening applications. The phage can be used in a variety of different screening methods to identify compounds with other desired biological activities. For example, the compound-displaying icosahedral phage can be used to identify library members capable of: 1) binding to a receptor, 2) functioning as a substrate or inhibitor of an enzyme, 3) killing bacteria, fungi or other microorganisms, 4) triggering signal transduction and 5) agonizing or antagonizing a receptor. The phage described herein are capable of displaying multiple copies of a single compound (i.e., multivalent display) or single or multiple copies of multiple compounds, thereby facilitating identification of compounds that bind with low-affinity to the receptor.

Initial rounds of screening can be followed with more refined screening rounds. For example, subsequent screening tests can be performed using compounds related to a lead compound identified during initial rounds of screening to identify compounds that have activity that exceeds that of the lead compound. Additional screening can also be performed on compounds in free form or attached to a moiety other than a phage. Moieties screened can include compounds that complement the activity of the active compound or particles that bear or encapsulate other desired compounds.

III. Display Systems

A. General

In the screening methods disclosed herein, a variety of phage types can be utilized to display essentially any compound including an expressed polypeptide or a compound other than an expressed polypeptide. However, as noted above, icosahedral phage are preferred in certain applications, particularly assays designed to identify compound-bearing phage that are taken up into or transported through a cell. The compounds displayed by such phage are potential substrates of a transporter protein. Compounds showing potential as substrates can then be linked to other agents such as pharmaceutical compounds or supports bearing pharmaceutical compounds to achieve selected transport of the pharmaceutical agent to or through certain target cells.

Some of the phage display expressed polypeptides in which a polypeptide encoded by a heterologous sequence of the phage is expressed as a fusion protein with a capsid protein. Other phage, however, display compounds other than expressed polypeptides, such as small organic molecules. Certain phage display polypeptides in which the polypeptide is attached to a phage via a peptide bond, whereas peptides in other phage are attached via a bond other than a peptide bond. As shown in FIG. 1, the compound-bearing phage can include one or more linkers for attaching the compound to the phage. However, as described further infra, some phage are directly conjugated to the compound(s) they bear.

When linkers are utilized, in some instances one linker is either attached to the exterior surface of the phage or a linkage site on the compound. In other instances, two linkers are utilized—one linker being attached to the exterior surface of the phage and the second linker attached to the compound. The interaction between the two linkers acts to join the compound to the phage. In still other instances, one or more bridging linkers can be utilized to effectuate the association between a phage linker and a compound linker. Such an arrangement is useful, for example, for extending the distance between the compound and the surface of the phage. This arrangement minimizes unfavorable steric interactions between the compound and the phage. Any of these linkers can be a reversible linker that can be cleaved, thereby providing a mechanism for the release of compound from a phage. As described in greater detail below, the phage provided herein can also optionally include a tag that encodes for the identity or a characteristic of the compound(s) borne by the phage, thus providing a means for identifying the compound(s) attached to phage found to be active in an assay. In the specific example illustrated in FIG. 1, the linker attached to the phage is streptavidin and the linker borne by the compound is biotin.

Collections or libraries of phage, particularly icosahedral phage, are also provided, with different phage displaying different compounds. Typically, such collections includes at least 3, 4, 5, 6, 7, 8 or 9 phage. Typically, the libraries include at least 10, 20, 30, 40, 50, 60, 70, 80 or 90 members, or any integral number therebetween. In some instances, the libraries include 10, $10^2$, $10^3$, $10^4$, or $10^5$ members or any integral number of members therebetween. Still other libraries contain at least $10^6$, $10^7$, $10^8$, $10^9$, $10^{10}$ or more members or any integral number of members therebetween. Each phage in the collection can display multiple copies of the compound attached to it. In such libraries, the compounds attached to members of the library differ. For example, in some libraries different members of the collection bear different compounds from a combinatorial library. In certain libraries, each phage bears a different compound and harbors a different tag, such that there is a 1:1 correspondence between compound and tag. In other libraries, the same tag can encode for several compounds.

B. Types of Phage

Icosahedral phage are typically utilized in the assay methods disclosed herein, particularly in transcytosis and endocytosis screening assays in view of the improved assay results possible with such phage relative to other types of phage. While icosahedral phage are preferred, the term icosahedral phage can include phage having spherical or pseudo spherical shapes. Specific examples of icosahedral phage include the T odd (e.g., T3, T5 and T7 phage) and T even phage (e.g., T 4 and T6). Examples of spherical and pseudo spherical phage include phix174, ms2, m1 and P2 and P4. Viruses having roughly spherical shapes can also be utilized such as SV40, for example. However, while icosahedral phage are preferred, filamentous phage (e.g., M13, fd and fl) and phagemid vectors derived therefrom can also be utilized in less preferred embodiments. For a discussion of filamentous phage see, e.g., Dower, WO 91/19818; Devlin, WO 91/18989; MacCafferty, WO 92/01047; Huse, WO 92/06204; Kang, WO 92/18619.

C. Library Compounds

1. Types

As indicated supra, the compound displayed by an icosahedral phage can be an expressed polypeptide. In other instances, the compound is a protein but is not an expressed polypeptide. In such situations, the protein can be attached by a peptide linkage (i.e., the amide bond formed as part of the protein backbone), while other proteins are attached via another type of linkage. Certain of these compounds include amino acids that are not included in naturally occurring proteins. The compounds can be of a variety of chemical types including, but not limited to, sterols, nucleic acids, derivatives of purine and pyrimidine bases, β-lactams, aromatic compounds, heterocyclic compounds, carbocyclic compounds, oligo-N-substituted glycines, polycarbamates, oligosaccharides, lipids and amino acids, and derivatives and combinations thereof. In some instances, the compounds are small molecules produced by organic synthesis. Such small molecules can be attached to a polypeptide expressed by the phage.

Compounds are often synthesized independently of the phage to which compounds are to be attached, but can also be synthesized on the phage itself in some instances. Thus, compounds can be synthesized by conventional methods of combinatorial synthesis as summarized below. Such methods are subdivided into nonencoded and encoded methods. In the latter methods, compounds are synthesized on particles that also bear synthesis tags. Such synthesis tags are distinct from the tag, if any, contained in the phage.

2. Non-Encoded Compound Libraries

Libraries of compounds are usually synthesized by solid phase chemistry on a support (e.g., a bead or particle). However, solution-phase library synthesis can also be useful. Strategies for combinatorial synthesis are described, for example, by Dolle and Nelson (*J. Combinatorial Chemistry* 1: 235-282 (1999) incorporated by reference in its entirety for all purposes). Synthesis is typically performed in a cyclic fashion with a different monomer or other component being added in each round of synthesis. Some methods are performed by successively fractionating an initial pool. For example, a first round of synthesis is performed on all supports. The supports are then divided into two pools and separate synthesis reactions are performed on each pool. The two pools are then further divided, each into a further two pools and so forth.

Other methods employ both splitting and repooling. For example, after an initial round of synthesis, a pool of compounds is split into two for separate syntheses in a second round. Thereafter, aliquots from the separate pools are recombined for a third round of synthesis. Split and pool methods result in a pool of mixed compounds. The size of libraries generated by such methods can vary from 2 different compounds to $10^2$, $10^4$, $10^6$, $10^8$, $10^{10}$, $10^{12}$ or $10^{15}$, or any range therebetween. If the synthesis is conducted on a support such as a bead, then the compounds are typically cleaved from the supports and individual library compounds stored separately.

3. Encoded Compound Libraries

An encoded library is one in which a synthesis tag is formed during the synthesis of the library compounds. This synthesis tag encodes at least one step in the synthesis of the library compound. An advantage of this approach is that the synthesis tag is designed to be easily decoded, thus permitting facile identification of the compound corresponding to the synthesis tag. Hence, the structure of the compound can be deduced from the synthesis tag rather than having to determine the structure of the compound directly, which, depending upon the type of compound, can be arduous and time consuming.

Preparation of encoded libraries is discussed in a variety of publications including Needels, et al. *Proc. Natl. Acad. Sci. USA*, 90: 10700 (1993); Ni, et al *J. Med. Chem.*, 39:1601 (1996); WO 95/12608, WO 93/06121, WO 94/08051, WO 95/35503 and WO 95/30642 (each of which is incorporated herein by reference in its entirety for all purposes). Methods for synthesizing encoded libraries typically involve a random combinatorial approach and the chemical and/or enzymatic assembly of monomer units. For example, the method typically includes steps of: (a) apportioning a plurality of solid supports among a plurality of reaction vessels; (b) coupling to the supports in each reaction vessel a first monomer and a first synthesis tag using different first monomer and synthesis tag combinations in each different reaction vessel; (c) pooling the supports; (d) apportioning the supports among a plurality of reaction vessels; (e) coupling to the first monomer a second monomer and coupling to either the solid support or to the first synthesis tag a second synthesis tag using different second monomer and second synthesis tag combinations in each different reaction vessel; and optionally repeating the coupling and apportioning steps with different tags and different monomers one to twenty or more times. The monomer set can be expanded or contracted from step to step; or the monomer set can be changed completely for the next step (e.g., nucleosides in one step and carbohydrates in another step).

The synthesis tags encode one or more reaction steps taken in synthesizing the test compound. For those compounds wherein the synthesis yields a single product in high yield (e.g., an oligonucleotide synthesis), the synthesis tag explicitly specifies one, and usually all, of the components of the compound and its structure. In some situations, for example, when only a small number of monomer units of an oligomer are varied, it is not necessary to identify all the monomers utilized in the synthesis, but only those monomers which vary among the oligomers. For other syntheses that give variable yields and frequently multiple products (such as regio- and stereoisomeric structures), a mixture of compounds is sometimes obtained on each bead. In such instances, the synthesis tag may not uniquely specify the chemical structure of the synthesized test compound. Instead, the synthesis tag encodes the synthetic protocol (e.g., reagents and reaction conditions) by which a test compound in a library was prepared.

Synthesis tags are selected to have a readily identifiable feature that is, for example, microscopically or otherwise distinguishable in shape, size, mass, charge, or emissions. This recognizable feature may arise from the spectral, chemical, electronic, or magnetic properties of the encoding tag, or from some combination of such properties. Through the use of synthesis tags to record the synthesis pathway that each member of a chemical library has taken, the structure of any chemical in the library can be determined from the synthesis tag.

Nucleic acids and inert hydrocarbons are examples of the type of molecules that have utility as synthesis tags. Nucleic acids by virtue of the different bases and known chemistries regarding their attachment provide a natural and straightforward means for encoding the different synthetic steps. When decoding a nucleotide synthesis tag, several options are available. For example, the synthesis tag can be read directly from the bead by sequencing or hybridization. Alternatively, or in addition, a nucleic acid synthesis tag can be amplified (e.g., by PCR) to facilitate identification. Hydrocarbons provide another useful option, because their identity can readily be determined by a variety of well-known chromatographic techniques, for example, GC and GC/MS. Other options are described in Ohlmeyer et al (*Proc. Natl. Acad. Sci. USA,* 90: 10922-26 (1993); and WO 94/08051, each of which is incorporated herein by reference for all purposes).

The time at which the synthesis tag is attached to the support is not critical. For example, a synthesis tag can be attached immediately before, during, or after a round of monomer addition to compounds or other reaction, so long as such timing is compatible with the type of synthesis tag, modes of attachment, and the chemistries involved in preparing the library compound. The necessary encoding of the synthesis steps can be achieved using a single or multiple synthesis tags.

D. Linkers

1. General

A variety of linkers can be used to join the icosahedral phage and library compounds. Such linkers can be useful in providing distance between the phage and the compound to avoid steric crowding that could prevent a recognition element (e.g., receptor or enzyme) to bind the displayed compound, thus generating a false negative assay result. As used herein, a linker does not include moieties utilized simply to activate for reaction either an endogenous group borne by the phage or an inherent functional group of the compound. When used in reference to a compound, an inherent functional group is one that is part of the compound as synthesized; the term does not include a functional group that is part of an activating group or linker incorporated or added to the synthetic compound. In some instances both the phage and compound bear linkers. The association between such linkers can be either covalent or non-covalent.

2. Phage Linkers

An optional linker can be attached to the exterior surface of the icosahedral phage to facilitate attachment to a library compound. Phage linkers should be capable of forming stable complexes with the exterior surface of the phage, as well as being capable of binding to a library compound (either directly or via a linker attached to the library compound).

As used herein, a phage linker refers to an attachment moiety on the surface of the phage that is not naturally occurring, recognizing that there can be some variation in expressed polypeptides that are displayed on the surface of different phage due to natural genetic variability in the phage. Thus, a phage linker encompasses amino acids and expressed polypeptides on the surface that have been derivatized or modified prior to attachment to a compound but not an amino acid or an expressed polypeptide as it exists naturally on the surface of the phage. Such modifications can be introduced chemically, enzymatically or genetically.

One class of phage linkers are those which are members of a binding pair. These linkers bind to compounds bearing the other complementary member of the pair. Certain linkers are expressed polypeptides displayed at the surface that are expressed from an exogenous sequence introduced into the phage. Other peptides that can be used as suitable linkers include, but are not limited to, antibodies, peptide epitopes for antibodies, peptide substrates for enzymes (e.g., BirA and various kinases) and streptavidin. Other suitable phage linkers include, for example, biotin and gold particles.

3. Compound Linkers

Compounds can be attached to the phage through an inherent functional group or via an optional linker. In general, the compound linker is selected to have functionality that can react with or bind to a functional group on the phage or linker attached thereto. If a pool of compounds (e.g., from a combinatorial library) is to be attached to phage, each compound can include the same linker to permit all the conjugation reactions to be performed under similar reaction conditions.

When compounds are to be attached to phage that bear one member of a binding pair at their surface, then the compounds are attached to the second member of the binding pair. Compounds and phage thus become attached through complementary binding pair members. Thus, for example, if the phage includes a ligand-binding protein on the surface (e.g., streptavidin), the linker borne by the compound includes a ligand that binds specifically to the binding protein (e.g., biotin).

One or more additional bridging linkers can be used to increase the distance between the compound and the linker that ultimately becomes attached to the phage. Such a linker is typically bifunctional (i.e., the linker contains a functional group at each end; one group is reactive with a functional group on the library compound, the second group being reactive with a functional group on the linker that binds to the phage). The functional groups at each end can be the same or different. Examples of suitable linkers include straight or branched-chain carbon linkers, heterocyclic linkers and peptide linkers.

4. Reversible Linkers

Any of the foregoing linkers can be reversible linkers that can be readily cleaved under the appropriate conditions, thereby providing a facile way to release a compound from the phage. This capability is important in some assays. NVOC (6-nitroveratryl-oxycarbonyl) linkers and other NVOC-related linkers are examples of suitable photochemical linkers (see, e.g., WO 90/15070 and WO 92/10092), as are nucleic acids with one or more restriction sites, or peptides with protease cleavage sites (see, e.g., U.S. Pat. No. 5,382,513). For cleavage during use, one selects a linker that is spontaneously cleaved under the conditions of the relevant assay (usually a physiological buffer).

Other exemplary linkers that can be employed are available from Pierce Chemical Company in Rockford, Ill.; suitable linkers are also described in EPA 188,256; U.S. Pat. Nos. 4,671,958; 4,659,839; 4,414,148; 4,669,784; 4,680, 338, 4,569, 789 and 4,589,071; and in Eggenweiler, H. M, *Drug Discovery Today*, 3: 552 (1998), each of which is incorporated in its entirety for all purposes.

E. Tags

The icosahedral phage provided herein optionally include a tag for use in identifying the library compound attached to the phage. For icosahedral phage displaying expressed polypeptides, the tag usually is the heterologous nucleic acid segment that encodes for the expressed polypeptide. For phage that display a compound other than an expressed polypeptide, the tag is also usually a heterologous nucleic acid sequence that is inserted into the nucleic acid or genome of the phage or a separate vector harbored by the phage. However, in general (but not always) the tags are not expressed as mRNA or expressed polypeptides. Thus, the tag typically is a heterologous nucleic acid segment other than a segment that encodes for a polypeptide displayed on the phage. The heterologous sequence is sufficiently long to encode whatever information one seeks to record about a compound. Furthermore, the code used normally is not the usual genetic code, i.e., the standard code in which a triplet of nucleotides encodes for an amino acid. Certain codes are simply used to indicate a symbol or value associated with a particular compound. In such instances, all that is necessary is that different phage harbor different tags, and that there is a different phage available for each different compound or pool of compounds to be screened. Other codes are selected to record a particular structural step in the synthesis of a compound, while other codes are used to record one or more components of a compound. In other instances, the code can be used to record the complete structural identity of a compound.

The heterologous sequence can be flanked by other heterologous sequences that facilitate analysis of the heterologous sequence. For example, the heterologous sequence can be flanked with unique primer binding sites. In some methods, the heterologous sequence is flanked by a heterologous promoter (e.g., phage T7 promoter, T3 promoter and sp6 promoter) and a heterologous restriction site, thereby facilitating production of short transcript probes comprising or complementary to the heterologous sequence. In such instances, the heterologous sequence is sufficiently long so that a probe transcribed from the heterologous sequence can specifically hybridize with a complementary sequence under stringent conditions. For examples, lengths of 15 to 30 bases are suitable, although longer sequences can be used. Additional details regarding tags are set forth in the screening section below and in Example 2.

When screens are conducted with phage that harbor sequences that allow for probe formation, hybridization analyses conducted with such probes can be facilitated using isothermal tags. Isothermal tags refer to nucleic acid sequences that have the same base composition but which differ in the ordering of the bases. Because they have the same overall base composition, isothermal tags have the same melting temperature. Consequently, the hybridization and washes conducted during hybridization analyses with the different probes can be conducted under the same conditions, thereby significantly simplifying the screening process.

F. Optional Labels/Reporters

The phage itself can serve as a label since the phage can be readily amplified, thus allowing for sensitive detection. Thus, one can simply collect a sample potentially containing phage that have undergone endocytosis or transcytosis, amplify phage within the sample and then detect such phage by their ability to form plaques on a lawn of bacteria.

However, as a further aid to detection, the icosahedral phage can also optionally include a label/reporter. The label can be any detectable agent that can be attached to, or incorporated within, a phage. Examples of such agents include, but are not limited to, fluorophores, chromophores, radioisotopes, magnetic particles, electron dense reagents, enzyme substrates, enzyme cofactors, enzymes, and chemiluminescent agents. If the phage are labeled, often they are labeled with a fluorophore because a number of instruments for measuring fluorescence are commercially available.

One challenge in assaying for endocytosis is to distinguish between phage that are effectively transported into a cell from phage that are not transported but instead are bound to an exterior of a cell. A variety of methods for making such distinctions are described in detail in copending and commonly owned U.S. patent application Ser. No. 09/661,927, filed Sep. 14, 2000, and corresponding PCT application having International application number PCT/US00/25439, also filed Sep. 14, 2000, both of which are incorporated herein by reference in their entirety for all purposes. One useful way of screening for bona fide transporter substrates is to incorporate conditional reporter groups into potential substrate molecules. The conditional reporter is a moiety that preferentially produces a detectable signal upon uptake by a transporter-expressing cell. In some instances, the conditional moiety can act without having to be cleaved from a phage; in other instances, the conditional moiety must be chemically or enzymatically cleaved before it can generate a signal. Further details regarding this particular strategy, as well as labeling options in general, are described in the U.S. and PCT applications just listed.

IV. Methods of Preparing Compound-Displaying Phage

The method utilized to prepare the compound-displaying icosahedral phage depends upon the type of compound that is displayed. Phage that display expressed polypeptides can be prepared by conventional phage display technology. However, phage displaying compounds other than expressed polypeptides cannot be prepared in this manner. Instead, the compounds must be separately synthesized and then attached to the phage or synthesized directly on the phage. Methods for preparing phage displaying all these different types of compounds are described in the following sections.

A. Preparation of Phage that Display Expressed Polypeptides

Methods for preparing phage that display expressed polypeptides generally involve the insertion of random polynucleotides into a phage genome such that they direct a bacterial host to express polypeptide libraries fused to phage coat proteins. Incorporation of the fusion proteins into the mature phage coat results in the polypeptide encoded by the heterologous sequence being displayed on the exterior surface of the phage, while the heterologous sequence encoding the polypeptide resides within the phage particle. With icosahedral phage such as T7 phage, the heterologous polynucleotide is typically inserted near or at the 3' end of a gene encoding a coat protein.

The size of the polypeptide displayed on the phage can vary and is controlled by the size of the heterologous sequence inserted into the genome of the phage. In general, the displayed polypeptides are of a size that can be displayed on icosahedral phage and can be from just a few amino acid residues or up to the full length expression product of a cDNA. In some instances, the polypeptide includes at least 4, 5 or 6 amino acid residues and less than 100 residues, but other sized polypeptides can be displayed. In some instances, the displayed polypeptides are 10, 20, 30, 40, 50, 60, 70, 80, 90 or 100 residues in length, or any integral number of amino acids within these ranges. Typically, the displayed polypeptide includes 6 to 20 amino acids. The phage can also display random populations of polypeptides. Such libraries are typically designed to produce phage that display polypeptides in which some or all of the positions of the polypeptide are systematically varied for the different amino acids. Random peptide coding sequences can be formed by cloning and expression of randomly-generated mixtures of nucleic acids in the appropriate recombinant vectors (see, e.g., Oliphant et al. (1986) Gene 44:177-183).

Methods for generating libraries of expressed polypeptides on phage are discussed in a variety of sources, including for example, Cwirla, et al., Proc. Natl. Acad. Sci. USA 87:6378-6382 (1990); Devlin, et al., Science 249:404-406 (1990), Scott & Smith, Science 249:386-388 (1990); and Ladner, et al., U.S. Pat. No. 5,571,698, each of which is incorporated herein by reference in its entirety.

B. Attaching Compounds and Phage—Direct Chemical Attachment

Compounds and phage can be directly conjugated through the reaction of an endogenous functional group that appears on the surface of the phage and a functional group inherent to the compound. Typically, the reaction between such functional groups generates a covalent bond. Thus, as defined herein, direct chemical attachment refers to an attachment in which an endogenous group is joined to an inherent functional group borne by the compound. A covalent bond formed from such an interaction includes only atoms from the endogenous group on the phage and the inherent functional group of the compound.

The exterior surface of the phage allows for direct chemical attachment because it typically includes various functional groups to which the compound can be attached. For example, the exterior surface generally includes expressed polypeptides that present amino, hydroxyl, carboxyl and thiol groups which can serve as points of attachment.

The objective in direct coupling approaches is to develop chemical approaches that are compatible with the synthesis of large and structurally diverse small molecule libraries. As such, the methods should have an appropriate level of specificity to effect conjugation to phage in a controlled fashion, yet maintain enough generality so as not to obviate the use of a variety of synthetic chemistry methods during library construction. Chemical ligation strategies that utilize the chemical functionality already present at the exterior surface of phage are attractive because of the general utility of the methods.

Examples of suitable direct attachment methods are illustrated in FIGS. 2A-2D which illustrates the conjugation of small molecules bearing the appropriate functionality directly to residues within a phage coat protein. These include the acylation of lysine residues and free amino termini with an N-hydroxysuccinimide ester, use of carbodiimide chemistry to create an amide linkage between glutamate and aspartate residues or between free carboxy termini within the phage coat expressed protein and small molecules containing amines, and alkylation of cysteine residues with maleimide or iodoacetamide functional groups.

B. Attaching Compounds and Phage—Attachment Via Linkers

Instead of being directly conjugated, phage and compounds can be attached via one or more linkers. The linkers can be useful for introducing certain functionality that facilitates the attachment process or can be used to obtain separation between compound and phage.

1. Formation and Attachment of Phage Linker with Chemical Methods

One option for chemically attaching a compound to a phage involves the chemical formation of the linker or an attachment site at the exterior surface of the phage. This can be done, for example, by derivatizing or modifying an endogenous functional group located at the exterior surface of the phage. Typically, the exterior surface of a phage includes a number of suitable functional groups. For example, the exterior surface generally includes expressed polypeptides that present amino, hydroxyl, thiol and carboxyl groups that can be derivatized or modified. Some modifications involve chemically modifying amino acids or segments of expressed polypeptides at the surface of the phage.

Figure 3A:
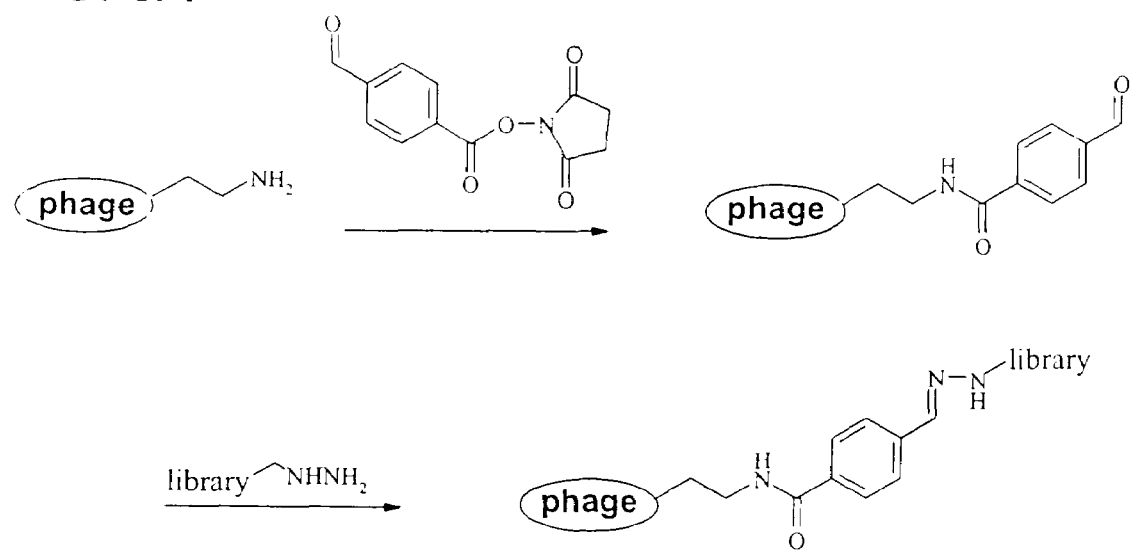
FIGS. 3A-3B depict strategies to effect the chemical conjugation of small molecule libraries to modified phage coat proteins.
Figure 3B:
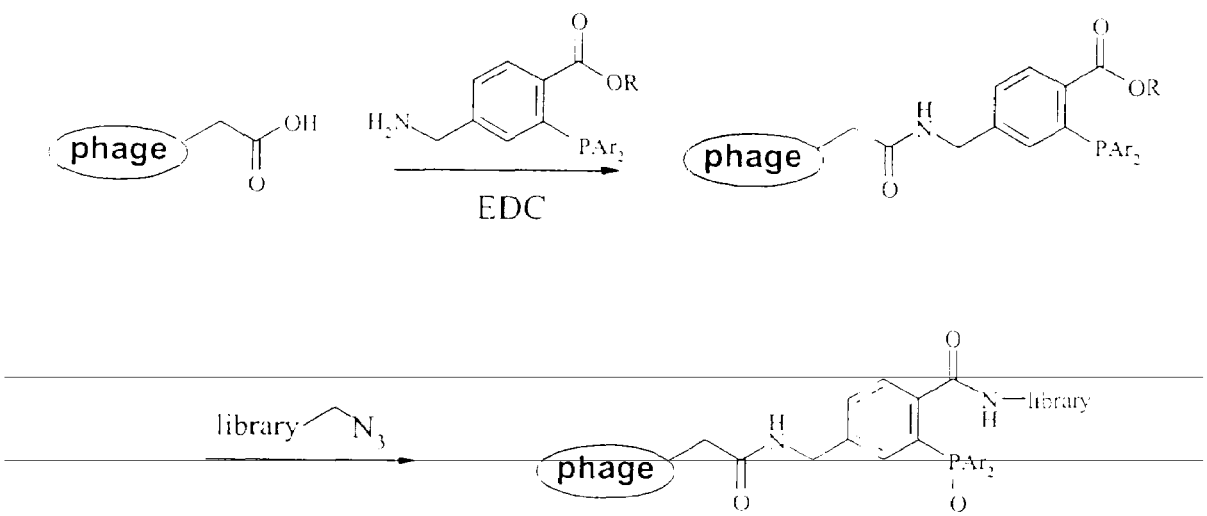

Specific examples illustrating this approach are shown in FIGS. 3A and 3B. These include displaying an aldehyde on the surface of phage, which undergoes a highly specific condensation with hydrazines, hydrazides, semi-carbazides and alkoxy amines to create a stable hydrazone or oxime linkage. In addition, the phage surface can be modified with an aryl phosphine that can condense with azides on compounds to form a highly stable amide linkage.

Instead of modifying an endogenous functional group, other conjugation methods involve chemically attaching a linker to an endogenous functional group borne by the phage. Phage bearing the linker can subsequently be attached to compounds via the linker. As a specific example of this general approach, phage particles are reacted with an excess of NHS-biotin, which forms covalent bonds with free amine groups on the surface of the phage. The biotin on the exterior surface is then reacted with an excess of streptavidin to form a biotin/streptavidin complex. Unbound streptavidin is washed away before reacting the phage with a library member. The library member in this instance includes a biotin linker for attachment to the streptavidin/biotin complex formed on the surface of the phage. Methods involving the chemical attachment of biotin to icosahedral phage are described further in Example 8 infra. Another alternative is to react an antibody with an appropriately activated functional group with the free amine on the surface of the phage. The antibody on the exterior surface of the phage can then be linked to a library compound including a hapten that has specific binding affinity for the antibody.

Figure 4:
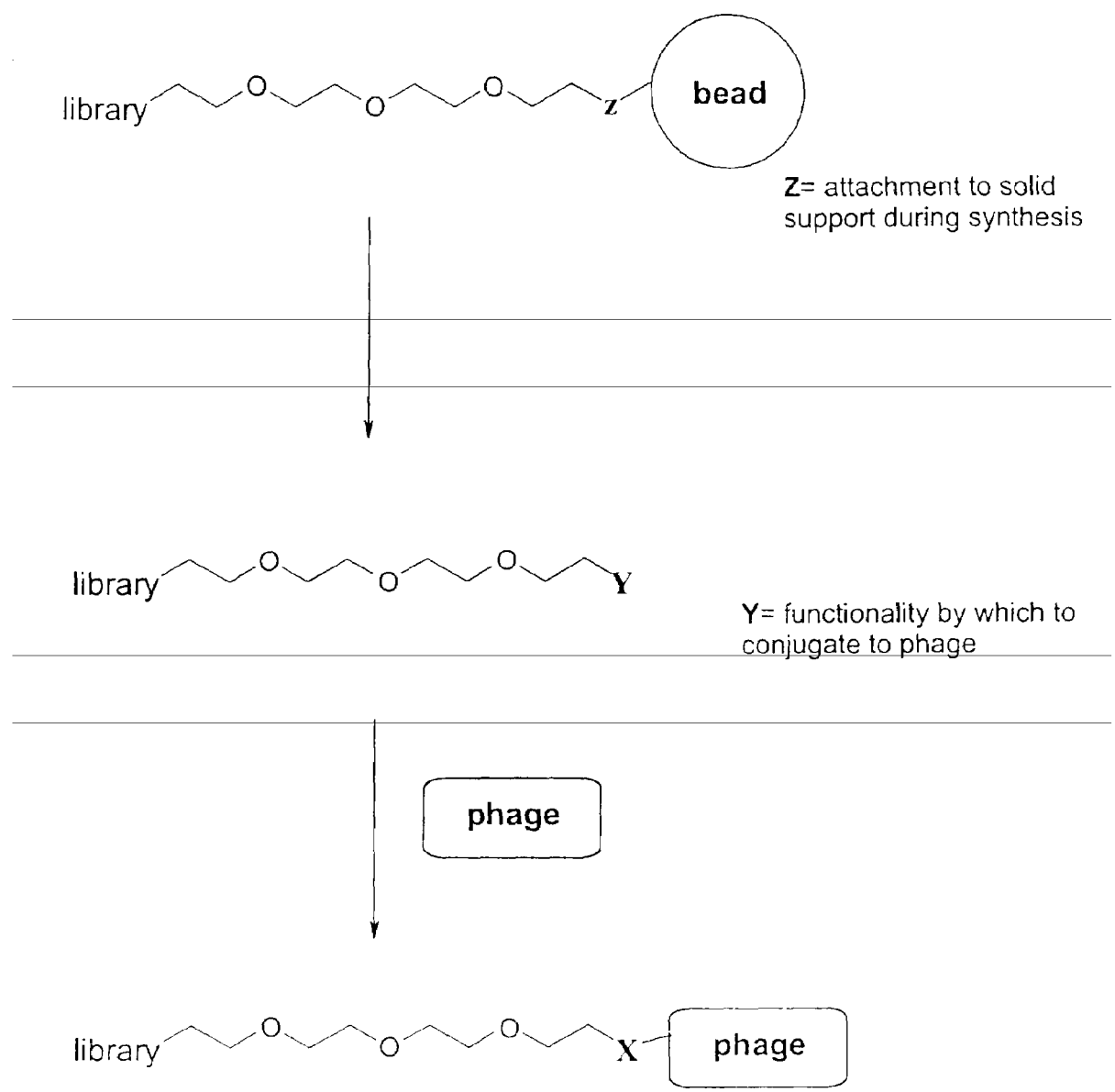
FIG. 4 illustrates a strategy utilizing solid phase attachment chemistry to access functionality to conjugate small molecule libraries to phage.
Figure 5:
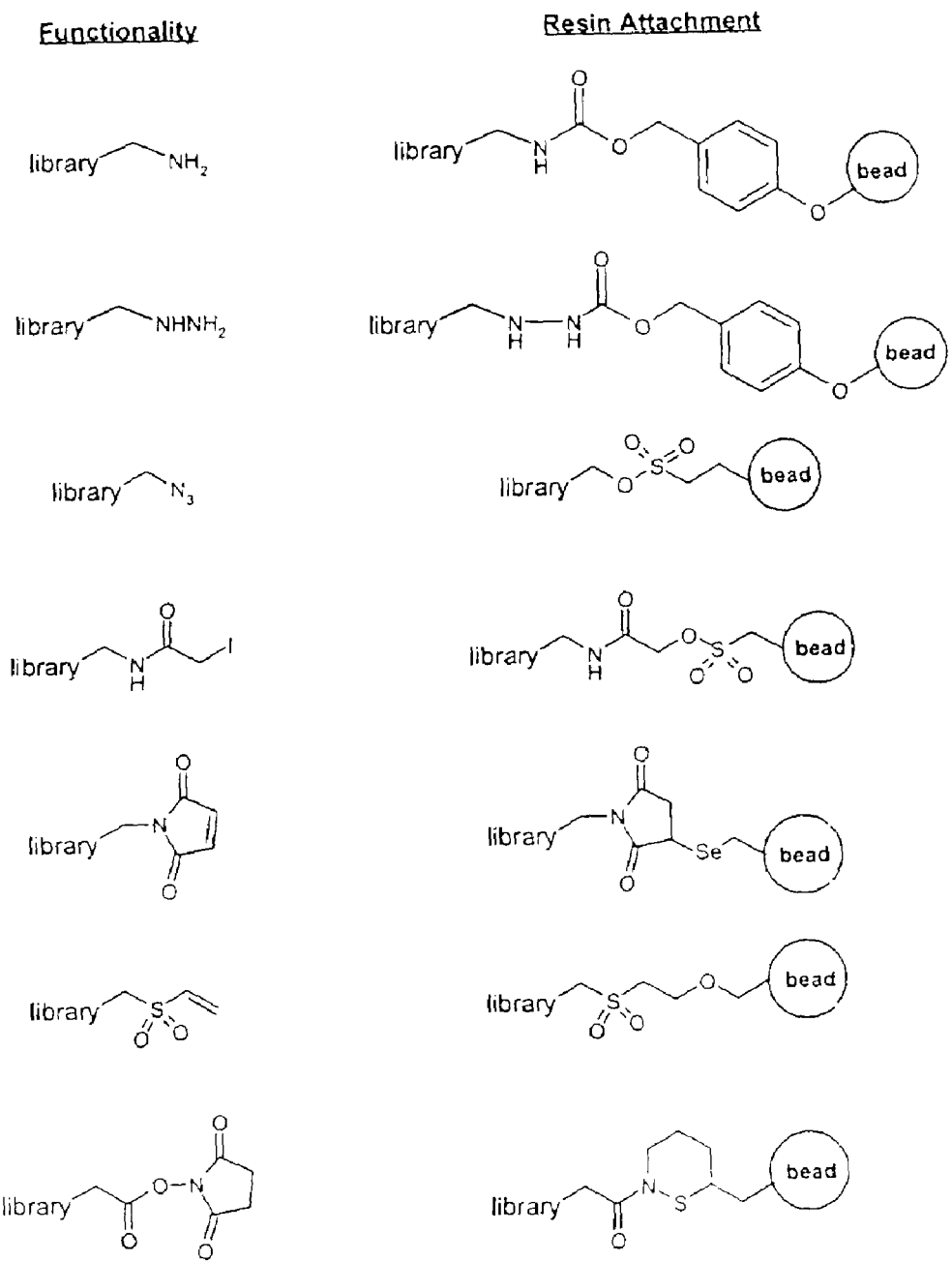
FIG. 5 illustrates strategies to access phage attachment functionality upon cleavage from a solid support.

Other chemical approaches involve the attachment of a compound to an endogenous functional group on the phage via a linker borne by the compound. In such instances, a functional group of the compound linker reacts with a functional group on the surface of the phage. To increase the efficiency of the process of synthesizing small molecule libraries and their subsequent attachment to a phage, the linker utilized to immobilize the compound during synthesis is preferably selected such that the linker can also be used in the attachment of the final compound to the phage. In particular, the functionality by which small molecule libraries are tethered to a solid support should also serve as a site of attachment between the small molecules and the phage. This strategy is outlined in FIG. 4. As illustrated in this figure, the functionality represented by the letter Z, utilized to attach the libraries to solid support, is transformed into functionality Y upon cleavage from the support. Functionality Y is then utilized to chemically ligate the small molecules to phage. Specific examples further illustrating this strategy are shown in FIG. 5, demonstrating how some of the attachment chemistries might be accessed upon cleavage of the small molecules from solid support.

2. Formation and Attachment of Phage Linker with Non-Chemical Methods a. General Instead of chemically attaching a linker to the exterior surface of the phage, the linker can be attached using recombinant and/or enzymatic methods. One approach is to enzymatically convert or modify an amino acid or expressed polypeptide displayed at the surface of the phage to form an attachment site. Various recombinant methods can also be utilized. For instance, with T7 phage, DNA encoding a protein linker can be cloned into the 3' end of the gene for one of the phage coat proteins that is contained in the phage genome itself or on a vector, (e.g., a plasmid). Expression of the fusion gene results in a fusion protein that includes the expressed polypeptide encoded by the inserted sequence and the endogenous coat protein; this fusion protein is displayed on the exterior surface of the phage. Because there are multiple copies of each coat protein at the exterior surface of the phage, multiple linkers (and thus multiple compounds) are displayed at the surface.

So long as the linker is not toxic to the host cell, the DNA encoding a protein linker can be directly inserted into the phage genome [as just noted, typically at or near the N-terminus (or at or near the C-terminus depending upon the phage species) of the genes for one of the phage coat proteins]. If toxicity is a concern, then phage engineered to produce a second copy of one of the coat proteins can be utilized. In such vectors, exogenous sequences are inserted into only one of the two copies. Expression of the other copy effectively dilutes the proportion of fusion protein incorporated into phage particles and can be advantageous in reducing selection against polypeptides deleterious to phage growth. In another variation, heterologous polypeptide sequences are cloned into defective phage vectors that encode a phage coat protein, but which are not capable of producing phage particles. These are grown by coinfection with complementary helper phages. Helper phage can also be used to dilute fusion proteins formed from coat protein and expressed polypeptide with wild type copies of coat protein expressed from the helper phage.

b. Covalent Attachment

One specific example of suitable linkers includes the display of enzymes that can be reacted with high affinity inhibitors (typically small molecules) that are incorporated into a complementary linker borne by the compound. The interaction of such inhibitors with the enzyme can be a non-covalent interaction, e.g. as in the interaction of a protease with a transition-state analog inhibitor, or more preferably, can be a permanent covalent interaction, as would be formed by a suicide substrate inhibitor of the enzyme. An example of the latter such interaction is the reaction of the enzyme β-lactamase expressed on the phage with a penicillin sulfone derivative used as the compound linker (see, e.g., Vanwetswinkel et al, *Bioorg. Med. Chem.* 3:907 (1995)).

Figure 6:
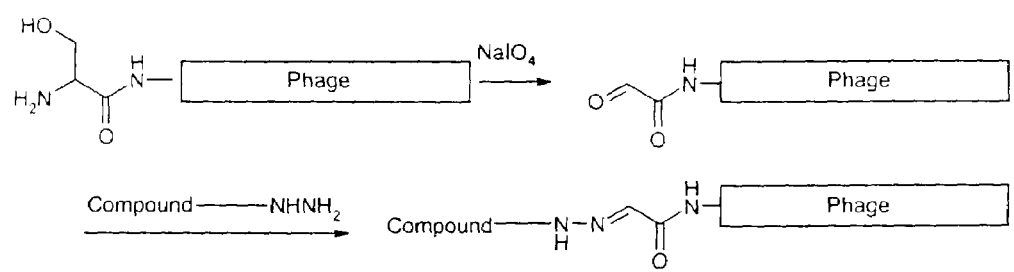
FIG. 6 illustrates one approach for joining a library compound and a phage.

In cases where a free N-terminal residue is available on the selected phage coat protein, a variety of attachment chemistries can be utilized. For instance, in some phage linker/compound linker pairings, the phage linker is an expressed polypeptide fragment that can be chemospecifically reacted under mild reaction conditions with the complementary compound linker. Thus, as shown in FIG. 6, expression of a recombinant phage coat molecule bearing an N-terminal serine residue can be converted by mild treatment with aqueous sodium periodate to a reactive N-terminal glyoxalamide moiety, that undergoes specific reaction with a compound bearing a hydrazine linker (e.g., see Rose, J. Am. Chem. Soc. 1994, 116, 30).

Similarly, as illustrated in FIGS. 7A to 7D phage expressing a recombinant phage coat molecule bearing an N-terminal cysteine residue on the surface can be reacted under mild conditions with various complementary compound linkers to form stable compound-bearing phage. Examples of such compound linkers include, for example: (i) an aromatic ortho-dialdehyde containing compound linker (FIG. 7A), (ii) a mono-aldehyde containing compound linker that reacts with the cysteine residue to form a thiazolidine ligation (FIG. 7B; see Zhang et al, Proc. Natl. Acad. Sci. USA 1998, 95, 9184), and (iii) a benzyl thioester containing compound linker according to the so-called method of "native chemical ligation" (FIG. 7C; see Cotton and Muir, Chem. Biol. 1999, 6, R247).

Figure 7A:
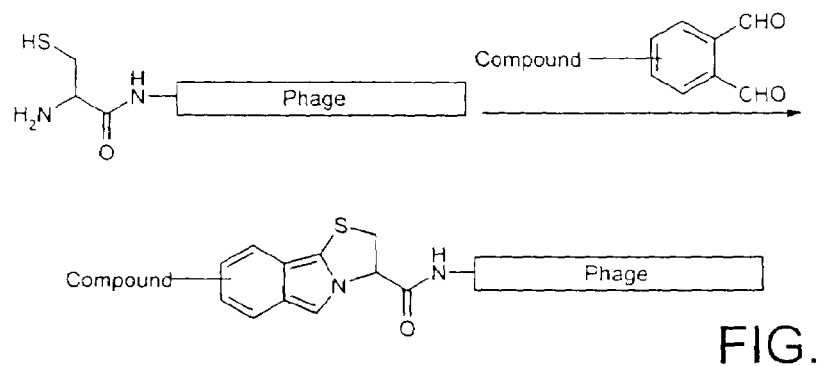
FIGS. 7A-7D illustrate other examples of approaches for joining a library compound a phage.
Figure 7B:
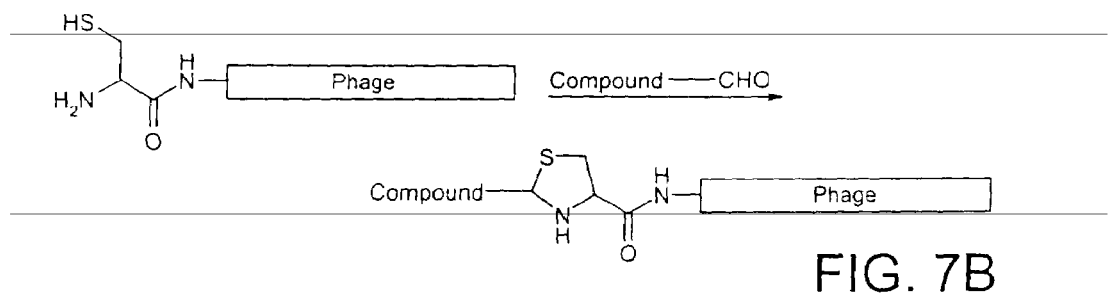
Figure 7C:
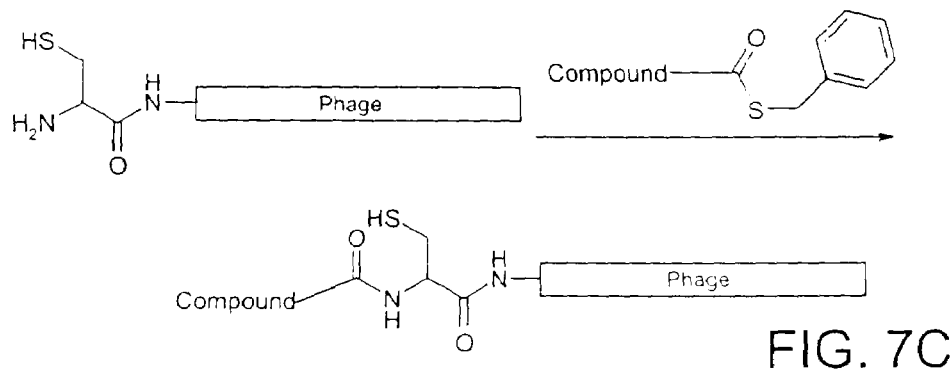
Figure 7D:
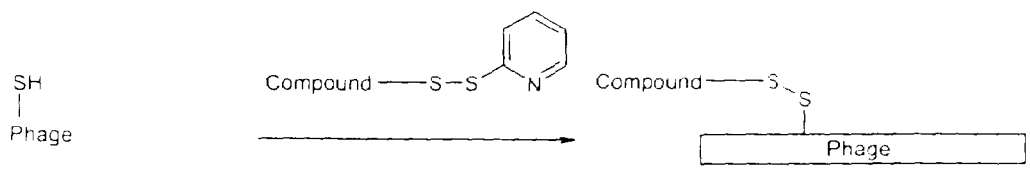

In yet another example involving phage, a phage expressing a recombinant phage coat molecule bearing a free cysteine residue that is accessible anywhere on the protein surface can be chemospecifically reacted under mild conditions with a complementary compound to form a stable compound-bearing phage, such as shown in FIG. 7D.

Certain methods involve combining of peptide display techniques and combinatorial chemistry methods to achieve a superposition of peptide and chemical diversity. Such methods initially involve generating a library of phage that display proteins according to any of the various known peptide display formats such as those described supra. The displayed proteins are subsequently modified by reacting small molecules prepared by synthetic methods to the displayed peptides or by directly synthesizing small molecules on the displayed peptides.

c. Non-Covalent Attachment

In certain recombination methods, the sequence for the protein streptavidin is inserted into the 3' end of the gene for a phage coat protein (e.g., 10 capsid protein) to yield phage displaying multiple copies of streptavidin. Library compounds including a biotin linker can then be joined to the streptavidin linker on the phage (see FIG. 1). Of course, genes for a variety of other proteins can be similarly inserted in place of the gene for streptavidin. For example, the gene for a single chain antibody can be inserted into the coat protein gene to display a fusion protein including the antibody. As described above, such a phage can then be connected to a library compound having a hapten specific for the displayed antibody.

In a related approach, a 16 amino acid artificial biotinylation substrate sequence is cloned into one of the genes for the phage coat protein so that the substrate sequence is displayed at the surface. Phage are then treated with the enzyme Bir A which attaches biotin to a central lysine on each substrate peptide. (See, for example, U.S. Pat. Nos. 5,932,433; 5,922,545; 5,874,239; 5,723,584). Additional details regarding such methods are set forth in Example 2 infra.

In still other methods, the gene inserted encodes for a peptide dimerization domain such that the phage displays the dimerization domain at the surface. The compounds to be attached bear a complementary peptide dimerization domain. With such methods, the compounds and phage become associated through interaction of the dimerization domains. Another approach is to insert the gene for an enzyme into the genome of a phage to achieve display of enzymes at the surface of a phage. These enzymes can react with inhibitors to form stable non-covalent complexes.

Other attachment schemes utilize a particular compound linker to join the phage and the compounds. For example, in one approach, compounds synthesized on a support are cleaved from the support and the resulting individual compounds attached to a large number of very small particles. The particles are then attached to the exterior surface of the phage. The particles used in this approach typically range from approximately 1 to 50 nm, in other instances from 1 to 25 nm, and in still other instances from 5 to 10 nm. Examples of suitable small particles include colloidal gold particles. Given the small size of the particles, this approach enables many library compounds to be attached to the exterior surface of the phage. This is of value when a pool of library compounds is contacted with the phage since the small particles permit a plurality of different compounds to be displayed from the surface of the phage (see below for more details on the pooling approaches).

3. Multivalent Display

Using the foregoing assembly methods, one can prepare phage that display multiple copies of a single compound or multiple copies of multiple compounds. The display of multiple copies of either a single compound or multiple copies of different compounds allows multivalent binding assays to be conducted. Furthermore, such multivalent display enables the screening methods disclosed herein to identify compounds with low activity (e.g., binding affinity). Preparation of phage illustrates this aspect.

The multiple compounds are attached at attachment sites. An attachment site refers to a site that naturally appears on the surface of the phage (i.e., an endogenous site) or to a site that is introduced using chemical, enzymatic or genetic techniques (i.e., an exogenous site) to the surface of the phage. The attachment site allows for non-covalent interaction between the phage and compound or can include functionality that allows for attachment of a compound to the attachment site.

Thus, multiple compounds can be attached by direct chemical attachment as described supra in which a phage and multiple compounds become joined via formation of a covalent bond between an endogenous functional group expressed on the phage and functional groups borne by the compounds. Another option is to derivatize different endogenous functional groups on the phage prior to attaching the compounds. By selectively reacting different functional groups expressed on the surface of the phage with different reagents, one can introduce different attachment sites onto the surface of the phage. Alternatively, different encoding sequences can be inserted into appropriate regions (e.g., 5' region) of the genes for different expressed polypeptides to display different attachment sites on the surface. By displaying more than one type of functional group or expressed polypeptide on the surface in this manner, one can selectively attach different compounds at different locations on a single phage. The display of multiple compounds can be useful, for example, in screening for compounds that both bind to a receptor, potentially resulting in synergistic binding.

Moreover, with phage one can selectively display multiple compounds on particular coat proteins (e.g., phage T7 10 capsid protein). The multiple compounds can be displayed on a single coat protein, or one or more copies of each compound can be displayed on multiple coat proteins that each have the same sequence. Alternatively, one or more compounds can be displayed on each of a plurality of different coat proteins that have different sequences. The multiple compounds that are displayed can be the same or different, allowing for an even greater number of display formats. One way in which compounds can be selectively displayed is to utilize different functional groups on the surface of the phage to control the placement of the compounds. For example, thiols and amino groups on the surface can be selectively attached to different compounds by using compounds that bear functional groups that preferentially react with a particular one of the functional groups displayed by the phage.

In like manner, multiple attachment sites having the same or different chemistry can be selectively utilized to attach compounds at particular coat proteins. For instance, one or more copies of attachment sites having the same functionality may be present or can be introduced into a single coat protein or several coat proteins that each have the same sequence. With other phage, one or more copies of attachment sites having the same functionality are present or introduced in each of a plurality of different coat proteins that have different sequences. Alternatively, one or more copies of attachment sites of differing functionality may be present or can be introduced on one or more coat proteins that share the same sequence. Finally, one or more copies of attachment sites of differing functionality may be present or can be formed at each one of a plurality of coat proteins having different sequences.

4. Phage Immobilization and Release Strategies

The attachment process in some instances is performed by initially immobilizing the phage on a support, typically via a reversible linker that is cleavable. The compound is then attached to the immobilized phage, unreacted compound washed away and the phage displaying the compound released by cleaving the linker. The resulting phage can then be used in assays.

B. Tagging Phage

1. Insertion of Heterologous Sequence to Form a Phase Library

As indicated above, some of the phage provided herein include a tag to facilitate the identification of library compounds that appear from assay results to have a desired characteristic. In some methods, the tag is a heterologous nucleic acid that is inserted into the genome of the phage. In such instances, a degenerate nucleic acid mixture is inserted into a convenient location of the genome of the phage. By inserting a degenerate nucleic acid mixture into a population of phage, a library of phage can be prepared in which each member contains a different heterologous sequence.

While in some methods only a heterologous nucleic acid sequence is inserted into the genomic DNA of the library member, in other methods an inducible promoter and a restriction site are also inserted into the genome. The promoter and restriction site are inserted so that they flank the heterologous nucleic acid; the promoter is also positioned such that it is operably linked to the heterologous nucleic acid. The promoter initiates transcription of the inserted heterologous sequence to produce a probe that lacks upstream phage sequences. By cleaving the DNA at the restriction site prior to transcription, the transcribed probe also lacks downstream phage sequences. Thus, the RNA probe resulting from transcription of the heterologous nucleic acid sequence primarily contains only the sequence unique to a particular phage clone. As described in more detail below, this probe can be utilized to identify those compounds that produce positive assay results.

In preparing clones in this manner, the heterologous nucleic acid, the promoter and the restriction site are all typically inserted at sites that do not create any deleterious effects on the phage, such as non-coding sites for example. One useful site for insertion of the heterologous site is at the C-terminus of the gene for one of the phage coat proteins. If promoters are inserted, suitable promoters include, for example, the phage T7 promoter, the T3 phage promoter and the SP6 phage promoter; the promoter is selected to be heterologous with respect to that phage.

As indicated above, the heterologous sequence is typically 15 to 30 bases long. This length is sufficiently long to ensure that during hybridization reactions the probe generated from the heterologous sequence can specifically hybridize with a complementary sequence, even in complex mixtures. A nucleic acid this long also provides enough sequence complexity ($4^{15}$ to $4^{20}$=30 million to 1 billion members) that large numbers of randomly-picked clones from a population of clones are very unlikely to carry the same (or even similar) sequences.

With certain collections of phage, the heterologous tags inserted into the different phage are selected to be isothermal. As indicated supra, this involves introducing sequences that have the same base composition, thereby resulting in tags that have the same melting temperature.

2. Transformation of Host Cells

The phage library is used to transform host cells so that a population of each clone can be formed. The transformed host cells optionally include a vector such as that described above that includes a fusion gene for a phage coat protein and a protein linker so that the new phage produced through assembly in the host cell display a linker at the surface (alternatively, such a fusion gene can be formed in the phage genome). Infected host cells are plated out as individual colonies. Each colony is picked and separately grown, typically in separate wells on a multi-well plate (e.g., a 864-well plate, each well having a 20 µl volume). Individual colonies can be picked and placed manually or automated using commercially available systems (e.g., QBot). Such systems allow the facile production of 10 to 100 multi-well plates or more. Each colony is grown under suitable conditions for expansion. Bacteria are subsequently removed using standard filtration or centrifugation methods, thus leaving an encoded phage library in the plates—each well of the multi-well plate containing a single clone. Such plates are referred to as "master plates."

A variety of different host cells can be transformed with the phage library members. Examples of suitable host cells include *E. coli* (for specific examples of suitable strains of *E. coli*, see, for example, Peters, et al., J. Bacteriology 176:4296-4305 (1994)).

C. Linking Optional Reporter

Linking a reporter to a phage varies somewhat with the nature of the reporter. The reporter can be attached to the polypeptide (either directly or via a linker) or attached to the surface of the icosahedral phage itself. The exterior surface of the phage allows for direct chemical attachment because it typically includes various functional groups to which the reporter can be attached. For example, the exterior surface of the phage generally includes expressed polypeptides that present amino, hydroxyl, carboxyl and thiol groups which can serve as points of attachment. A label having functionality that is reactive with such groups can be directly bound to these groups. Alternatively, the functional group can be modified or derivatized to form a moiety that is more reactive with a functional group borne by the label. Other methods for conjugating a label onto the phage surface involve joining the label and the phage via a linker. A linker can be utilized to provide greater distance between the phage and the label. This can sometimes be helpful in alleviating steric crowding between the reporter and the displayed polypeptide. Certain linkers include a functional group at each of two ends. The functional group at one end reacts with a functional group on the phage, whereas the other functional group reacts with a functional group on the label.

One specific example of a method of attaching a label via a derivatized functional group on the surface of a phage involves the biotinylation of the exterior surface of the phage. Such an approach involves reacting phage with an excess of NHS-biotin, which forms covalent bonds with free amine groups on the surface of the phage. The biotin on the exterior surface is then reacted with an excess of streptavidin to form a biotin/streptavidin complex. Unbound streptavidin is washed away before reacting the phage with a label. The label in this instance includes a biotin linker for attachment to the streptavidin/biotin complex formed on the surface of the phage. Another option for modifying a functional group is to enzymatically convert or modify an amino acid on the phage or expressed polypeptide to form an attachment site. Various recombinant methods can also be utilized. For instance, with phage, DNA encoding a protein linker can be cloned into the 5' end of the gene for one of the phage coat proteins.

V. Screening Methods—No Tags

A. Establishing a Correspondence Regime

A correspondence regime refers to a system that allows one to keep track of which phage bears which compound so that the identity of a compound showing activity can be identified. A library of compounds to be tested can be formed in the following manner. Phage (often including a first linker attached to the exterior surface of the phage as described above) are placed in an array, typically the wells of a multi-well plate. An individual member from a library of compounds is incubated separately with the phage to form a plurality of phage displaying different compounds other than expressed polypeptides, each well containing a phage that displays a different compound. The compounds can be from a known array such as a parent plate of compounds that have been cleaved from the support (e.g., a bead) upon which they were synthesized; alternatively, the compounds can be compounds severed from stochastically chosen supports, where the supports remain spatially arrayed for future identification.

Instead of contacting phage with a single library compound member, small pools of library compounds can be contacted with the phage, such that each well contains a phage that displays multiple compounds. This significantly increases the efficiency of the screening process. If pools of library compounds are reacted, the pools typically contain less than 10, 25, 50 or 100 different compounds, although larger and smaller pools can also be used. During the contacting step, which compound or pool of compounds is added to each array location is tracked.

Assays can also be conducted using a pool of compound-bearing phage. In such instances, the particular phage pooled are tracked such that phage from a pool showing activity can be individually reassayed to identify the active compound(s) in the pool.

Phage can be designed to display multiple copies of a single compound or compounds per phage by providing multiple binding sites per phage. In instances in which a single compound is added to a group of phage, each phage contains multiple copies of a single compound. When a pool of compounds is attached to a clonal isolate of phage, a single phage in the isolate can display more than one type of compound. An excess of compound is added to the reaction mixture. Typically, approximately $10^6$ to $10^8$ phage are incubated with a large excess of compound(s). The concentration of compounds usually is more than 1 nM, often greater than 1 µM, and sometimes as more or more than 1 mM.

B. Screening

An aliquot of phage displaying a compound or multiple compounds is taken from a location in the array and assayed to determine whether the compound(s) on the phage taken from that particular location have a desired characteristic. The process is sequentially repeated with the phage at the other array locations. Because the location from which an aliquot is taken is noted prior to conducting the assay, it is possible to identify those array locations containing a compound or compounds that have the desired characteristic being assayed for. Since the compound or compounds added to each array location is also known, the identity of the compound can be established. In addition to assay of compounds in arrays, aliquots can be taken from the arrays and mixed for screening.

C. Compound Identification

In sequential methods such as those just described in which each phage contains a single type of compound, the structural identity of the compound can be determined directly if the identify of the compound was ascertained prior to the assay. Even if the identity of the compound was not determined prior to forming the display phage, the compound can be readily identified using standard analytical techniques such as mass spectrometry (MS), gas chromatography-mass spectrometry (GC-MS), infrared spectroscopy (IR), high performance liquid chromatography (HPLC), and/or nuclear magnetic resonance spectroscopy (NMR). If the compound was prepared on a support with a synthesis tag, the tag can be decoded to reveal the structure of the compound.

When pools of compounds are reacted with the phage so that they display different compounds, a subsequent round of screening is necessary to identify those compounds within the group of compounds that have the desired characteristic. For example, because the pool of compounds added to the phage at any array location is known, it is possible to individually reassay each compound in the pool of compounds shown in the initial assay to include at least one compound with the desired characteristic. Thus, for example, if array location 10 contains phage displaying compounds number 50-60 and an aliquot of compound bearing phage from this location produces a positive assay result, compounds 50-60 are individually contacted with phage in separate array locations and then sequentially assayed in a second round of screening to identify which of the eleven compounds have the desired characteristic.

To ensure accuracy in the assay results various controls may be performed in parallel with the assays of the library compounds. For example, as a negative control, assays may be conducted with phage lacking a linker to which a library compound can attach (i.e., the assay is conducted with a phage that lacks a library compound). As a positive control, a compound known to have the characteristic that is being screened for can be displayed from a phage and assayed to ensure that a positive result is obtained.

VI. Screening Assays—with Tags

A. Correspondence Regime

Assays utilizing tags use the master plates described above in which cloned phage are stored in individual locations in an array (e.g., wells of a multi-well plate), each location including a population of cloned phage containing a unique heterologous sequence that encodes for the compound(s) displayed from the phage. Separate aliquots are typically removed from the each of the array locations and individually spotted on a membrane to also form an "archival grid". The archival grids are arrayed such that each spot on the grid can be tracked or correlated with its corresponding location on the master plate. Many such archival grids can be routinely prepared using available automated and robotic spotting technologies.

To associate a clone with a library compound, library compounds are arrayed in separate locations, generally within the wells of a multi-well plate. As indicated above, the compounds may be from a known array such as a parent plate of compounds that have been cleaved from the support (e.g., a bead) upon which they were synthesized; alternatively, the compounds may be compounds severed from stochastically chosen supports, where the supports remain spatially arrayed for future identification.

Aliquots of phage taken from the master plate array are transferred to the wells containing library compounds so that each location in the array contains an aliquot of a single library compound and an aliquot of a unique clone phage. The aliquots are transferred such that the clone phage and library compounds remain spatially segregated and kept in registration with the array that contains the clones. As described above, when the clone phage and library compounds are contacted, a sufficient excess of library molecules is contacted with the clone phage to occupy the desired number of linker sites on the phage.

B. Screening

The compound-bearing phage are then screened as individual entities or, more typically, pooled into complex mixtures for screening. If pools of phage are screened, a subsequent round of screening is performed with individual phage from a pool showing activity to identify which phage in the pool bears the compound responsible for the observed activity. Pooling of aliquots can be performed using convention multichannel pipettors. The resulting compound-bearing phage are then ready to be assayed.

In addition to using pools of phage to increase screening efficiency, the capacity of the screening process can be greatly amplified by reacting each clone phage with a pool of library compounds rather than a single compound. In this way, each phage displays multiple compounds rather than a single compound. As described for the non-tag screening methods, in the pooled compound approach, typically 10, 25, 50 or 100 different compounds are reacted with the clone phage. If a phage displaying different compounds produces a positive assay result, a second round of screening is necessary to identify which of the compounds in the pool have the desired characteristic.

If pools of 10 compounds are reacted with each phage clone and 10,000 phage clones are arrayed in multi-well plates, the method just described can be used to readily screen $10^5$ compounds. Since phage master plates can be used repeatedly, the methods described herein can be easily scaled to allow rapid screening of greater than $10^6$ synthetic compounds.

After an initial round of screening, further enrichment for positive compounds can be achieved through additional rounds of screening. Although amplification of the phage between rounds is typically not done, multiple rounds of screening can be performed to achieve optimal enrichment of positive clones by starting the screening process with excess of each compound-bearing phage. After the final round of screening, positive compound-bearing phage are expanded. In the case of phage, the positive clones are infected into a host such as *E. coli* and plated under selection.

C. Compound Identification

1. Sequencing Tag

If the compound is an expressed polypeptide, then the compound (i.e., the displayed polypeptide) can be readily determined from the heterologous sequence within the phage that encodes for the displayed polypeptide. Various options are available for decoding the tag when the compound displayed is other than an expressed polypeptide. For instance, when the phage contains a heterologous sequence but lacks the other elements necessary to produce a probe from the heterologous sequence, the compound can be identified by sequencing the heterologous nucleic acid inserted into the genome of the clone phage. Sequencing can be done before screening, but usually is done after screening. Sequence determinations can be performed using standard automated sequencing equipment and technologies. Thus, when individual (or small pools of) library compounds are joined to the clone phage, each library compound (or small pool of compounds) becomes associated with a particular known heterologous sequence. Thus, by sequencing the heterologous sequence of compound-bearing phage that give positive assay results, it is possible to unambiguously identify the compound (or pool of compounds) having the desired characteristic. As described above, in pooled approaches, a second round of screening is performed to identify which members of the pool have the desired characteristic.

2. Using Tag to Generate Hybridization Probe

When the clone phage include a promoter and appropriate restriction site to generate a probe, it is not necessary to sequence the heterologous sequence either before the phage are contacted with library compounds or after an assay has been performed. Instead, probes from phage bearing compounds with the desired characteristic are generated, labeled and used to probe the archival grids that contain sample dots for each of the compound-bearing phage that were prepared. Spots containing phage that contain heterologous sequences that specifically hybridize to the labeled probe can be identified from the bound label; it is these phage that display compounds with the desired characteristics. Since the compound or compounds added to any genetic phage is known based upon the correspondence regime described above, the identity of compounds having the desired characteristics can be established. If the structural identity of the compounds was not previously determined, it can be determined using conventional analytical techniques such as those described above (i.e., MS, GC-MS, HPLC and NMR, for example). If the compound was synthesized on a support that included a synthesis tag that encodes at least one step of the synthesis, the synthesis tag can be decoded using the techniques described above to identify the active compound.

The probes can be prepared from individual clones and hybridized as individual clones, prepared from individual clones and then mixed, or prepared in batch. One approach for preparing individual phage clones initially involves picking 100 colonies and inoculating each clone into a 4 ml culture tube for expansion of the clone and growth of the phage. A set of 10 "clone arrays" or "clone grids," are prepared from the phage samples. Each of these is a 10×10 array of the 100 expanded clones. Ten of the clones are chosen for labeled probe preparation. Once labeled, each of the probes is hybridized under the appropriate stringency condition against the clone array to determine the frequency of each clone's appearance in the positive clone picks. Based upon this frequency information, a determination is made regarding the number of positive clones from which probes should be prepared for use in hybridization experiments against the heterologous sequences contained in the compound-bearing phage spotted in the archive grids.

VII. Types of Assays

A variety of different assays can be performed with the compound-displaying phage disclosed herein. As described herein, icosahedral phage have been found by the current inventors to provide enhanced assay results in transcytosis and endocytosis assays. In addition to these advantages, other features of phage in general make them useful in the screening assays disclosed herein. Most notable among these is the ease of quantitation, sensitivity of detection, and ability to incorporate large amounts of information in the nucleic acid or genome of the phage. For example, most phage can be quickly and accurately counted by the process of titering—growing plaques on host cells, each plaque representing a single viral particle from the analyte, and counting the plaques. In principle, the sensitivity of detection is a single phage—considerably more sensitive than other detection schemes. Moreover, detection can usually be accomplished from a dilute and complex medium, such as a tissue fraction. The ability to easily encode additional information in the nucleic acid or genome of the phage allows individual phage to be tracked as each moves through a biological system, a goal that is considerably more difficult to achieve with synthetic particles.

Thus, while icosahedral phage find particular utility in screening assays of substrates for transport processes and in screens for new transport proteins, the phage disclosed herein can be utilized in a number of other assays as well. Examples of such assays are described in the following section.

A. Endocytosis and Transcytosis Assays

1. Background

As set forth above, active transport of compounds into or through cells typically occurs by carrier-mediated systems or receptor-mediated systems. The methods described herein are primarily for assaying receptor-mediated transport systems, as this system is the one primarily involved in endocytosis and transcytosis. All eukaryotic cells undergo a continuous process of vesicle formation at the cytoplasmic side of the plasma membrane. The resulting membrane-enclosed vesicles are of a variety of sizes and compositions, generally of diameters of ~50 to 200 nm, enclosing volumes of roughly $10^{-20}$ to $10^{-17}$ liters ($10^7$ to $10^{10}$ Å$^3$). Following endocytosis, the vesicles are directed to any of a number of cellular locations. The pathway and ultimate destination are directed by a variety of signal motifs present in the cytoplasmic, transmembrane and extracellular domains of the proteins located on the vesicles, and, in some cases, by the non-protein membrane components of the vesicles.

In polarized cells, such as epithelial and endothelial cells, the vesicles may be transported from one side of the cell to the other, a process of transcellular transport known as transcytosis. The vesicle docks and fuses with the plasma membrane and the contents are emptied to the extracellular compartment. Polarized cells in which such transport occurs are present in many tissues. In all epithelial layers, the layers of cells separating the body from the outside world, the cells are polarized. Epithelial cell layers are characterized by the presence of tight junctions that form an effective seal between all the cells of the layer. It is this seal that divides the cells into an apical (outside) and a basal (inside) surface. The areas between the cells on the inside side are lateral; hence, the entire inside surface of the epithelial cell is known as the "baso-lateral" surface. The cytoskeletal structure, which is connected to the sites of the tight junctions, serves as an internal indicator of the orientation of the cell, and provides a signal to guide the proteins and organelles to their appropriate location in the polarized cell.

The foregoing pathways can be utilized for the delivery of foreign materials into or through cells for purposes of therapeutics, diagnostics and intracellular monitoring. Agents that can be delivered by these routes include small molecules, macromolecules, and particles. For delivery of agents by transcytosis, pathways with particular features are chosen. For example, to deliver drugs across the intestinal epithelium, one prefers a pathway with a reasonably high capacity of transport. In the intestine, most of the known pathways directed from apical to basal-lateral (lumen to blood) are of limited capacity and generally not optimal for drug delivery.

The compound-displaying icosahedral phage described herein can be utilized in assaying transport processes, particularly receptor-mediated transport processes. The methods described herein can be utilized to discover novel transport pathways, to identify substrates of receptors mediating transport processes, and to quantitate the capacity for transport of known or novel pathways. The methods are applicable for use in vitro (e.g., with cultured polarized cells), ex vivo with an excised tissue (e.g., an isolated section of small intestine), and in vivo, as might be done in the small intestine of a living animal.

2. Assays to Identify Substrates of Receptor-Mediated Transport Processes

The methods generally involve contacting libraries of icosahedral phage clones displaying many different polypeptides with the targeted cell population under conditions allowing endocytosis/transcytosis to occur. The cells utilized in the assays can be natural cells that express a naturally occurring receptor-mediated transport protein or cells transfected with DNA encoding such receptors. After an appropriate incubation time, the opposite side of the cells or tissue or the compartment of the cell or tissue that serves as the desired destination of the pathways of interest are analyzed for the presence of phage delivered via an endocytosis/transcytosis pathway.

Analyses for transported phage can be performed in a variety of formats. For instance, a sample potentially containing transported phage can be placed on a lawn of host bacteria to produce phage plaques—each plaque representing a single, successfully transported phage particle. Each plaque can be isolated, expanded and the heterologous nucleic acid encoding the displayed polypeptide sequenced to determine the identity of the polypeptide that is a substrate. In the case of a phage displaying an expressed polypeptide, the heterologous nucleic acid is typically the sequence encoding the expressed polypeptide; for phage displaying compounds other than expressed polypeptides, the heterologous nucleic acid is usually the tag described supra. Alternatively, the identity of the displayed polypeptide can be identified by in situ hybridization of a probe that is complementary to the heterologous sequence that encodes the displayed polypeptide. Yet another option is to utilize standard analytical chemical techniques to analyze the displayed polypeptide.

3. Assays to Identify Receptor-Mediated Transport Proteins

In addition to screening for potential substrates of known receptor-mediated transport processes, screens of an expression library of icosahedral phage expressing cell surface proteins can also be conducted to identify new transport proteins, particularly receptor-mediated transport proteins. In these assays, cells expressing a potential receptor-mediated transport protein are contacted with phage that display known substrates or potential substrates. Cells through which phage are transported are identified and the heterologous nucleic acid sequence that encodes for the protein is determined to identify a protein that is a potential receptor-mediated transport protein.

4. Assays with Optional Reporters

Certain methods are conducted with icosahedral phage that bear a reporter capable of generating an optical signal. The reporter can be attached to the displayed compound (either directly or via a linker) or attached to the surface of the phage itself. Detection of the signal at a location that indicates that a phage has passed through a cell indicates that the phage bears a polypeptide that is a substrate for a receptor-mediated transporter protein expressed by the cell.

5. Exemplary In Vitro Assay Methods

Figure 8:
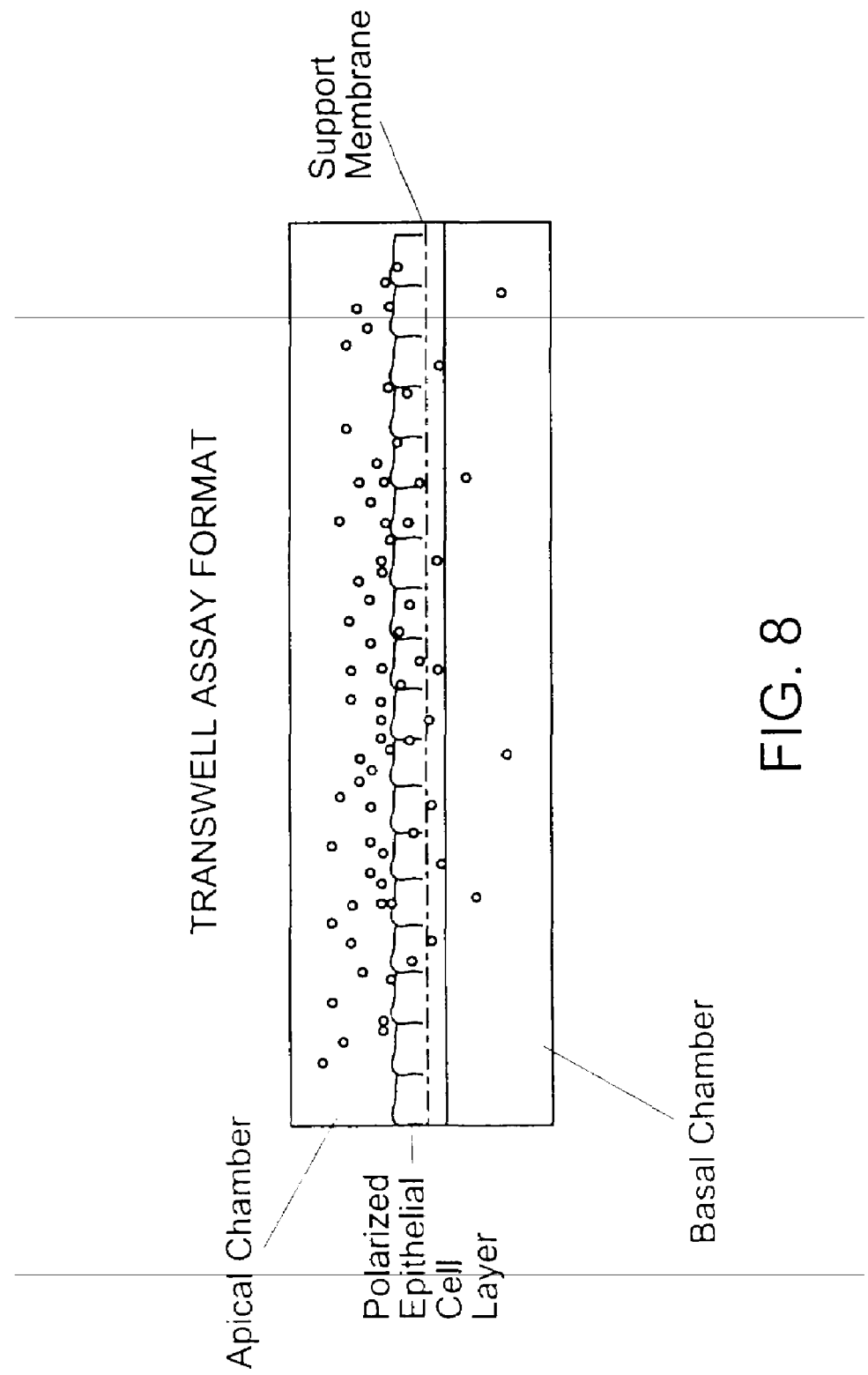
FIG. 8 depicts a membrane system (a transwell) for assaying for transport through a cell.

Assays to Identify Substrates of Receptor-Mediated Transport Processes. One example of a specific assay method designed to screen for compounds capable of being transported through a cell utilizes a support membrane system, sometimes referred to as a transwell (see FIG. 8). The support membrane is a porous membrane that includes pores that are larger than the icosahedral phage display particle being screened. A monolayer of polarized cells (e.g., CaCo-2, HCT-8, T84, HT29 and MDCK cells) is grown on this membrane. A sample containing phage library members is typically applied to the apical side of the polarized cells in the apical chamber. The applied phage are then allowed a period of time to be transported through the monolayer. Passage of a phage through the cell monolayer and the permeable membrane and into the basal chamber can be detected by standard titering protocols that are described in further detail in Example 3.

If the polypeptide-bearing phage also bears a label as described supra, internalization of such a phage can be detected by detecting a signal from within a cell from the reporter. The reporter can be a label such as a fluorophore, a chromophore, a radioisotope, a magnetic particle or an electron dense reagent. The reporter can also be a protein, such as green fluorescent protein or luciferase expressed on the surface of the phage. Confocal imagining can also be used to detect internalization of a phage as it provides sufficient spatial resolution to distinguish between fluorescence on a cell surface and fluorescence within a cell; alternatively, confocal imaging can be used to track the movement of phage over time. In yet another approach, internalization of a phage is detected using a reporter that is a substrate for an enzyme expressed within a cell. Once the phage is internalized, the substrate is metabolized by the enzyme and generates an optical signal that is indicative of uptake. Light emission can be monitored by commercial PMT-based instruments or by CCD-based imaging systems.

Alternatively, movement of icosahedral phage through cells can be monitored using a reporter that is a substrate for an enzyme that is impregnated in a membrane supporting the cells. Passage of a phage bearing such a substrate generates a detectable signal when acted upon by the enzyme in the membrane. This assay can be performed in the reverse format in which the reporter is the enzyme and substrate is impregnated in the membrane.

In another approach, the icosahedral phage bear a reporter that is an activator of a metabolic process in indicator cells. The indicator cells are then impregnated into a membrane supporting a cell monolayer. After passage of a peptide-displaying phage through the monolayer, the reporter induces a metabolic event in the indicator cells that generates a signal in proximity to the cell(s) passing phage. Examples of suitable reporter include a bioactive compound that activates a cell surface receptor and a linked transcriptional promoter installed into the indicating layer of cells. The promoter drives a secondary reporter that can include, for example, an enzyme capable of generating a fluorescent signal, a fluorescent protein such as GFP, or a cell surface marker that can be stained by a fluorescently-labeled ligand or antibody at the cell surface for detection by FACS. Optical alignment of the active reporter cells with the polarized layer of library cells allows identification and recovery of the positive library cells in the layer above the reporter cells.

To further characterize transported phage, cells identified as promoting transcytosis are picked and clonally expanded. The various members of the test polypeptide library are exposed (sequentially) to each of the expanded clones in a transwell format. Each clone transports those phage that belong to a single family; such phage are recovered from the bottom (basal) compartment of the transwell. Phage that are not transported are removed from the top (apical) compartment of the transwell and placed on the next clone of cells, and the process repeated. At the end of this process, the pool of phage recovered from below each cell clone layer represents a population enriched for test polypeptides that are able to direct the transcytosis of an attached particle. This can be a single polypeptide or a group of related (or even non-related) test polypeptides that bind to the specific transport protein that has been cloned and over-expressed by the corresponding clones. By virtue of this enrichment, the test polypeptide can be more easily and reliably identified by techniques described below.

Assays to Identify Receptor-Mediated Transport Proteins. Certain methods are performed with polarized cells that are transformed with DNA that encodes for different proteins that are potential receptor-mediated transport proteins utilizing a two membrane system. The first membrane or upper membrane is a porous membrane that includes pores that are larger than the icosahedral phage display particle being screened; this membrane is located within an apical chamber. A monolayer of polarized cells (e.g., CaCo-2, HCT-8, T84, HT29 and MDCK cells) is placed on this upper membrane. A second or lower non-porous membrane is positioned under the first membrane and is structured to retain any phage capable of traveling through the polarized cells and through the pores in the upper membrane. This membrane is part of a basal chamber. A sample containing phage library members is typically applied to the apical side of the polarized cells in the apical chamber. The applied phage are then allowed a period of time to be transported through the monolayer.

Because the impermeable membrane immobilizes transported phage in the vicinity of the cell(s) expressing the cDNA that promotes the transcytosis of the phage, one can select using various micromanipulation techniques the cell(s) expressing a protein capable of directing the transcytosis of at least some of the phage display complexes. The cDNA located within such cells can then be used to identify the transport protein encoded by the gene.

6. Exemplary In Vivo Assays

General. The polypeptide-bearing icosahedral phage disclosed herein can also be used in in vivo screening methods to identify polypeptides that are substrates for transport proteins. In general, the in vivo methods involve introducing a population of phage into a body compartment in a test animal and then recovering and identifying the subset of introduced phage that are transported through cells lining the body compartment into which the phage were placed. More specifically, the screens typically involve monitoring a tissue or body fluid (e.g., the mesenteric blood and lymph circulation) for the presence of transported phage that have entered the blood or lymph of the test animal.

The polypeptide displaying phage can be deposited in any body compartment that contains transport proteins capable of transporting such a phage into a second body compartment, especially the intestinal lumen and the central nervous system compartment. The test animal can be of essentially any type including primates, domestic animals (e.g., dogs and cats), farm animals (e.g., sheep, pigs and cows). Certain methods can be performed with human subjects, whereas other methods are conducted with non-human animals.

Certain methods using phage are performed by withdrawing a sample from the receiving compartment and titering the sample to detect plaque formation, the formation of a plaque indicating the transport of a phage through the cell layer separating the two compartments. Other methods are performed with phage that include a reporter. The reporter can be a capture tag that facilitates the retrieval and concentration of phage that are transported. Suitable capture tags, include for example, biotin, magnetic particles associated with the library complex, haptens of high affinity antibodies, and high density metallic particles such as gold or tungsten. The phage can also include a detection tag to further enhance the retrieval and detection process. As the name implies, detection tags are molecules that are readily identifiable and can be used to monitor the retrieval and concentration of transported phage. Examples of such compounds include fluorescent molecules, amplifiable DNA molecules, enzymatic markers, and bioactive molecules.

Because of the replication and amplification potential of the icosahedral phage disclosed herein, the in vivo assay methods provide a very sensitive means of tracking polypeptide-bearing phage that are transported from one body compartment to another, such as the transit of the phage from the intestine to the blood. Even if only a very small number of phages are recovered, the phages can be amplified to facilitate identification.

Tissue Localization Methods. Other methods provide information on tissue localization of the transported icosahedral phage. For example, phage libraries introduced into the blood can be analyzed for members taken into the brain through the blood brain barrier. The destination tissue (brain) is excised and sectioned (though not fixed) as for histological examination. Phage that have successfully transported into the tissue can be analyzed by homogenization of the tissue, followed by titering on host cells and sequence tag identification as described above. Alternatively, detection can be performed in situ. In such methods, a histological slice of thickness from 0.1 to several millimeters (depending on the resolution required for a particular analysis) is placed on a filter spread with a lawn of growing host bacteria and placed on a nutrient agar plate. This plate is placed at 37° C. for a time sufficient to allow diffusion of phage in the tissue to infect the bacteria and to form plaques of ~0.1 to several mm. In another option, slices are placed on a membrane filter for a period of sufficient duration that allows phage particles that have diffused from the slices to be captured on the filter. The filter is then placed on lawn of host bacteria overnight to allow plaque formation. The time of incubation depends on the type of phage employed and the size of plaques desired, and can range from a few minutes to many hours. The tissue slice is then removed and analysis of the plaques is undertaken.

There are a variety of possible formats by which the phage can be amplified and immobilized for analysis. The protocol described here represents just one of the acceptable protocols. The phage plaques can be counted, individual plaques eluted and sequenced, and the array of plaques probed with a panel of labeled oligonucleotides for in situ tag identification, much as described above. This process provides information on the identification of successfully transported phage clones (and their attached polypeptides), quantitation of the number of transported particles from each clone (a measure of the success and capacity of a given clone (polypeptide)), and the micro-localization of the phage in the tissue.

The most successful clones are selected and decoded to identify the polypeptide borne by their coat. This polypeptide represents an activating substrate for a receptor that mediates the transport of the phage. With this substrate as a probe, the responsible receptor can then be identified and cloned by standard expression cloning techniques. The general method thus identifies a receptor mediating a endocytosis/transcytosis pathway with desirable characteristics (high capacity in this example), and a substrate that activates the receptor, along with some detail on the kinetics of transport and the microlocalization within the destination tissue.

Variations. The initial enrichment process can be repeated with the recovered icosahedral phage in the same or a different animal for additional enrichment (although typically at the expense of yield in phage retrieved). In another variation, a series of separate pools of phage are sequentially applied to a single animal, retaining the ability to determine which group of polypeptides each phage belongs to by "pool tagging". Each library or pool is labeled with a distinguishable tag (e.g., fluorescence). Each library or pool can be administered to the intestinal loop or the intact intestine of the test animal, and the transported phage recovered by the methods described above. The library or pool from which the phage derive is determined by the pool tag associated with each phage. This method can be used sequentially as a means to deconvolute a library of polypeptides.

For example, one group of polypeptides having a certain structural characteristic is labeled with a fluorescent molecule that generates a first color; a second set of polypeptides having a different structural characteristic than the first set is labeled with a fluorescent molecule that generates a second color. Once the polypeptide displaying phage that have passed through the cells have been recovered, one can determine the relative number of each group of polypeptides that were capable of being transported through the cells from the relative amount of each colored phage. The group of polypeptides having the highest activity can then be further subdivided into subfamilies, each subfamily having a certain characteristic structure, and the process repeated as many times as desired. Each time the process is repeated it becomes possible to more closely identify what structural characteristics are associated with transport activity.

Additional details regarding related methods of assaying transport proteins utilizing compound-bearing particles is described in copending and commonly owned U.S. application Ser. No. 09/661,927, filed Sep. 14, 2000, which is incorporated herein by reference in its entirety.

B. Receptor Binding Assays

1. ELISA

One approach for screening library compounds for those capable of binding a particular receptor utilizes known enzyme-linked immunosorbent assay (ELISA) methods. For instance, a receptor of interest (or a cell expressing the receptor of interest) can be immobilized on a solid support according to known procedures. An aliquot of a compound-bearing phage is withdrawn from an array location such as described above and contacted with the immobilized receptor under conditions conducive to specific binding. Unbound compound is rinsed away. Binding of compound to the immobilized receptor can be detected by adding labeled anti-phage antibody to the assay mixture to bind to phage immobilized to the support.

As described above, the assays are typically conducted using multi-well plates, in which each well contains the immobilized receptor of interest. Which compounds bind to the receptor of interest can be determined according to the correspondence regimes set forth above. If the phage displays multiple different compounds, a second round of screening is necessary to identify which of the displayed compounds is in fact active.

The general ELISA method just described can be modified to enable multiplex analyses to be conducted. In such multiplex assays, multiple different receptors are placed in a single assay location (e.g., a well in a multi-well plate) so that binding of compounds to multiple different receptors is assayed simultaneously. In certain multiplex methods, each of the different receptors is attached to a different type of support, each type of support being distinguishable from the other support types. For instance, the supports may differ in size, shape or be labeled with different labels (e.g., different fluorescent dyes). Confocal or semi-confocal microscopy can distinguish between the different support structures and thus can identify which of the receptors is bound to a compound. The confocal and semi-confocal fluorescent microscopy equipment necessary to conduct such assays is commercially available from either Perkin Elmer (FMAT instrument) or Cellomics.

2. Binding/Elution Approaches

Another approach, typically utilized when the phage include a tag, involves the direct binding of pools of compound-bearing phage against an immobilized receptor and subsequent elution (see, for example, Cwirla, et al., Proc. Natl. Acad. Sci. USA 87:6378-6382 (1990)). Incubation of the pools of compound-bearing phage with the desired immobilized receptor is generally performed in the well of a multi-well plate. Unbound phage are washed away. Bound phage are subsequently eluted at low pH or under other conditions that disrupt specific binding between a compound displayed on a phage and the immobilized receptor. Eluted phage are then used to infect a host cell (e.g., $E.$ $coli$) and then plated out as individual colonies. Individual colonies are picked and placed into separate wells either manually or, more typically, with a commercial system (QBot) and grown.

Compounds borne on phage that yield positive assay results can be identified through standard analytical techniques or, for phage carrying a heterologous sequence tag, by sequencing the tag or generating a probe from the tag that can be used to probe the archival plates as set forth above.

3. FACS

Another option for assaying for receptor binding is to contact the multivalent phage with fluorescently labeled receptors. The phage are allowed to form a complex with the receptors and then washed to remove unbound or non-specifically bound receptors. A FACS instrument is then utilized to identify and physically isolate individual phage to which a fluorescent receptor is bound.

C. Assays for Antimicrobial Activity

The icosahedral phage provided herein can also be used in screens to identify compounds having antimicrobial activity, i.e., the ability to retard or kill microorganisms (e.g., bacteria, viruses, fungi and parasites). One suitable approach is described in WO 95/12608 (incorporated by reference in its entirety). In brief, cells are plated on agar plates and then overlayed with a layer of agar into which the phage disclosed herein are suspended at a suitable dilution so that individual phage can be picked using a capillary for example. The compound borne by the phage is released, such as by cleavage of a linker attached to the compound. The agar plate is cultured to allow diffusion of the compound through the upper layer of agar down to the layer containing cells. The extent to which the released compound affects the growth or morphology of the cells is monitored. Zones showing the desired response (e.g., death) are selected and regions within the zone from which the compound diffused are picked. The phage in the picked zone is expanded and the tag decoded to identify the compound originally attached to the phage, thus identifying a compound with the desired antibacterial activity.

D. Signal Transduction Assays

Cells can be genetically engineered so that upon binding of a compound to a receptor signal transduction triggers the formation of a detectable signal. For example, an exogenous gene encoding an enzyme can be inserted into a site where the exogenous gene is under the transcriptional control of a promoter responsive to a signal transducing receptor. Thus, binding to the receptor triggers the formation of the protein which can react with a substrate within the cell to generate a detectable signal. Using such cells, the compounds displayed on the phage described herein can be screened for their ability to bind a receptor and transduce a signal within the cell. In certain instances, the compound can be released from the phage by cleavage of a linker attached to the compound. By conducting the assay within a well, it is still possible to keep track of the compounds that are active, even when released from the phage. Related assays can be conducted to identify compounds capable of agonizing or antagonizing a signal transducing receptor.

E. Assays for Enzyme Substrates

1. General

A library of compounds displayed on phage can also serve as a source of potential substrates for enzymes of interest. The particular substrate being screened can vary. Certain methods involve screening a library of compound-bearing phage for activity with essentially any type of enzyme, including, but not limited to, proteases, kinases, phosphatases, conjugating enzymes (e.g., glucuronidation, sulfation), metabolizing enzymes and hydrolases (e.g., those cleaving ester linkages). In other methods, the compounds borne by the phage are potential prodrug linker moieties and the screen involves identifying linkers that are cleaved under particular physiological conditions. Still other screens are conducted with a library of compounds attached to phage that are variants of a drug molecule. The goal being to identify a compound that is less susceptible to modification or inactivation by an enzyme.

2. Assay Procedures

The methods initially generally involve contacting the library of compound-bearing phage with either a purified or crude enzyme preparation under conditions compatible with the activity of the target enzyme. After sufficient exposure of the library to the active enzyme, two primary options are available to identify phage that bear substrates for the enzyme. One approach is a negative selection approach and involves detecting the absence of the initial compounds displayed on the phage. Alternatively, a positive selection approach can be utilized. This approach involves selecting for the presence of a product displayed on the phage resulting from the conversion of displayed compounds.

The selection step is often performed by binding the library to a "receptor" chosen to bind the substrates of the products of the enzyme reaction. The particular "receptor" utilized can take a variety of forms. Suitable receptors include, but are not limited to: 1) an antibody or biological receptor recognizing some, most, or all of the starting displayed compounds; 2) an antibody or cellular receptor recognizing potential products of the reaction; 3) an antibody or cellular receptor recognizing a moiety added to the library compounds via the activity of the enzyme; 4) an antibody or biological receptor recognizing a degradation product of the reaction; and 5) an antibody or biological receptor recognizing a portion of the initial compounds that becomes exposed as a consequence of the activity of the enzyme.

Enzymatic degradation can be assayed for and detected by utilizing the displayed compounds to link a common affinity "handle" to the phage. For example, protease substrates can be selected by creating a library of compounds attached to a phage. A common antibody epitope or hapten (the affinity handle) is installed or attached to the displayed compounds distal to the phage attachment point. The library is subsequently exposed to the protease of interest. The resultant library is screened against an antibody specific for the affinity handle, with free phage being enriched for protease substrates.

A similar method can be utilized to select and optimize prodrug linker moieties. Initially, a library of potential prodrug linkers is created and attached to phage. A common affinity handle is installed on the displayed compounds distal to their attachment point on the phage and the library exposed to specific enzyme preparations or to extracts of the tissue likely (or desired) to effect cleavage. Following exposure, the library is selected against an antibody recognizing the affinity handle. The remaining free phage carry compounds enriched in linker moieties cleaved by the enzyme/ tissue fraction of interest.

Another option for selecting prodrug moieties is as follows. A library of potential prodrug linkers connected to the drug compound of interest is created and attached to phage, with attachment to the phage through the drug portion of the complex. The library is then exposed to the enzyme or tissue fraction of interest. The library is screened for binding to a receptor or antibody specifically recognizing the drug cleaved free of the linker moiety. The captured phage carry compounds enriched in linkers cleaved by the enzyme/tissue of interest.

The foregoing screening methods for prodrug moieties can be adjusted to identify prodrug linkers that are optimized to be more easily or less easily cleaved by an enzyme/tissue fraction of interest. For example, the stringency of selection can be controlled by altering the conditions of the enzyme reaction. In particular, the time and temperature of the reaction can be increased or decreased to favor the selection of either more labile or more stable linker structures, either in the context of the drug of interest or in a general format.

Certain methods can be designed to select a variant of a drug molecule that is less susceptible to modification or inactivation by an enzyme or a target tissue or systemic exposure in an animal. Such methods involve creating a library of the variants of the drug and attaching them to a phage (e.g., a phage). The library is exposed to the enzyme, the target tissue, or the body compartment of the animal. The library is recovered and then screened against a target receptor of the drug (the receptor recognizing only the pharmacologically active molecules). The captured phage are enriched in compounds stable to the metabolic activity of the chosen enzyme, tissue, or tissue compartment. Optimization of the selected variants can be accomplished by controlling the stringency of the metabolic step as just described.

VIII. Options Subsequent to Screening

A. Modification of Lead Compound

Once a compound has been identified after an initial round of screening as having the capacity to function as a substrate for a receptor-mediated transport process and be transported into or through a cell (a lead compound or lead compounds), the compound can serve as the basis for additional rounds of screening tests. For example, if several different compounds are identified in an initial round, the compounds can be analyzed for common structural features or functionality. Based upon such common features, another library incorporating one or more of the common features or functionalities can be synthesized and subjected to another round of screening to identify other compounds that are potentially more active than the polypeptides identified initially. Alternatively, a new set of compounds derived from each of the positive compounds identified in the initial screening can be synthesized and utilized in another round of screening. Of course, this process can be repeated in an iterative manner until the desired degree of refinement in the compound is obtained.

B. Attachment of Different Moieties at Linkage Site

One feature of the screening methods is that the compounds are tethered to a relatively large moiety, namely a phage. Hence, active compounds identified through the screening methods are likely able to retain activity even if a different moiety is attached at the linkage site (i.e., the site on the compound to which the phage is attached). Further studies can be undertaken to identify what other types of moieties can be attached at the linkage site.

For example, various other small molecules can be attached at the linkage site. Such small molecules can have activities similar to that of the identified compound or an unrelated but complementary activity. Examples of the latter type of compound include buffers, antioxidants, molecules with affinity for serum albumin (useful for extending half-life of the compound in vivo), and molecules with affinity for proteins expressed in specific organs.

Since the compounds identified through certain of the screening methods described herein are potential substrates for receptor-mediated transcytosis, the compounds can be conjugated to various pharmaceutical agents to promote selective delivery of the agent to a particular target. The pharmaceutical agent can be essentially agent that can be transported via endocytosis or transcytosis when linked to a substrate. Examples of such agents include, but are not limited to, analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; anihelminthic agents; antihistamines; antihyperlipidaemic agents; antihypertensive agents; anti-infective agents; antiinflammatory agents; antimigraine agents; antineoplastic agents; antiparkinsonism drugs; antipruritic agents; antipsychotic agents; antipyretic agents; antispasmodic agents; antitubercular agents; antiulcer agents; antiviral agents; anxiolytic agents; appetite suppressants; attention deficit disorder and attention deficit hyperactivity disorder drugs; chemotherapeutic agents, cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; steroids; smoking cessation agents; sympathomimetics; tranquilizers; vasodilators; β-agonist; and tocolytic agents.

Instead of attaching another small molecule, various supports can be attached to the linkage site. Examples of such supports include nanoparticles (see, e.g., U.S. Pat. Nos. 5,578,325 and 5,543,158), molecular scaffolds, liposomes (see, e.g., Deshmuck, D. S., et al., Life Sci. 28:239-242 (1990), and Aramaki, Y., et al., Pharm. Res. 10:1228-1231 (1993), protein cochleates (stable protein-phospholipid-calcium precipitates; see, e.g., Chen et al., J. Contr. Rel. 42:263-272 (1996), and clathrate complexes. These supports can be used to attach other active molecules. Certain supports such as nanoparticles can also be used to encapsulate desired compounds such as the pharmaceutical agents listed above.

C. Formulation of Compounds into Pharmaceutical Compositions

Compounds identified through the screening and rescreening processes described above to have a desired activity, and complexes of such compounds with the supports and pharmaceutical agents listed above, can be incorporated into pharmaceutical compositions. Typically, such compounds and complexes are combined with pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can also include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents, detergents and the like (see, e.g., Remington's Pharmaceutical Sciences, Mace Publishing Company, Philadelphia, Pa., 17th ed. (1985); for a brief review of methods for drug delivery, see, Langer, Science 249:1527-1533 (1990); each of these references is incorporated by reference in its entirety).

The compositions can be administered for prophylactic and/or therapeutic treatments. A therapeutic amount is an amount sufficient to remedy a disease state or symptoms, or otherwise prevent, hinder, retard, or reverse the progression of disease or any other undesirable symptoms in any way whatsoever. In prophylactic applications, compositions are administered to a patient susceptible to or otherwise at risk of a particular disease or infection. Hence, a "prophylactically effective" is an amount sufficient to prevent, hinder or retard a disease state or its symptoms. In either instance, the precise amount of compound contained in the composition depends on the patient's state of health and weight.

An appropriate dosage of the pharmaceutical composition is readily determined according to any one of several well-established protocols. For example, animal studies (e.g., mice, rats) are commonly used to determine the maximal tolerable dose of the bioactive agent per kilogram of weight. In general, at least one of the animal species tested is mammalian. The results from the animal studies can be extrapolated to determine doses for use in other species, such as humans for example.

The pharmaceutical compositions can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods. The route of administration depends in part on the chemical composition of the active compound and any carriers.

Particularly when the compositions are to be used in vivo, the components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The following examples are provided to illustrate certain aspects of the methods and phage described herein and are not to be construed to limit the invention.

EXAMPLE 1

Preparation of Polypeptide Display Library on Icosahedral Phage

A heterologous nucleic acid is inserted into T7 by digesting the insert with EcoRI and HindIII, and ligating the heterologous sequence to prepared vector arms of both T7 display vectors to obtain inserts that are in the same translational reading frame as the 10B capsid protein. An epitope tag (e.g., a portion of the human influenza hemagglutinin protein (HA)), is placed at the carboxy terminus of the insert to facilitate detection of phage displaying the inserted sequence in subsequent assays. The resulting DNA is incubated with an in vitro packaging extract, and the phage products are used to infect a culture of *E. coli* BLT5615. Phage particles produced from these cells display the inserted heterologous sequence fused to the T7 capsid protein (gene 10). Large amounts of phage are prepared by infecting a culture of bacterial cells grown in M9TB to an $OD_{600}$ of 0.6-0.8 with a phage stock or single plaque. The culture is incubated with shaking at 37° C. for 1-3 hours until lysis is observed. The lysate is clarified by centrifugation at 8,000×g for 10 minutes.

T7 phage are purified from the cleared supernatant by precipitation with polyethylene glycol (PEG 8000) followed by banding in a CsCl step gradient as follows. Phage are precipitated from the supernatant by adding PEG 8000 to a final concentration of 10% (w/v), incubating on ice for 1 hour, followed by centrifugation at 8,000×g for 15 minutes. Phage are extracted from the PEG pellet in 1M NaCl, 10 mM Tris-HCl, pH 8.0, 1 mM EDTA, and the concentrated phage solution is layered atop four steps of different density CsCl solutions in a clear ultracentrifuge tube. The four CsCl layers are made by mixing a stock solution of 62.5% CsCl in TE buffer (10 mM Tris-HCl, pH 8.0, 1 mM EDTA) in the following ratios: 1:2, 1:1, 2:1, 1:0 CsCl:TE. Successively denser solutions are underlayed in the tube and the concentrated phage solution is layered on top of the CsCl steps. The tubes are centrifuged at room temperature for 60 minutes at 35,000 rpm in a Beckman SW41 rotor. After centrifugation, the turbid band of phage particles above the 2:1 layer is removed by piercing the side of the tube with a syringe. Recovered phage particles may be further purified by adding enough 62.5% CsCl solution to make the solution denser than the 2:1 CsCl:TE mixture, then floating up to an interface with an upper layer of 1 M NaCl by again centrifuging at the same speeds and time cited above. Recovered phage particles are then dialyzed in PBS and stored at 4° C., or at −80° C. following the addition of 8% glycerol.

EXAMPLE 2

Attachment of Compounds to T7 Phage Particles Through Non-Covalent Linkage (Biotin/Streptavidin)

I. Preparation of T7 Phage

Figure 12:
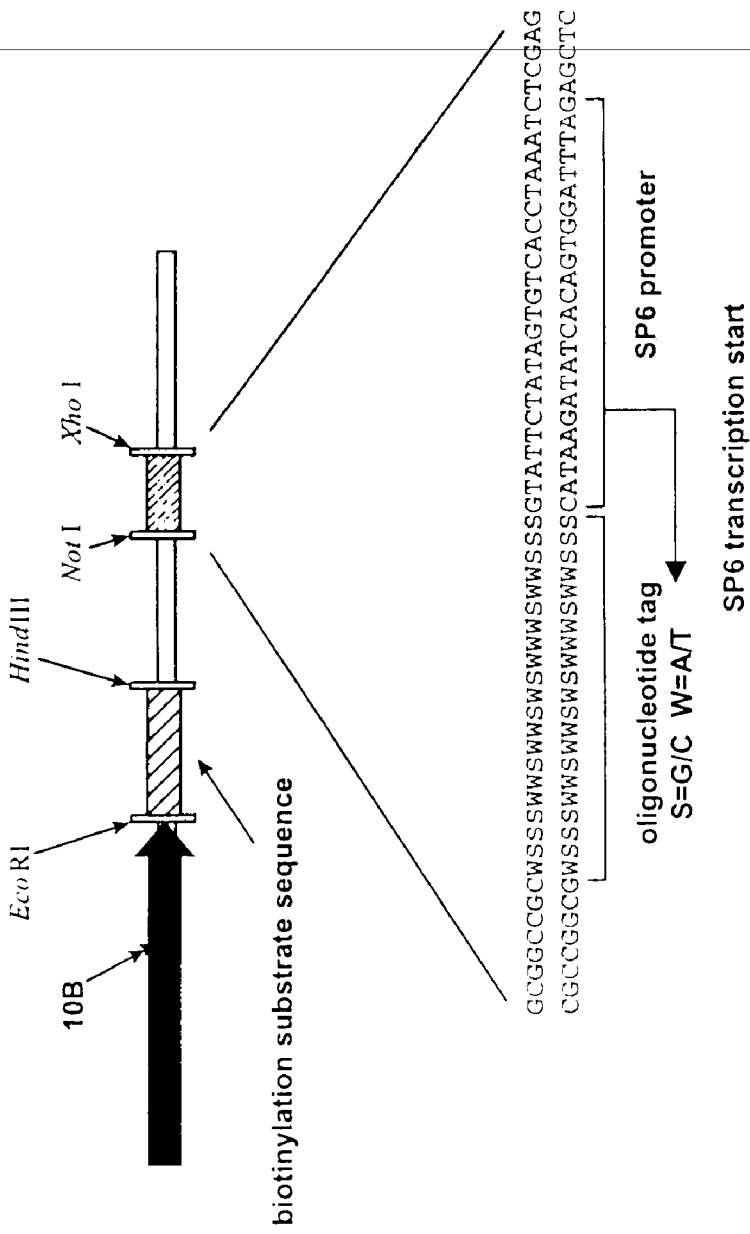
FIG. 12 shows an example of the location and orientation of various genetic elements inserted into a T7 phage vector thus enabling a hybridization probe to be prepared from the phage.

The 16-amino acid BirA substrate sequence was cloned into the 3' end of gene 10B, the major coat protein of T7 phage (FIG. 11). Phage DNA was prepared in vitro followed by infection into *E. coli* BL21 cells. Phage produced by this vector display substrate sequence fused to all 415 copies of major coat protein present in the mature T7 particle. A collection of randomly synthesized oligonucleotides is inserted into a non-expressed portion of the phage genome to create a population of phage clones, each uniquely encoded by a specific oligonucleotide sequence (FIG. 12). The library is then plated on a bacterial lawn of BL21 cells, and individual plaques picked and added to wells of microtiter plates.

Host bacteria are added to each well and the phage clones expanded by growth for 3 to 6 h at 37° C. Biotinylation of the substrate sequence by the native *E. coli* biotin holoenzyme synthetase (BirA) occurs in vivo during overnight growth of the phage. Increased levels of biotinylation can be achieved by using a host bacterial strain that overexpresses BirA to amplify the phage. The bacterial debris is then removed from each well by centrifugation or filtering. Streptavidin is added to all wells at sufficient excess to saturate the biotinylated phage. Once again the phage particles are precipitated or affinity purified and washed to remove the excess streptavidin.

Alternatively biotinylation of the displayed substrate sequence can take place in vitro by adding biotinylation buffer, biotin, and the enzyme BirA to the phage containing supernatant. The plates are incubated at 30° C. for 30 minutes to biotinylate the phage particles, and the phage are precipitated or affinity purified in the wells and washed to remove the excess biotin. Streptavidin is added to all wells at sufficient excess to saturate the biotinylated phage. Once again the phage particles are precipitated or affinity purified and washed to remove the excess streptavidin.

The extent of in vivo biotinylation of phage particles displaying the substrate sequence can be measured using a phage ELISA. The wells of a microtiter plate are coated with 2.5 µg of avidin and blocked with PBS/1% BSA. Phage are added to each well in the presence or absence of 10 µM free biotin and incubated at 4° C. for 1 hour. Bound phage are detected with a horseradish peroxidase-conjugated anti T7 antibody followed by the addition of ABTS development buffer. The amount of horseradish peroxidase activity in each well is measured by reading the absorbance at 405 nm with a microtiter plate reader. Phage displaying the BirA substrate sequence are specifically captured on avidin coated microtiter wells.

II. Attaching the Compounds to the Phage

A collection of D-peptides is synthesized to contain a common C-terminal biotinylated lysine. An aliquot of each of the compounds is added to a corresponding well of the 96 wells containing the streptavidin-prepared phage particles. After a period of incubation to allow the biotinylated compounds to bind to the phage particles, 10 µM biotin is added to block available binding sites on the phage, and an aliquot is taken from each well and pooled. The microtiter plate is set aside as a spatially-addressed archive of compound-decorated phage clones. The pooled phage are precipitated and washed to remove the free compound and biotin.

EXAMPLE 3

Screening a Library of Compounds Displayed on T7 Phage Particles for Compounds Absorbed by Transcytosis through Polarized Epithelial Cells I. Cell Culture:

Low passage number MDCK cells are grown in DMEM supplemented with 10% FBS and antibiotics (Kanamycin 100 ug/ml; Penicillin 0.5 units/ml; Streptomycin 0.5 ug/ml) to approximately 80% confluence on TC plastic. The cells are removed from the dishes with trypsin/EDTA and seeded at confluent density (approximately $5 \times 10^5$ cells/cm$^2$) onto 12 mm or 24 mm transwells (0.4 µm pore size). The cells are returned to the incubator for 5 days, with daily medium change, to establish differentiated monolayers.

II. Screening for Transcytosis of Library Members

Normal growth medium containing antibiotics is removed from the 5 day differentiated cultures and replaced with DMEM supplemented with 10% FBS (no antibiotics). The cells are returned to the incubator for 1 to 2 h to allow equilibration of the medium. A T7 phage library is PEG precipitated and resuspended in 1 ml of DMEM supplemented with 10% FBS (0.5 ml for 12 mm transwell) at a concentration of ~$10^{12}$ TU/ml One ml of medium (0.5 ml for 12 mm transwell) is removed from the apical chamber and replaced with 1 ml (0.5 ml for 12 mm transwell) of phage resuspended in cell culture medium. (Alternatively amplified phage stocks are added directly (without PEG precipitation) to the apical chamber in a volume not exceeding 10% of the total apical volume; the appropriate volume of cell culture medium is removed from the apical chamber just prior to the addition of the amplified phage stock to maintain the correct apical volume). 2 µCi of $^3$H-inulin (1 µCi for 12 mm transwells) is also added to each transwell along with the phage to monitor monolayer integrity.

Cultures are returned to the 37° C. incubator for 2 h. At the end of 2 h, the medium from the apical chamber (1.5 ml for 24 mm transwell; 0.5 ml for 12 mm transwell) and basal chamber (2.5 ml for 24 mm transwell; 1.5 ml for 12 mm transwell) is collected. 1% of the medium from each chamber is counted in a scintillation counter to measure $^3$H-inulin passage.

The remaining sample is then titered:

Apical medium is diluted down to approximately $10^3$ TU/ml. 100 µl of this dilution is then combined with 200 µl of BL21 cells (O.D. 0.6-0.8) and 3 ml top agar and plated onto LB plates. The plates are then placed at 37° C. for 3 h or at room temperature overnight. 10% of the basal medium (250 µl for 24 mm transwell; 150 µl for 12 mm transwell) is combined with 200 µl of BL21 cells (O.D. 0.6-0.8) and 3 ml top agar and plated onto LB plates. The plates are then placed at 37° C. for 3 h or at room temperature overnight.

EXAMPLE 4

Screening a Library of Compounds Displayed on Phage Particles to Identify Compounds Absorbed by Transcytosis Through the Intestinal Epithelium A library of compound displayed on T7 phage is prepared as described in Example 2 and screened as follows:

The washed pool is resuspended in 0.2 ml of buffered saline and placed directly into the proximal portion of the small intestine of a rat. At times 10, 30, 60, 120, 240, 480 minutes following insertion of the library, blood samples are taken from the tail vein of the animal. Samples are anticoagulated and the red blood cells removed by centrifugation. Each sample of cleared plasma is then plated on a lawn of host bacteria and incubated overnight to form plaques. The nucleic acid tag in each plaque is determined as previously described in the tagged screening section supra.

EXAMPLE 5

Screening Library of Compounds Displayed on Phage Particles to Identify Compounds Absorbed by Transcytosis Through the Endothelial Blood Brain Barrier Libraries of compounds displayed on phage particles are prepared as described in Example 2 and screened as follows:

The washed pool is resuspended in 500 µl of buffered saline and 50 µl injected into each of 10 rats by IV injection. At times 10, 30, 60, 120, 240, 480 minutes following insertion of the library, rats are killed, and their brains perfused with saline. Their brains are excised and divided along the medial axis. One half of each brain is homogenized and the supernatant from a low speed spin is plated on a lawn of host bacteria for plaque growth. The remaining half of each brain is sliced into ~1 mm slices and placed on a membrane filter for captured of diffusing phage particles. The array of slices is photographed for later alignment of plaques with brain slices, and the filter is marked for orientation. After overnight period at 4° C., the slices are removed and the filter is placed on a lawn of host bacteria and incubated at 37° C. overnight to allow plaque formation. The nucleic acid tag in each plaque is determined as previously described in the tagged screening section supra.

EXAMPLE 6

Quantitative Assay of Single Compounds for Transcytosis through Epithelial Cell Layer I. Cell Culture:

Low passage number MDCK cells are grown in DMEM supplement with 10% FBS and antibiotics (Kanamycin 100 ug/ml; Penicillin 0.5 units/ml; Streptomycin 0.5 ug/ml) to approximately 80% confluence on TC plastic. The cells are removed from the dishes with trypsin/EDTA and seeded at confluent density (approximately $2\times10^5$ cells/well) onto 0.4 μm millicell inserts arranged in 96 well format (6 mm diameter inserts). Each chamber contains 250 μl of medium. The cells are returned to the incubator for 5 days to establish differentiated monolayers (medium is changed daily).

Addition of Phage:

Normal growth medium containing antibiotics is removed from the 5 day differentiated cultures and replaced with DMEM supplemented with 10% FBS (no antibiotics). The cells are returned to the incubator for 1 to 2 h to allow equilibration of the medium.

During this time each phage clone is precipitated (using $\frac{1}{10}$ vol of acetic acid for fd or PEG for T7) and resuspended in 250 μl of DMEM supplemented with 10% FBS at a concentration of ~$10^{12}$ TU/ml. The medium is removed from the apical chamber and replaced with 250 μl of phage resuspended in cell culture medium. (Alternatively each phage clone is added directly (without precipitation) to the apical chamber in a volume not exceeding 10% of the total apical volume; the appropriate volume of cell culture medium is removed from the apical chamber just prior to the addition of the amplified phage stock to maintain the correct apical volume). $^3$H-inulin (0.5 uCi) is also added to each transwell along with the phage to monitor monolayer integrity.

The cells along with phage and $^3$H-inulin are returned to the 37° C. incubator for 2 to 6 h. At the end of the incubation, the medium from the apical chamber (250 ul/well) and basal chamber (250 ul/well) is collected. 1% of the medium from each chamber is then placed in a white 96 well plate with a clear bottom. 150 μl of scintillation fluid is added to each well, the plate is mixed, centrifuged, and placed in a scintillation counter to measure $^3$H-inulin passage.

The remaining sample is then titered as follows: Apical medium is diluted down to approximately $10^4$ TU/ml. 10 μl of this dilution is then combined with 100 μl of K91 recA bacteria (O.D. 0.6-0.8). The phage and bacteria are placed at 37° C. for 20-30 min and then plated onto LB Amp (100 ug/ml ampicillin) plates. The plates are then placed at 37° C. overnight. 50% of the basal medium (125 ul/well) is combined with 10 μl of the appropriate host bacteria and titered as described in the preceding examples.

EXAMPLE 7

Quantitative Assay of Single Compounds for Transcytosis through Intestinal Wall of Test Animal A single clone of phage is decorated with the test compound prepared as described in Example 2. The phage particles are placed in the delivery compartment of the animal (e.g., small intestine) and samples are taken from the destination compartment (e.g., blood) at times of 10 min to 12 h. Samples are plated on lawns of host bacteria, grown overnight and titer determined. The titer provides an estimate of the relative transport of that compound.

EXAMPLE 8

Covalent Attachment of Compounds to Filamentous and T7 Phage

I. General

Figure 13:
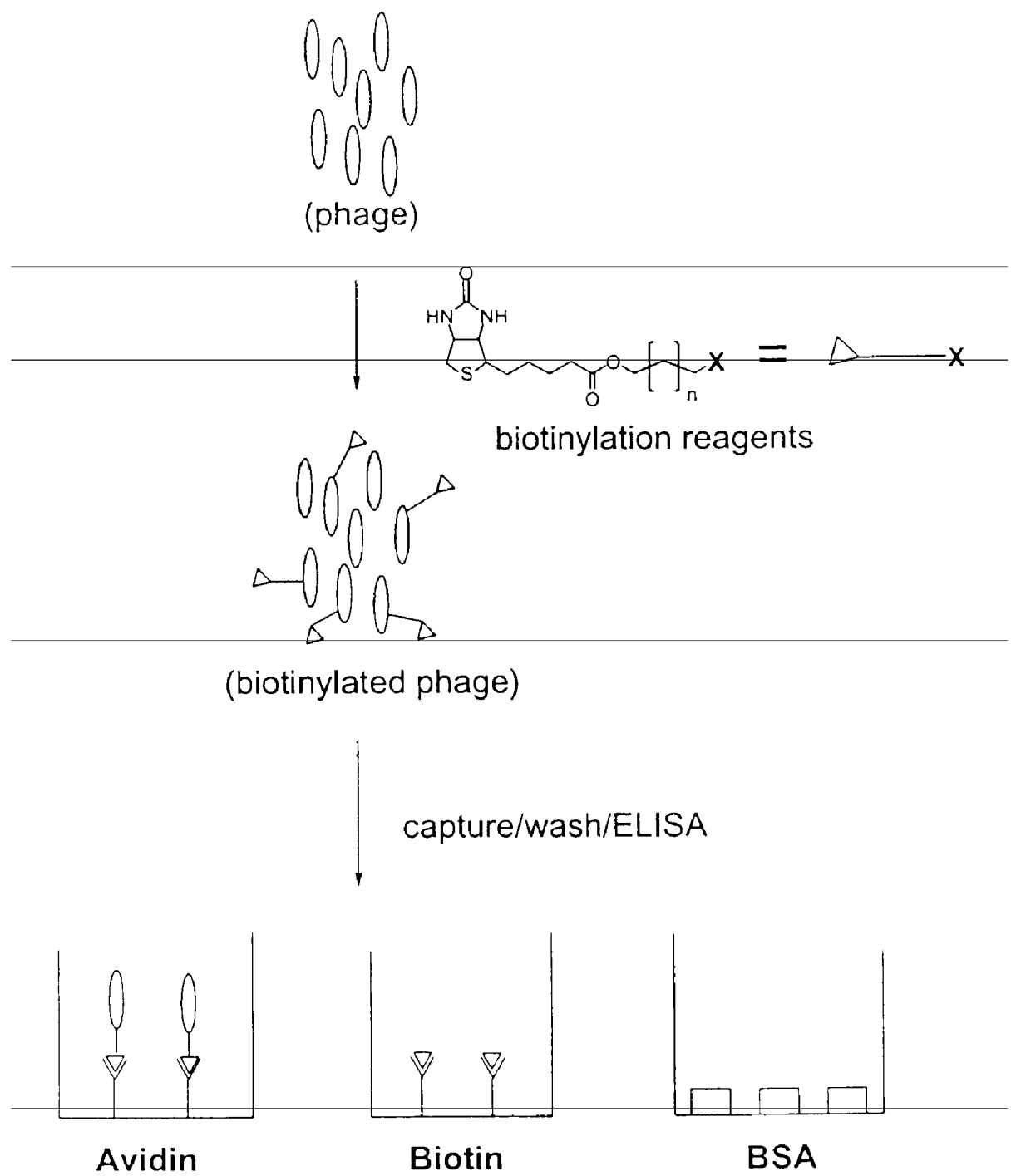
FIG. 13 summarizes the experimental design to demonstrate the chemical conjugation of biotin to phage.

This example describes an experimental system utilized to validate various strategies for covalently attaching small molecules to the coat proteins of filamentous and T7 phage. A representative small molecule was chosen, the successful attachment of which would indicate that a similar strategy could be employed to attach a variety of small molecules. Biotin served as this pilot small molecule, as its covalent attachment to the surface of phage can be easily detected due to its very strong and specific interaction with streptavidin. The experimental system used to validate the chemical conjugation of biotin to phage is depicted in FIG. 13.

This experiment entailed treating phage with various biotinylation reagents to covalently attach biotin to phage. Phage with covalently bound biotin were detected by first isolating the phage from excess biotinylation reagent and then adding the phage to immobilized streptavidin. The immobilized streptavidin binds biotin, thereby capturing biotinylated phage. After washing away any unbound phage, the captured phage were detected utilizing an Enzyme Linked Immunosorbent Assay (ELISA). This assay involved contacting captured phage with an anti-phage antibody that binds to captured phage. The anti-phage antibody is conjugated to horseradish peroxidase (termed anti-phage/HRP). After washing away the unbound anti-phage/HRP, a substrate of HRP is added, producing a colored product when acted on by HRP. This colored product is detected by monitoring absorbance at 450 nm. Consequently, the production of the colored HRP product indicates bound phage particles, captured via covalently attached biotin.

In order to ensure that the phage detected in this assay were captured by the specific interaction of the covalently attached biotin with immobilized streptavidin, a number of controls were included to account for non-specific binding. These controls involve first adding a large excess of biotin to the immobilized streptavidin prior to the addition of phage. The biotin binds streptavidin, blocking its ability to bind the biotin-conjugated phage. In addition, bovine serum albumin (BSA) was immobilized. Any phage captured by either immobilized BSA, or by streptavidin saturated with biotin, are not captured by the specific interaction of biotin with streptavidin, indicating the level of non-specific binding inherent in this assay.

II. Methods

A. Protocols for Attachment of Biotin to T7 Phase

1. NHS Ester Conjugation Chemistry

To 100 μL of a stock solution of T7 S-Tag phage (titer=$1.0\times10^{11}$ pfu/mL; T7 S-Tag phage are T7 phage that display a 15-amino acid peptide fused to the C-terminus of the major coat protein that binds to ribonuclease S-protein)

in PBS buffer was added 10 µL of a 6 mM aqueous solution of Sulfo-NHS-LC-biotin (available from Pierce). 90 µL of PBS buffer was added, and the solution was incubated at 0° C. for 3 h. 50 µL of 50% PEG was added to each reaction vial, cooled to 0° C. and centrifuged at 16,000×g for 5 min. The supernatant was discarded, and the phage pellet was resuspended in 500 µL PBS buffer. The procedure was repeated using 60 µM and 600 nM aqueous solutions of Sulfo-NHS-LC-biotin.

2. Maleimide Conjugation Chemistry

To 100 µL of a stock solution of T7 S-Tag phage (titer=$1.0 \times 10^{11}$ pfu/mL; T7 S-Tag phage are T7 phage that display a 15-amino acid peptide fused to the C-terminus of the major coat protein that binds to ribonuclease S-protein) in PBS buffer was added 10 µL of a 6 mM aqueous solution of PEO-maleimide-biotin (available from Pierce). 90 µL of PBS buffer was added, and the solution was incubated at room temperature for 2 h. 50 µL of 50% PEG was added to each reaction vial, cooled to 0° C. and centrifuged at 16,000×g for 5 min. The supernatant was discarded, and the phage pellet was resuspended in 500 µL PBS buffer. The procedure was repeated using 60 µM and 600 nM aqueous solutions of PEO-maleimide-biotin.

3. Amine/Carbodiimide Conjugation Chemistry

To 100 µL of a stock solution of T7 S-Tag phage (titer=$1.0 \times 10^{11}$ pfu/mL; T7 S-Tag phage are T7 phage that display a 15-amino acid peptide fused to the C-terminus of the major coat protein that binds to ribonuclease S-protein) in PBS buffer was added 10 µL of a 6 mM aqueous solution of 1-ethyl-3-(3-dimethylaminopropyl)carbodiimide (EDAC, available from Pierce) and 10 µL of a 6 mM aqueous solution of Biotin-LC-PEO-Amine (available from Pierce). 80 µL of PBS buffer was added, and the solution was incubated at room temperature for 2 h. 50 µL of 50% PEG was added to each reaction vial, cooled to 0° C. and centrifuged at 16,000×g for 5 min. The supernatant was discarded, and the phage pellet was resuspended in 500 µL PBS buffer. The procedure was repeated using 60 µM and 600 nM aqueous solutions of EDAC and Biotin-LC-PEO-Amine.

C. Methods For Detection of Covalent Conjugation of Biotin to Phage (1) Microtiter Plate Preparation: NeutrAvidin and two controls of biotin saturated-NeutrAvidin and BSA were immobilized according to the following procedure. 50 µL of a 100 ug/mL solution of NeutrAvidin (available from Pierce) was added to each well of columns 1-4 and 7-10 of a 96 well microtiter plate. The plate was covered, incubated at 37° C. for 1 h, and washed with PBS. 300 µL of 1% BSA/PBS was added to each well of the plate, incubated overnight at 4° C., and washed with PBS. 50 µL of 0.1% BSA/PBS was added to each well of columns 1,2,5-8, 11 and 12, and 50 µL of 0.1% BSA/PBS containing 20 µM biotin was added to each well of columns 3,4,9 and 10.

(2) Capture and Detection of Biotinylated T7 S-tag Phage: 50 µL of the biotinylated T7 S-tag phage solutions, prepared in part II.B.1-3 in this Example, were added to the first 6 wells of a row, which included duplicates of Neutravidin, biotin saturated-NeutrAvidin and BSA. In addition to phage treated with the biotin-conjugation conditions described above, a control experiment of untreated T7 S-tag phage was included. Following addition of the phage preparations, the microtiter plate was incubated overnight at 4° C. The plate was then washed with PBS, and 50 µL of a 1:5000 dilution of S-protein conjugated with horseradish peroxidase (S-protein/HRP, available from Novagen) in 0.1% BSA/PBS was added to each well. The plate was incubated at room temperature for 2 h, and washed with PBS. 100 µL of substrate solution (18 µL of 30% $H_2O_2$ added to 10 mL 1×ABTS) was added to each well, and the absorbance at 405 nm was measured in a microtiter plate reader.

III. Results

Figure 14:
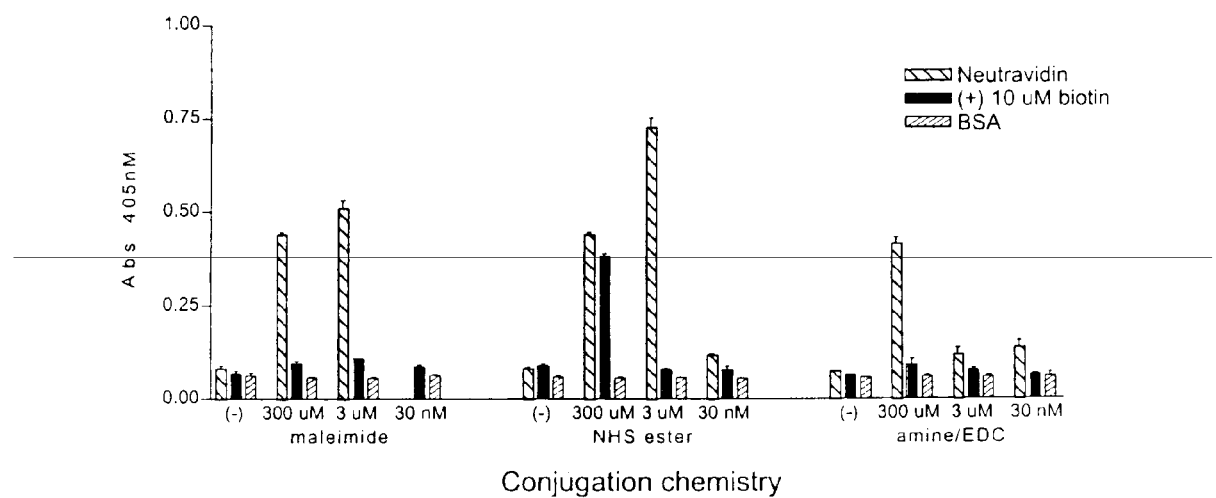
FIG. 14 shows ELISA results for T7 phage when biotin was chemically conjugated to the phage using NHS ester, maleimide and amine/carbodiimide chemistries.

The data from the foregoing ELISA assays are presented in FIG. 14, which shows the results of the use of NHS ester, maleimide and amine/carbodiimide chemistry with T7 phage. In all these ELISA assays, a strong signal is detected when the phage were treated with 300 µM of the biotinylation reagent. This signal drops when the phage were treated with 3 µM or 30 nM of the biotinylation reagents. The NHS ester attachment chemistry appears to be the most robust, as it produces a strong signal even at the lowest concentration of 30 nM. In addition, the controls for all these experiments have low signals, indicating that the biotinylated phage are specifically bound to NeutrAvidin.

EXAMPLE 9

Determination of the Infectivity of Phage Treated under Biotinylation Conditions I. General Having determined that a variety of attachment chemistries serve to conjugate biotin to T7 phage, the effect this has on the ability of the phage to infect bacterial host cells was examined. This was determined by simply measuring the titer of phage populations treated with various biotinylation reagents. Determining the titer of a phage population counts the number of infective phage particles in that population. The assay consists of adding the phage to an excess of host bacterial cells. The bacterial cells are then plated on the appropriate growth medium and incubated at 37° C. The number of bacterial colonies or plaques that form determines the number of infective phage particles. If attaching biotin to phage abrogates their ability to infect host bacterial cells, this would be detected as a decrease in the titer of that phage population.

II. Methods

A. Titer Determination of T7 Phage

200 µL of E. coli BL 21 cells at log phase were inoculated with 100 µL of the biotinylated T7 phage preparations. This was suspended in 3 mL of warm top agar, plated onto agar plates and incubated overnight at room temperature. The plaques were counted to determine the titer of the phage preparation.

III. Results

Figure 15:
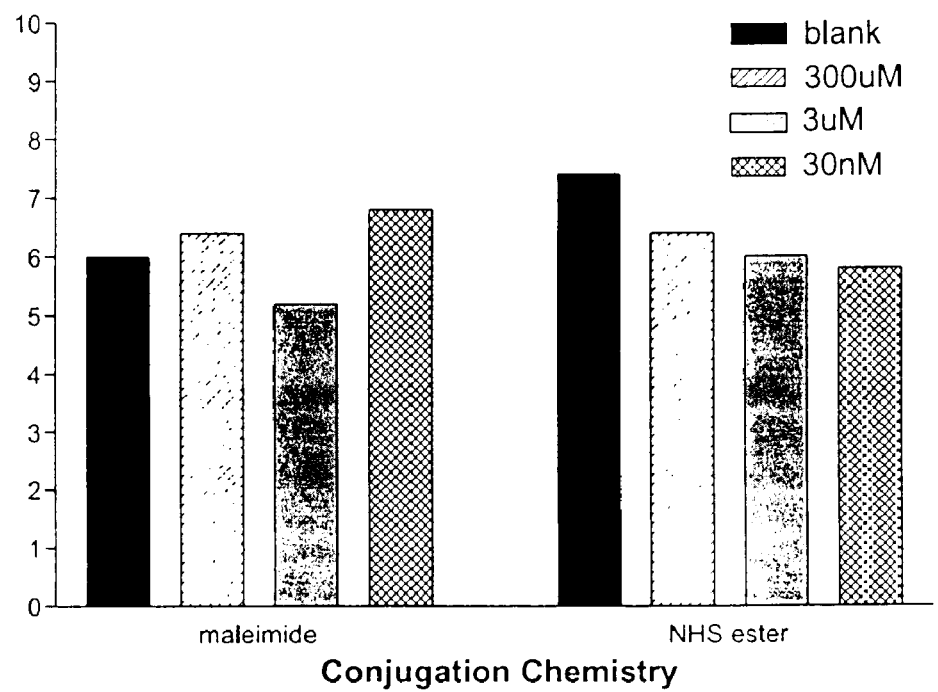
FIG. 15 shows titer results for T7 phage treated with maleimide and NHS ester attachment chemistries.

FIG. 15 demonstrates that conjugating biotin to T7 phage using maleimide or NHS ester attachment chemistries has no detrimental effect on the infectivity of those phage as the infectivity was not adversely effected by any of the conjugation methods.

EXAMPLE 10

Identification of Attachment Sites for Biotin in Filamentous and T7 Phage

I. General

The experiments described above demonstrate that several different attachment chemistries are able to conjugate biotin to phage, without interfering with their ability to infect host bacterial cells. In order to characterize which coat protein serves as the site of attachment, and to determine the extent of conjugation, fluorescein was attached to phage. Protein gel analysis allows for determination of which coat protein is fluoresceinated.

II. Methods

A. Covalent Attachment of Fluorescein to T7 Phase

Five reactions were run in which 200 µL of a stock solution of T7 S-Tag phage (titer=$1.0 \times 10^{11}$ TU/mL, T7 S-Tag phage are T7 phage that display a 15 amino acid peptide fused to the C-terminus of the major coat protein that binds to ribonuclease S-protein) were treated with various concentrations of fluorescein-5-EX, succinimidyl ester (fluorescein-SE, available from Molecular Probes): 1) 20 μL of DMSO only added, 2) 10 μL of a 6 mM solution of fluorescein-SE in DMSO added, 3) 20 μL of a 60 μM solution of fluorescein-SE in water added, 4) 20 μL of a 600 nM solution of fluorescein-SE in water added, and 5) 10 μL of a 6 mM solution of 5-(and-6)-carboxy fluorescein [5(6)-FAM] in DMSO added. To all of these reactions was added 180 μL PBS buffer and incubated at 0° C. for 3 h. 100 μL of 50% PEG was added to each tube and spun at 16,000×g for 5 min. The supernatant was removed, and the phage pellet was resuspended in 400 L PBS. 100 μL 50% PEG was added, cooled to 0° C. and spun at 16,000×g for 5 min. The supernatant was again removed, and the pellet resuspended in 500 μL PBS buffer.

B. Protein Gel to Identify Coat Protein of T7 Phase to which Fluorescein is Attached The T7 phage preparations from reaction #1 and #2 in part II A of this Example were diluted by 2× and 4× and run on a protein gel, with decreasing dilutions of sample #1 run in Lanes 1-3 and decreasing dilutions of sample #2 run in Lanes 4-6 respectively. The samples were prepared by adding 5 μL of 4× sample buffer to 15 μL of the indicated dilution and heated at 80° C. for 1 h. These were then loaded onto a 4-12% Bis-Tris gel and run at 200 V for 30 min. The gel was soaked in fixing buffer (50% MeOH/10% Acetic Acid/40% $H_2O$) overnight, followed by equilibration in PBS buffer for 3 h. The gel was visualized to detect those bands that contained fluorescein, then stained with SYPRO Ruby for 4 h, followed by washing with PBS for 1 h and visualized to detect all the protein bands on the gel.

III. Results

Figure 16:
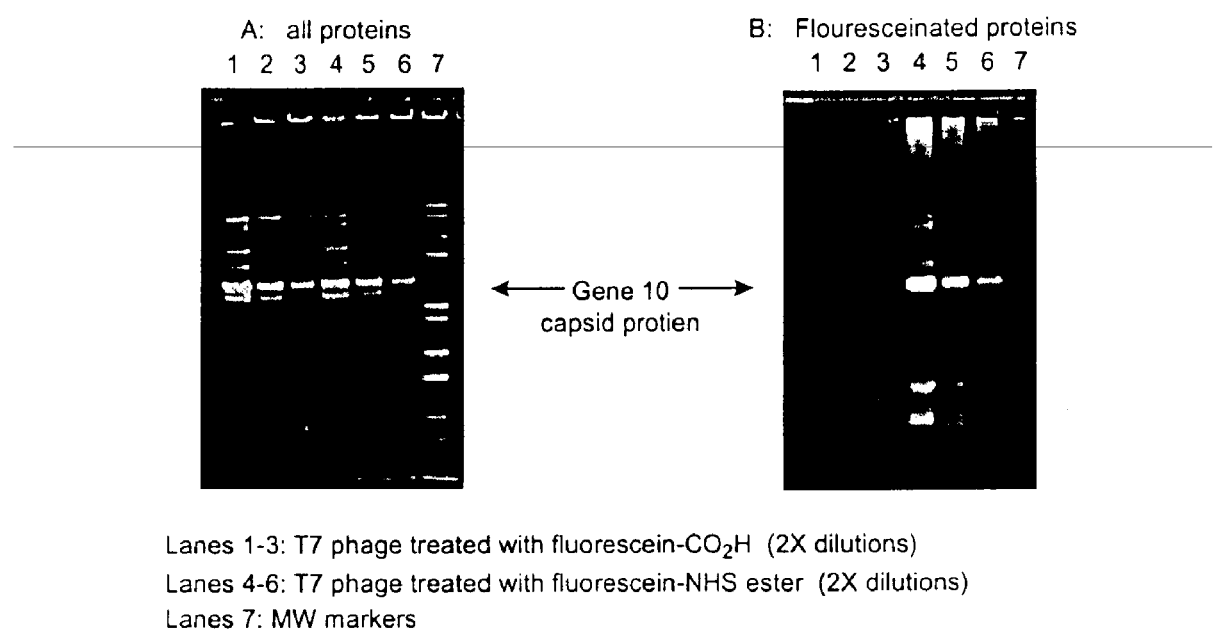
FIGS. 16A and 16B are protein gels of T7 phage viewed in two channels: Channel A shows all the proteins on the gel; channel B shows only fluorescein-conjugated proteins.

T7 phage were treated with fluorescein-NHS ester as well. The results for treatments of T7 phage treated with fluorescein-NHS ester are shown in FIGS. 16A and 16B. The two images are again of the same protein gel. Image A visualizes all the proteins on the gel, while image B visualizes only those proteins that have been fluoresceinated. The major band evident in lanes 1-6 of image A is the gene 10 capsid protein. Image B clearly shows that this is the major site of attachment in T7 phage, although other minor coat proteins may be labeled as well.

EXAMPLE 11

ELISA Detection of Fluorescein-Conjugated T7 S-Tag Phage

I. General

Another set of experiments was conducted to determine if fluoresceinated T7 phage could be captured by immobilized anti-fluorescein antibody similar to the ability of biotinylated phage to be captured.

II. Methods

50 μL of a 0.1 mg/mL solution of mouse monoclonal anti-fluorescein antibody (Molecular Probes) was added to columns 1 and 2 of a 96-well microtiter plate and incubated at 37° C. for 1.5 h. The plate was washed with PBS, and 300 μL of 0.1% BSA/PBS was added to each well of columns 1-4 and incubated at 37° C. for 3 h. The plate was washed and 50 μL of 0.1% BSA/PBS was added to each well, followed by 50 μL of a 10× dilution of each of the phage solutions prepared in Example 10 II.A. reactions 1-5. The plate was incubated overnight at 4° C., and washed with PBS. 50 μL of S-protein-horseradish peroxidase conjugate (1:5000 dilution in 0.1% BSA/PBS) was added and incubated at room temperature for 2 h. The plate was washed, and 100 μL of substrate (9 μL of 30% $H_2O_2$ added to 5 mL of 1×ABTS) was added. The absorbance at 405 nm was measured in a microtiter plate reader.

III. Results

Figure 17:
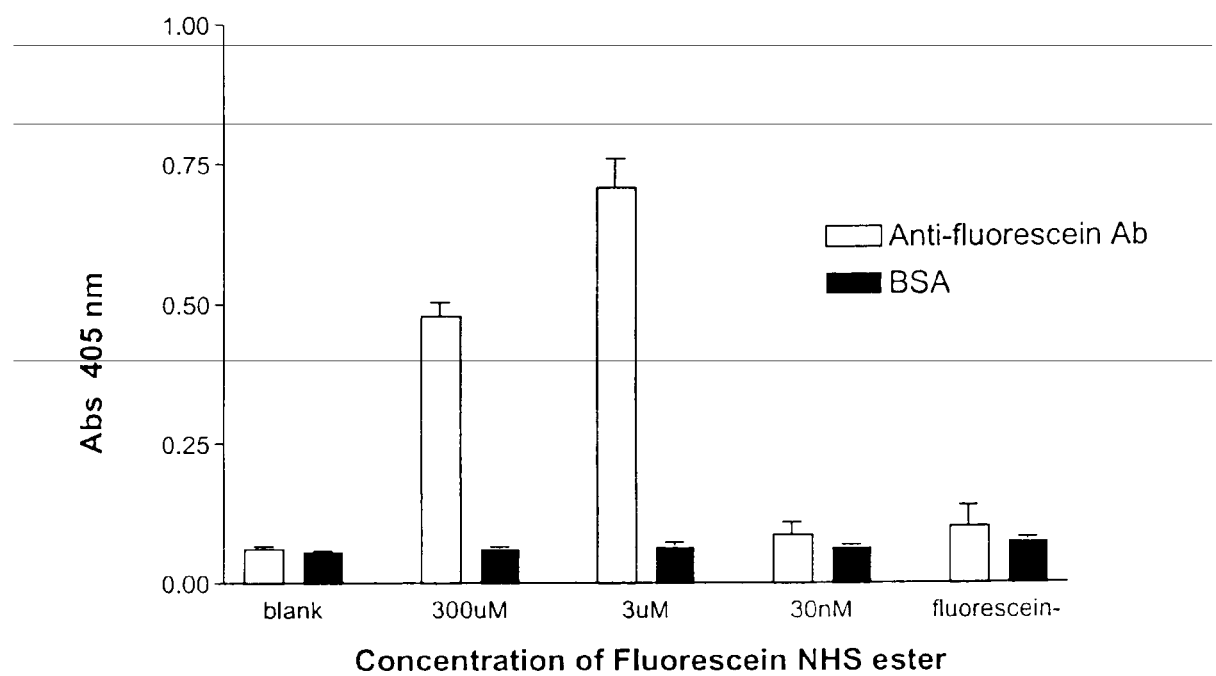
FIG. 17 depicts results of ELISA detection of fluorescein-conjugated T7 phage captured by immobilized anti-fluorescein antibody. The fluorescein was chemically conjugated to the phage using NHS ester attachment chemistry.

The ability of the immobilized anti-fluorescein antibodies to capture T7 phage reacted with varying concentrations of fluorescein are shown in FIG. 17. Phage reacted at 300 μM and 3 μM bound specifically to the immobilized anti-fluorescein antibody.

EXAMPLE 12

Comparison in Cellular Uptake between Folate-conjugated Filamentous Phage and Folate-Conjugated Icosahedral Phage I. Experimental A. Conjugation of Folate to Phage To a 1 mL microfuge tube was added 160 uL PBS buffer, 200 uL of a $6 \times 10^{11}$ pfu/mL stock of filamentous or T7 415 phage and 20 uL of a 6 mM solution of succinimidyl-4-formyl benzoate (see structure below) in DMSO. This solution was incubated on ice for 2 hr.

At 2 hr, 20 uL of a 6 mM solution of folate-hydrazide (TW032-75, see structure below) in DMSO was added, and the incubation was continued at room temperature for 3 hr.

100 uL of a solution of 50% PEG was added and the solution cooled to 0 C, then spun at $13 \times 10^3$ rpm for 5 min at 4 C.

The supernatant was removed, and the pellet resuspended in 400 uL PBS. This stock solution of folate-conjugated phage was used in cell uptake experiments.

Folate-hydrazide (TW032-75):

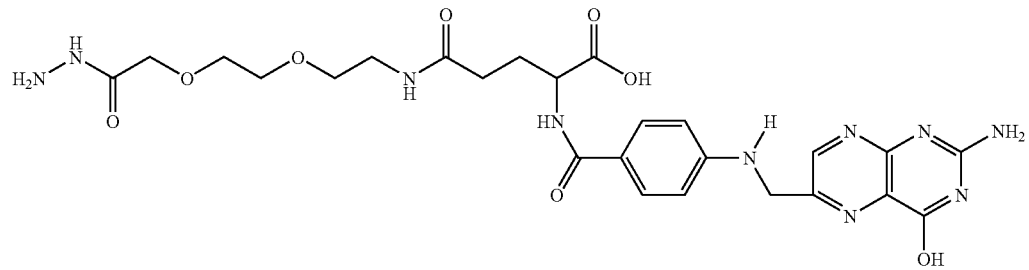

Molecular Weight = 600.60
Exact Mass = 600
Molecular Formula = C25H32N10O8

Succinimidyl-4-formyl benzoate:

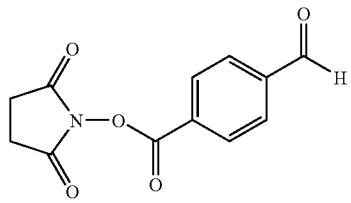

B. Cellular Uptake of Folate-Conjugated Filamentous Phage

CHO cells transfected by electroporation with the gene for the human folate receptor were washed twice with pH 5.5 buffer, soaked 10 min in pH 5.5 buffer and resuspended at $10^6$ cells/mL in folate-free RPMI 1 mL aliquots of cells were dispensed into microfuge tubes. Cells treated with folic acid were pre-incubated with 1.5 µM folic acid 37° C. for 1 hr prior to addition of phage. These cells were used in negative control experiments, as incubation with folic acid results in the folate receptor sites being occupied prior to the addition of the phage. Cells incubated at 4° C. were pre-incubated at 4° C. for 1 hr. prior to addition of phage.

Figure 18:
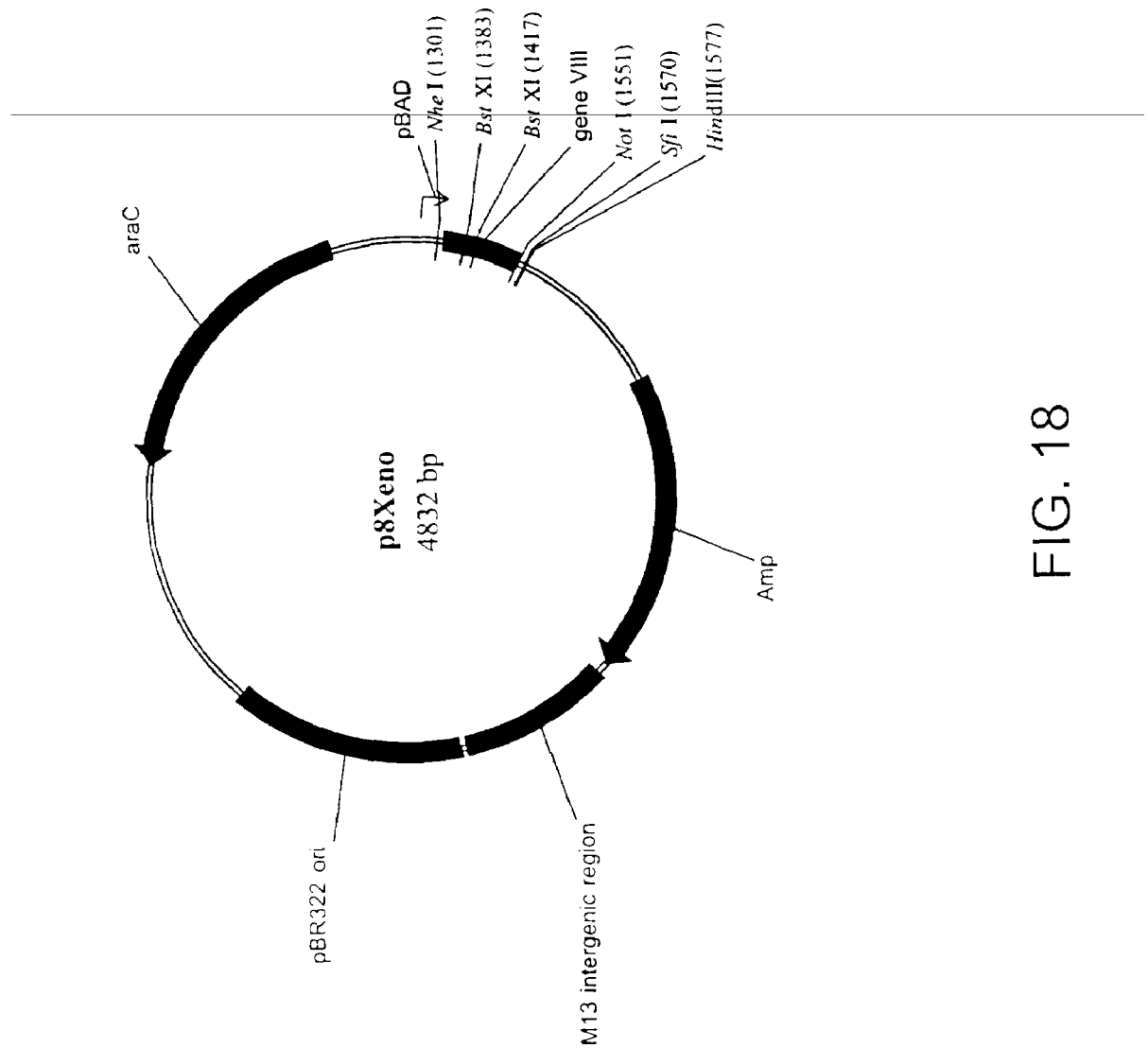
FIG. 18 is a map of the pVIII phagemid vector p8Xeno. The vector was constructed by inserting gene VIII of M13 into the multiple cloning site of the phagemid vector pBAD18. The pBAD promoter of the arabinose operon and its regulatory gene, araC, tightly regulate the expression of pVIII.

A total of $10^9$ TU of phage were added to each aliquot of $10^6$ cells and incubated at room temperature or 4° C. for 2 hr. Cells incubated at room temperature are able to perform endocytosis, whereas endocytosis at 4° C. is significantly inhibited. The phage added were either only wild type filamentous phage (P8 Xeno; see FIG. 18), only filamentous phage conjugated with folic acid, or a spike of folate-conjugated filamentous phage in a background of wild type filamentous phage at a level of 1/100.

Following the above incubation period, cells were pelleted by centrifugation, supernatant removed, and the cells were washed three times with PBS. Cells incubated at 4C were washed with ice cold PBS and centrifuged at 4° C.

The cells were resuspended in 800 uL stripping buffer (50 mM glycine, pH 2.8, 0.5M NaCl, 2M urea, 2% polyvinylpyrolidinone), incubated 10 min to remove any phage bound to the surface of the cells, neutralized with 400 uL 1M Tris-HCl pH 7.4, pelleted and supernatant removed.

The cells were resuspended and lysed in 800 uL 100 mM triethylamine, allowed to sit 10 min, then neutralized with 400 uL 1M Tris-HCl pH 7.4.

These lysates were titered by diluting to approximately $10^4$ TU/mL in PBS, adding 10 uL of this solution to 100 uL of K91recA cells (O.D. 0.6-0.8), incubating 20 min at 37° C., then plating onto LB/amp plates and incubating overnight at 37° C.

C. Cellular Uptake of Folate-Conjugated T7 Phage

KB cells that had been grown in folate-free RPMI with 5% fetal bovine serum were washed 2× with folate-free RPMI containing 0.1% BSA, and resuspended at $10^6$ cells/mL.

The cells were dispensed in 1 mL aliquots. All cells were pelleted by centrifugation. Cells treated with PI-PLC (phosphoinositide-specific phospholipase C) were resuspended in folate-free RPMI containing 0.1% BSA and 0.1U/mL PI-PLC and incubated 1 hr at 37° C. Cells treated with folic acid were resuspended in folate-free RPMI containing 0.1% BSA and 1.5 uM folic acid and incubated 1 hr at 37° C. All other cells were resuspended in folate-free RPMI containing 0.1% BSA and incubated either at 37° C. or 4° C. for 1 hr. All cells were then pelleted and resuspended in folate-free RPMI containing 0.1% BSA, except those cells treated with folic acid which were resuspended in folate-free RPMI containing 0.1% BSA and 1.5 uM folic acid. Cells to be incubated at 4° C. were again recooled to 4° C. prior to addition of phage.

A total of $10^8$ TU of phage were added to each aliquot of $10^6$ cells and incubated at 37° C. or 4° C. for 1 hr. The phage added were T7 415 phage that either had or had not been conjugated with folic acid. Incubation with folic acid served as a negative control by blocking folate receptor sites prior to the addition of the phage.

Following the above incubation period, cells were pelleted by centrifugation, supernatant removed, and the cells were washed three times with folate-free RPMI containing 0.1% BSA. Cells treated with folic acid were washed with folate-free RPMI containing 0.1% BSA and 1.5 uM folic acid. Cells incubated at 4° C. were washed with ice cold folate-free RPMI containing 0.1% BSA and centrifuged at 4° C.

The cells were resuspended in 800 uL stripping buffer (50 mM glycine, pH 2.8, 0.5M NaCl, 2M urea, 2% polyvinylpyrolidinone), incubated 10 min to remove phage bound at the surface of the cells, neutralized with 400 uL 1M Tris-HCl pH 7.4, pelleted and supernatant removed.

The cells were resuspended and lysed in 1 mL 1% SDS in PBS, let sit 10 min, then diluted to approximately $10^3$ TU/mL into LB. These lysate solutions were titered by adding 100 uL to 200 uL of BL21 cells (O.D. 0.6-0.8) and 3 mL warm top agar and plated onto LB plates. The plates were then incubated at room temperature overnight.

II. Results/Conclusion

Figure 19A:
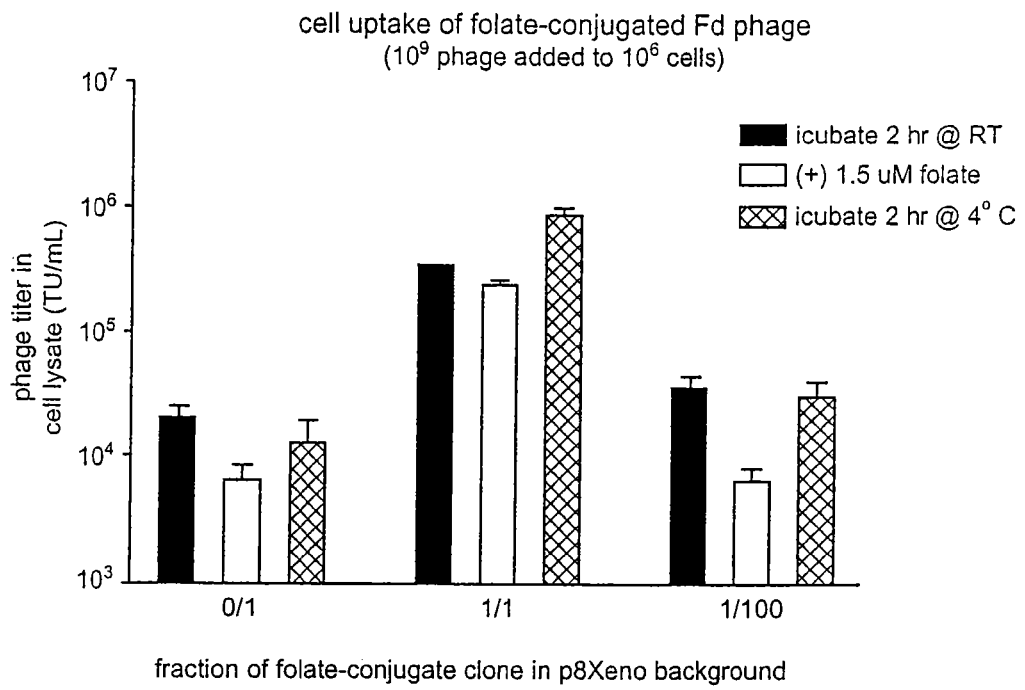
FIGS. 19A and 19B show comparative results for the uptake of folate-conjugated filamentous and icosahedral phage into cells expressing the human folate receptor.
Figure 19B:
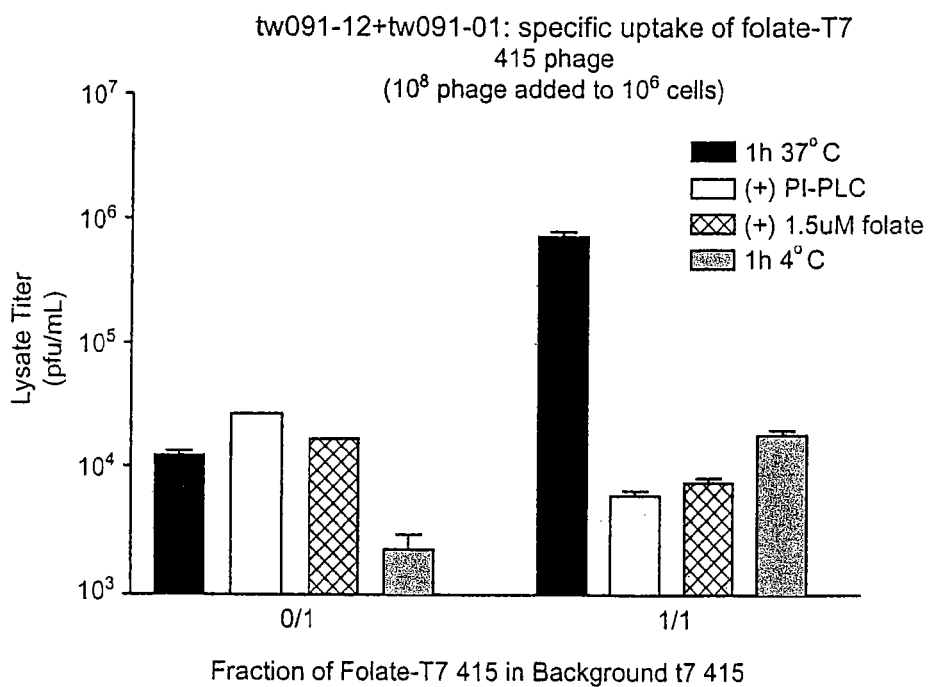

Results are shown in FIGS. 19A and 19B. FIG. 19A shows results for cellular uptake with filamentous phage conjugated to folate under various conditions. Transport in experiments conducted only with folate-conjugated phage was higher than in negative control experiments conducted without folate-bearing phage and was higher than in experiments conducted with a dilution of the folate-bearing phage as expected. However, in each set of experiments, the phage titer for experiments conducted under conditions promoting endocytosis (i.e., room temperature) was approximately equivalent to the titer obtained for the negative controls (i.e., incubation at 4° C. or preincubation with folate).

As illustrated in FIG. 19B, however, evidence of endocytosis was much clearer when experiments were conducted with icosahedral phage conjugated to folate. In these experiments, the titer was significantly higher for trials conducted with folate-conjugated phage as compared to the negative controls. Thus, these results unexpectedly demonstrate that enhanced results can be obtained in certain endocytosis screening assays when compounds are displayed on icosahedral phage as compared to filamentous phage.

EXAMPLE 13

Screening a 36-Member Library of Folate Analogs Displayed on T7 Phage for Compounds that are Endocytosed into Cells Via the Human Folate Receptor I. General To assess the utility of the compounds on phage technology to select compounds that are endocytosed by cells, a small library of folate analogs on T7 phage was constructed and screened against KB cells, which express high levels of the human folate receptor.

II. Experimental

A. Preparation of the Synthetic Compound Library

A library of synthetic analogs of folic acid was constructed in a parallel fashion in which glutamate, 7 aminobenzoic acids, and 5 nicotinic acids were assembled. The final member of the library was the folate hydrazide compound described in Example 12. The first building block to be attached to solid support was the PEG-based linker. This molecule is common to all library members, and consists of a masked hydrazide attachment to the bead on one end, and an azide functional group on the other. The masked hydrazide attachment functionality is designed to unveil a hydrazide functional group upon treatment with acid. Thus all library compounds contained a hydrazide functional group following acidic cleavage from the solid support, allowing for their attachment to appropriately derivatized phage particles. The azide functionality was reduced to an amine using Staudinger reduction conditions employing trimethylphosphine. The azide-PEG linker was attached to Wang resin (1 mmol/g) and reduced to the amine for library construction. Construction of the library consisted of three coupling steps, with glutamate attached during the first coupling step, 7 aminobenzoic acids in the second step, and 5 nicotinic acids in the third step. Optimal conditions for each of these amide-bond forming steps were determined prior to library construction.

Prior to attachment of the compounds to encoded T7 phage particles, the binding affinity of each folate analog for the human folate receptor was measured in a radioligand competition binding assay using $^3$H labelled folate and an immobilized soluble form of the human folate receptor. All of the folate analogs tested in this assay demonstrated a binding affinity greater than 30 µM for the soluble form of the human folate receptor, while the active folate-hydrazide compound had an affinity of approximately 1 nM.

B. Attachment of Compounds to Encoded Phage

T7 phage clones containing unique DNA sequence tags were grown in microtiter plates and partially purified by precipitation with polyethylene glycol. To prepare the encoded individual phage clones arrayed in microtiter plates for attachment of the folate analogs, they were first derivatized to bear a reactive aldehyde on their surface. This was accomplished by reacting the phage with 300 uM succinimidyl 4-formylbenzoate for 2 h at 4° C. Each of the aldehyde-labeled phage clones was then incubated with a hydrazide-containing folate analog (300 uM final concentration) for 2.5 h at room temperature to attach multiple copies of the small molecules to the phage. Following the 2.5 h incubation with the hydrazide containing compounds, 2-hydroxyethylhydrazine was added (3 mM final) to each well and incubated for 2 h at room temperature to quench any unreacted aldehyde sites remaining on the phage surface. This capping step is necessary to prevent cross-reaction between phage clones and other members of the library, as all the phage clones, and the hydrazide-containing small molecules with which they were reacted, are combined for purification of the phage away from the excess compounds in the final step. The individual attachment reactions were pooled and phage particles were further purified by CsCl density centrifugation. Recovered folate-analog conjugated phage particles were then dialyzed in PBS and stored at 4° C.

C. Screening Library for Cellular Uptake

KB cells were grown adherently in folate-free RPMI with 5% fetal bovine serum in a T75 flask. Prior to screening the compound library the media was removed and replaced with folate-free RPMI containing 0.1% BSA. An aliquot of the folate-analog phage library (~$10^9$ pfu) was added to the flask containing $10^7$ KB cells and incubated for 2 h at 37° C. Following the incubation period, the cells were detached from the flask by adding PBS containing 5 mM EDTA and incubating for 5 minutes at 37° C. The cell suspension was transferred to a tube and cells were pelleted by centrifugation. The cells were washed 3× with PBS followed by a single wash with "stripping" buffer (50 mM glycine, pH 2.8, 500 mM NaCl, 2M urea, 2% polyvinylpyrolidone) to remove phage particles that were both specifically and non-specifically bound to the surface of the cells. The cell suspension was neutralized by the addition of one half volume of 1 M Tris and centrifuged to pellet the cells. Cells were then lysed with PBS containing 1% SDS to recover phage that were endocytosed. To determine the number of recovered phage particles the lysate was titered by preparing a series of dilutions, infecting BL21 cells and plating on LB agar plates. The plates were incubated for 2-3 h at 37° C. until plaques were clearly visible. The remainder of the recovered phage were amplified by infecting a culture of BL21 cells, incubating for 1-3 hours at 37° C. until lysis was observed, followed by centrifugation at 8,000×g for 10 minutes to clarify the lysate.

D. Identification of Selected Compounds

To identify the T7 encoded phage selected from the library in the KB cell uptake assay, and thus the active compounds, the DNA tags from the recovered phage population were first amplified by PCR. The DNA was then digested with NotI, followed by agarose gel isolation of the fragment containing the unique sequence tag and SP6 RNA polymerase promoter sequence (FIG. 12). This template was added to an in vitro transcription reaction that contained SP6 RNA polymerase and $^{32}$P labelled CTP to generate a radiolabelled CRNA probe. A nylon membrane spotted with phage DNA from each folate-analog library member was then hybridized overnight at 50C with the radiolabelled probe (3×$10^6$ cpm) in hybridization buffer containing 50% formamide. The filter was washed several times at room temperature, exposed to a phosphor screen, and developed using a Molecular Dynamics Typhoon phosphorimager.

III. Results

Figure 20:
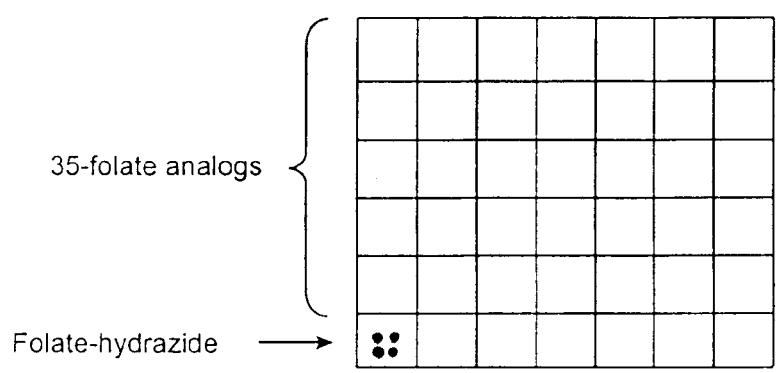
FIG. 20 shows hybridization results from screening the 36-member folate analog library attached to T7 phage for uptake into cells expressing the human folate receptor. The probe was produced from phage recovered from the cell lysate and was hybridized to the library archive array.

Results of the hybridization revealed that the phage clone labelled with the folate-hydrazide compound was the only one enriched in the recovered population (FIG. 20). To verify this result random clones from the lysate were sequenced and the deduced DNA tags were compared to the known sequence tag of the folate-hydrazide clone. The folate labelled phage clone was present in 8 out of 21 sequences, or 38% of the population.

EXAMPLE 14

Screening a 980-Member Library of Folate Analogs Displayed on T7 Phage for Compounds that are Endocytosed into Cells Via the Human Folate Receptor I. General To test the screening method with a reasonably large collection of compounds, a library of 980 analogs of folic acid analogs was constructed using combinatorial synthesis followed by attachment to individually encoded T7 phage particles. The resulting phage-folate analog library was screened for cellular uptake in KB cells.

II. Experimental

A. Preparation of the Library

A library of synthetic analogs of folic acid was constructed, as described in Example 13, in which all possible combinations of 20 amino acids, 8 aminobenzoic acids and 6 nicotinic acids were assembled. The 20 amino acid building blocks consisted of a sampling of natural and unnatural amino acids. Included were building blocks which probe the regiospecificity of attachment to glutamic acid, as most reports suggest that coupling through the gamma-carboxylate is necessary to retain binding to the human folate receptor. Amino acids that change the negative charge of glutamate to a positive charge, and the neutral isostere glutamine were included to probe the charge requirement for binding the folate receptor. One of the amino acids was a null (no amino acid) such that the aminobenzoic acid building blocks were attached directly to the PEG linker.

Following attachment and deprotection of these 20 amino acids, the resin from each of these amino acid addition reactions was subdivided into 8 reaction vessels for the coupling of the aminobenzoic acid analogs. These consisted of four para-aminobenzoic acids, three meta-aminobenzoic acids and one para-aminomethylbenzoic acid. Studies have shown that the three meta-aminobenzoic acids and the para-aminomethylbenzoic acid require FMOC protection of the amine to avoid oligomerization on solid support, while the para-aminobenzoic acids do not. Diisopropyl carbodiimide and hydroxybenzotriazole were used to couple the aminobenzoic acid derivatives to the available amine on solid support, using five equivalents of all reagents for the meta-aminonenzoic acids and para-aminomethylbenzoic acid, and ten equivalents of all reagents for the para-aminobenzoic acids. Extensive rinsing of the resin, and deprotection of the FMOC protected inputs with 20% piperidine/NMP was done to prepare the resin for the final coupling step.

The resin from each aminobenzoic acid coupling step was further subdivided into 6 reaction vessels for attachment of the nicotinic acid derivatives. These building blocks were chosen to closely mimic the pteroic acid portion of folic acid, and to provide greatly simplified heterocyclic analogs. The nicotinic acid analogs were attached to the amine of the aminobenzoic acids using 2 equivalents of each of the nicotinic acid, HATU and diisopropylethylamine in N-methylpyrrolidinone as the solvent. Extensive rinsing of the resin was done to prepare each aliquot for cleavage of the compounds from solid support. Each of the compounds was cleaved into one well of a deep well microtiter plate using 500 uL to 1 mL of neat trifluoroacetic acid. The trifluoroacetic acid was removed under high vac, and the dried compounds dissolved in 500 uL to 1 mL of DMSO. The scale of the library was chosen such that each aliquot of resin provides 10 umol of each of the 960 members as the maximal theoretical yield. Consequently, the final concentration of each compound in DMSO may be up to 10 mM. This scale provided concentrations of the small molecule library members that were sufficient for conjugation to phage particles. HPLC and LC-MS analysis of a portion of each of approximately 10% of the library compounds was performed to insure that the desired compounds were synthesized in greater than 90% purity.

In addition to the 960 compounds described above, 20 compounds were included in which pteroic acid was attached through one of 19 amino acids or directly to the PEG linker described in Example 13. These compounds were expected to have high affinity for the folate receptor as they share the same heterocyclic moiety as folic acid, which has been shown to be critical for recognition of the folate receptor. A binding assay with these 20 compounds demonstrated that they have similar affinities for the folate receptor as folic acid itself. The method used to synthesize these 20 compounds follows closely the method used for the 960 compounds described above. Trifluoroacetyl protected pteroic acid was attached to the 19 amino acids or directly to the PEG linker using the diisopropylcarbodiimide/hydroxybenzotriazole method. Following attachment, the trifluoroacetyl group was removed using 20% propylamine in N-methylpyrrolidinone. Lastly, the compounds were removed from solid support into a deep well microtiter plate using 500 uL to 1 mL of neat trifluoroacetic acid, concentrated and dissolved in DMSO as described above.

B. Attachment of Compounds to Encoded Phage

A total of 980 T7 phage clones containing unique DNA sequence tags were grown in microtiter plates and partially purified by precipitation with polyethylene glycol. The individual phage clones were then arrayed in microtiter plates for attachment of the folate analogs as described in Example 13. Following compound attachment the contents of the wells were pooled, phage were precipitated with PEG, and phage particles were further purified by CsCl density centrifugation. Recovered folate-analog conjugated phage particles were then dialyzed in PBS and stored at 4C.

C. Screening Library for Cellular Uptake

KB cells were grown adherently in folate-free RPMI with 5% fetal bovine serum in a T75 flask. Prior to screening the compound library the media was removed and replaced with folate-free RPMI containing 0.1% BSA. An aliquot of the 980-member folate-analog phage library ($\sim 10^{10}$ pfu) was added to the flask containing $10^7$ KB cells and incubated for 2 h at 37° C. Following the incubation period, the cells were detached from the flask by adding PBS containing 5 mM EDTA and incubating for 5 minutes at 37° C. The cell suspension was transferred to a tube and cells were pelleted by centrifugation. The cells were washed 3× with PBS followed by a single wash with "stripping" buffer (100 mM glycine, pH 2.5, 500 mM NaCl) to remove phage particles that were both specifically and non-specifically bound to the surface of the cells. The cell suspension was neutralized by the addition of one half volume of 1 M Tris and centrifuged to pellet the cells. Cells were then lysed with PBS containing 1% SDS to recover phage that were endocytosed. To determine the number of recovered phage particles the lysate was titered by preparing a series of dilutions, infecting BL21 cells and plating on LB agar plates. The plates were incubated for 2-3 h at 37° C. until plaques were clearly visible. The remainder of the recovered phage were amplified by infecting a culture of BL21 cells, incubating for 1-3 hours at 37° C. until lysis was observed, followed by centrifugation at 8,000×g for 10 minutes to clarify the lysate.

D. Identification of Enriched Active Folate Analog Clones

The twenty clones in the library that were attached to known active folate analogs were sequenced to identify their unique DNA tags. The tags from 100 individual clones recovered in the KB cell lysate were then amplified by PCR and sequenced.

III. Results

Examination of the sequences revealed that one of the known positive clones appeared 6 times; a 60-fold enrichment of this clone from the starting population. 14 of the remaining 94 sequences corresponded to other known positive clones (one appeared 3 times). Therefore active folate analogs were enriched ~10-fold from the starting population after a single round of selection for uptake in KB cells.

The examples and embodiments described are for illustrative purposes only and that various modifications or changes in light thereof will be suggested to persons skilled in the art and are to be included within the spirit and purview of this application and scope of the appended claims. All publications, patents, and patent applications cited herein are hereby expressly incorporated by reference in their entirety for all purposes to the same extent as if each individual publication, patent or patent application were specifically and individually indicated to be so incorporated by reference.

What is claimed is:

1. A method of screening a library of compounds for the capacity to be transported into or through a cell expressing one or more receptor-type transport proteins, comprising:
    (a) providing a plurality of icosahedral phage displaying different compounds; and
    (b) contacting the plurality of icosahedral phage with the cell, wherein icosahedral phage displaying a compound that is a substrate for the one or more receptor-type transporters is transported into or through the cell; and
    (c) identifying at least one icosahedral phage displaying a compound that is transported into or through the cell.

2. The method of claim 1, wherein the compound is an expressed polypeptide that is a component of a fusion protein that comprises a capsid protein of the icosahedral phage.

3. The method of claim 1, wherein
    the cell is one of a population of cells that express one or more receptor-type transport proteins;
    the contacting step comprises contacting the plurality of icosahedral phage with the cell population; and
    the identifying step comprises identifying at least one phage that is transported through one cell of the population of cells, such a phage displaying a compound that is a candidate ligand for a receptor-type transport protein.

4. The method of claim 3, wherein the population of cells comprise different cells, the different cells expressing different receptor-type transport proteins, having different distinguishable characteristics and being located in a single reaction vessel, the contacting step results in the at least one phage being transported into or through one of the cells, and the method further comprises determining the identity of the cell through which the at least one phage is transported into or through from its distinguishable characteristic.

5. The method of claim 3, wherein the population of cells have been transformed with a DNA library encoding a plurality of receptor-type transport proteins and express a plurality of receptor-type transport proteins, and the method further comprises determining the identity of the cell through which the at least one phage is transported, such a cell expressing a candidate receptor-type transport protein that can transport the compound displayed by the at least one phage into or through the cell.

6. The method of claim 5, wherein the DNA library is a cDNA library from human intestinal epithelial cells.

7. The method of claim 1, wherein the contacting step is performed in vivo.

8. The method of claim 7, wherein the contacting step comprises introducing the plurality of icosahedral phage into a body compartment or tissue of an animal, and the cell is one of a plurality of cells lining the body compartment or tissue that express one or more transport proteins, whereby the at least one icosahedral phage is transported from the body compartment through the cells lining the body compartment into a tissue or fluid, and the method further comprises recovering the at least one phage from the tissue or fluid, the compound displayed by the at least one phage being a candidate substrate for one of the transport proteins.

9. The method of claim 8, further comprising repeating the method with recovered phage from the recovery step of one cycle forming the plurality of phage to be introduced into the body compartment of the animal in the next cycle.

10. The method of claim 9, wherein a different animal is used in each cycle of the method.

11. The method of claim 8, wherein the body compartment is the lumen of the gastrointestinal tract.

12. The method of claim 8, wherein the tissue or fluid is the blood or lymphatic fluid of the animal.

13. The method of claim 12, wherein the plurality of phage is introduced into the intestine of the animal, the cells through which transport occurs are intestinal epithelial cells and the at least one phage is retrieved from the blood of the animal.

14. The method of claim 8, wherein the plurality of phage is introduced into the circulatory system of the animal, the cells through which transport occurs are endothelial cells and the at least one phage is retrieved from the brain.

15. The method of claim 8, further comprising sealing the body compartment around the introduced plurality of phage to increase the available time for transport of phage through cells lining the compartment.

16. The method of claim 8, wherein the at least one phage is one of a plurality of recovered phage and is labeled with a reporter, and the method further comprises
    (c) contacting the recovered phage with a population of polarized cells transformed with a DNA library at least some members of which encode potential transport proteins, the cells being arranged as a monolayer on a membrane and the phage contacting the apical side of the cells;
    (d) detecting phage transported through the polarized cells to the membrane by virtue of the reporter;
    (e) recovering polarized cells in proximity to the transported phage; and
    (f) clonally expanding the recovered polarized cells.

17. The method of claim 1, wherein the identification step comprises obtaining a sample containing phage transported into or through a cell and plating the sample on a population of cells and detecting plaque formation.

18. The method of claim 1, wherein the plurality of icosahedral phage bear a reporter, and the identification step comprises detecting the reporter borne by the at least one phage.

19. The method of claim 18, wherein the reporter preferentially generates a signal once the reporter is internalized within the cell.

20. The method of claim 18, wherein the reporter is a fluorophore.

21. The method of claim 1, further comprising determining at least one characteristic of the compound that is a substrate for the one or more receptor-type transporters.

22. The method of claim 2, wherein different icosahedral phage harbor different heterologous nucleic acids that encode the expressed polypeptide, and the method further comprises determining the sequence of the heterologous nucleic acid of the at least one icosahedral phage to identify the compound that is a substrate for the one or more receptor-type transporters.

23. The method of claim 1, wherein the compound is a compound other than an expressed polypeptide.

24. The method of claim 23, wherein different icosahedral phage harbor different heterologous nucleic acid tags, and the method further comprises decoding the heterologous nucleic acid tag of the at least one icosahedral phage to identify a characteristic of the at least one compound that is transported into or through the cell.

25. The method of claim 1, wherein the contacting step is performed in vitro.

26. The method of claim 25, wherein the cell is one of a population of polarized cells, and the polarized cells are layered above a membrane that is permeable to the icosahedral phage, and wherein the assaying step comprises applying the plurality of icosahedral phage to the apical side of the polarized cells, whereby the at least one icosahedral phage passes through the polarized cell monolayer and is collected on the basolateral side of the polarized cells.

* * * * *